United States Patent
Jørgensen et al.

[11] Patent Number: 5,827,501
[45] Date of Patent: Oct. 27, 1998

[54] USE OF FREE RADICALS IN ESR AND ESREMR IMAGING

[75] Inventors: Mikkel Jørgensen, Glostrup, Denmark; Frode Rise, Oslo, Norway; Sven Andersson, Lomma; Torsten Almen, Malmö, both of Sweden; Arne Aabye, Oslo, Norway; Lars-Göran Wistrand, Lund; Håkan Wikstrom, Höllviken, both of Sweden; Klaes Golman, Rungsted, Denmark; Rolf Servin, Malmö ; Peter Michelsen, Arlöv, both of Sweden

[73] Assignee: Nycomed Imaging AS, Oslo, Norway

[21] Appl. No.: 477,568

[22] Filed: Jun. 7, 1995

Related U.S. Application Data

[62] Division of Ser. No. 916,974, Sep. 2, 1992.

[30] Foreign Application Priority Data

Feb. 12, 1990 [GB] United Kingdom .................... 9003105
Jun. 1, 1990 [GB] United Kingdom .................... 9012300

[51] Int. Cl.⁶ .................................................... A61K 49/04
[52] U.S. Cl. ............................................................ 424/9.33
[58] Field of Search ............................................. 424/9.33

[56] References Cited

FOREIGN PATENT DOCUMENTS 8810419 12/1988 WIPO .
9002345 3/1990 WIPO .

OTHER PUBLICATIONS

J. Org. Chem., 48, 1983, pp. 3716–3720.
J. Org. Chem., 47, 1982, pp. 259–264.
J. Am. Chem. Soc., 89, 1967, pp. 2054–2058.
Radiology, 147, 1983, pp. 781–788.
Angew. Chem. 78, 1966, pp. 98–107.

*Primary Examiner*—Yogendra N. Gupta
*Attorney, Agent, or Firm*—Bacon & Thomas

[57] ABSTRACT

The present invention relates to a method of generating an electron spin resonance enhanced magnetic resonance image of a sample which comprises introducing into the sample a magnetic resonance signal enhancing amount of a free radical and generating an enhanced electron spin resonance image of the sample. The method comprises using as the free radical an inert triarylmethyl free radical, wherein each aryl moiety of said triarylmethyl radical, which may be identical or different, comprises an optionally substituted 6-membered carbocyclic or thienyl ring. The invention also relates to the use of trityls in ESR imaging.

5 Claims, 1 Drawing Sheet

USE OF FREE RADICALS IN ESR AND ESREMR IMAGING

This application is a Division of application Ser. No. 07/916,974, filed 02 Sep. 1992.

The present invention relates to the use of stable free radicals, in particular inert carbon radicals, as image enhancing agents in magnetic resonance imaging (MRI) as well as to contrast media containing such radicals and to the use of such radicals and their non-radical precursors in the manufacture of MRI contrast media.

MRI is a diagnostic technique that has become particularly attractive to physicians as it is non-invasive and does not involve exposing the patient under study to potentially harmful radiation, such as for example the X-radiation of conventional radiography.

This technique, however suffers from several serious drawbacks, including in particular the expense of manufacture and operation of the MRI apparatus, the relatively long scanning time required to produce an image of acceptable spatial resolution, and the problem of achieving contrast in the magnetic resonance (MR) images between tissue types having the same or closely similar imaging parameters, for example in order to cause a tissue abnormality to show up clearly in the images.

The expense of manufacture and operation of an MRI apparatus is closely associated with the strength of the magnetic field that the primary magnet in the apparatus is required to generate in order to produce images of acceptable spatial resolution in an acceptable time.

MR images are generated by manipulation of the MR signals detected from the sample, for example a human or animal body, placed in a magnetic field and exposed to pulses of radiation of a frequency (typically radiofrequency (RF)) selected to excite MR transitions in selected non-zero spin nuclei (the "imaging nuclei", which are generally water protons in body fluids) in the sample.

The amplitude of the induced MR signals is dependent upon various factors such as the strength of the magnetic field experienced by the sample, the temperature of the sample, the density of the imaging nuclei within the sample, the isotopic nature and chemical environment of the imaging nuclei and the local inhomogeneities in magnetic field experienced by the imaging nuclei.

Thus many techniques have been proposed for enhancing MR image quality, for example by increasing MR signal amplitude or by increasing the difference in MR signal amplitude between different tissue types.

The imaging parameters (nuclear density, $T_1$ and $T_2$) for tissues of interest may be altered and many proposals have been made for doing this by the administration of magnetically responsive materials into patients under study (see for example EP-A-71564 (Schering), EP-A-133674 (Schering) and WO-A-85/04330 (Jacobsen)). Where such materials, generally referred to as MRI contrast agents, are paramagnetic they produce significant reduction in the $T_1$ of the water protons in the body zones into which they are administered or at which they congregate, and where the materials are ferromagnetic or superparamagnetic (for example as suggested by Jacobsen) they produce a significant reduction in the $T_2$ of the water protons. In either case the result is enhanced (positive or negative) contrast in the MR images of such zones.

The contrast enhancement achievable by such agents in conventional MRI is relatively limited and it is generally not such as to allow a reduction in the image acquisition period or in the field strength of the primary magnet.

Utilisation of the spin transition coupling phenomenon known as dynamic nuclear polarisation or as the Overhauser effect to amplify the population difference between the ground and excited spin states of the imaging nuclei by the excitation of a coupled ESR transition in a paramagnetic species present in the sample being imaged has been described by Hafslund Nycomed Innovation AB in WO-A-88/10419.

This new technique for generating a MR image of the sample, which is hereinafter termed electron spin resonance enhanced magnetic resonance imaging (ESREMRI), or Overhauser MRI, involves exposing the sample to a first radiation of a frequency selected to excite nuclear spin transitions in selected nuclei in the sample (radiation which is generally of radiofrequency or thereabouts and thus for convenience will be referred to hereinafter as RF radiation) and also exposing the sample to a second radiation of a frequency selected to excite electron spin transitions coupled to nuclear spin transitions for at least some of the selected nuclei (radiation which is generally of microwave frequency or thereabouts and thus for convenience is referred to hereinafter as MW or UHF radiation), the MR images being generated from the resulting amplified MR signals (free induction decay signals) emitted by the sample.

The paramagnetic substance which possesses the ESR transition which couples with the NMR transition of the image nuclei may be naturally present within the imaging sample or more usually may be administered as an ESREMRI contrast agent.

In WO-A-88/10419 various ESREMRI contrast agents were proposed, for the most part these being nitroxide stable free radicals, although the use of chloranil semiquinone radical and of Fremy's salt was also proposed.

In WO-A-90/00904 Hafslund Nycomed Innovation AB proposed the use of deuterated stable free radicals, in particular deuterated nitroxide stable free radicals, as ESREMRI contrast agents.

Organic free radicals however frequently have properties which render them unsuitable for use as ESREMRI contrast agents. Thus free radicals commonly are unstable in physiological conditions, or have very short half-lives leading to toxicity problems. A further drawback is the low relaxivity exhibited by many free radicals, which results in poor coupling of the electron and nuclear spin transitions and thus a poor enhancement of the magnetic resonance signal. A need therefore exists for improved free radical ESREMRI contrast agents.

The ESREMRI contrast agents so far proposed in the literature have all been "oxygen free radicals" that is to say radicals where the unpaired electron or electrons are associated with oxygen atoms.

We have now surprisingly found that carbon free radicals, i.e. radicals where the unpaired electron or electrons are primarily associated with carbon atoms are particularly attractive for use as ESREMRI contrast agents.

For such free radicals to be effective, they should be relatively long lived and to distinguish from free radicals which have a momentary existence, those usable as ESREMRI contrast agents will be referred to herein as being "inert" free radicals, that is having a half life of at least one minute at ambient temperature.

Viewed from one aspect the present invention thus provides the use of an inert carbon free radical for the manufacture of a contrast medium for use in ESREMRI.

Viewed from a further aspect, the invention also provides a method of magnetic resonance investigation of a sample, said method comprising introducing into said sample an inert carbon free radical, exposing said sample to a first radiation of a frequency selected to excite electron spin transitions in said free radical, exposing said sample to a second radiation of a frequency selected to excite nuclear spin transitions in selected nuclei in said sample, detecting free induction decay signals from said sample, and, optionally, generating an image or dynamic flow data from said detected signals.

Viewed from a still further aspect, the invention also provides a magnetic resonance imaging contrast medium comprising a physiologically tolerable inert carbon free radical together with at least one pharmacologically acceptable carrier or excipient.

For in vivo imaging, the inert carbon free radical should of course preferably be a physiologically tolerable radical, or one presented in a physiologically tolerable, e.g. encapsulated, form.

Inert carbon free radicals are well known and a range of these has been described for example by Ballester et al. (see JACS 93: 2215 (1971), J.Org.Chem. 47:259–64 and 4498 (1982), 48 3716 (1983), 53 1267–73 (1980), 54 4811–15 (1989), Accounts of Chemical Research 18:380 (1985) and references therein); Fox et al. (see JACS 109, 7088–94); Gomberg, JACS 22, 757 (1900); Neunhoffer Chem. Ber., 91, 1801 (1958); Maki, Chem. Phys, 35, 761 (1963); Dunnebacke, Chem.Ber. 122 533 (1989); Jundeikis JACS 84 1132 (1961); Sinclair, JACS 90 5074 (1968); Bent, JACS 84 3250 (1932); Falle, Canad. J. Chem. 44 1387 (1966); Ziegler, Annalen 458 248 (1927); Allan, JCS (1936) 440; Acta (Chem. Scand. 16 1817 (1962); Theilacker, Annalen 594 214 (1955); Muller, Angew. Chem. 5 6 (1966); Schlenck, Annalen 372 1 (1910); Teilacker, Angew. Chem. 69 322 (1957); Sabacky, JACS 89 2054 (1967); Muller, Tetrakedron Lett 3877, (1967); Marvel JACS 66 415 (1944); and Trapp, J. Chem. Phys 45 3472 (1966).

Preferred inert carbon free radicals for use according to the invention exhibit high stability to oxygen, to pH, for example in the range pH 5–9, and in aqueous solution, particularly stability up to a concentration of 300 mM. Further desirable characteristics include reduced tendency to dimerization, long half-life, preferably greater than 1 minute, particularly preferably greater than 1 hour and especially preferably 1 year, long relaxation times, both $T_{1e}$ and $T_{2e}$ preferably being greater than 1 μsec, high relaxivity, for example greater than 0.3 mM$^{-1}$sec$^{-1}$ and a small number of esr transition lines.

Particularly preferred inert carbon free radicals include the substituted methyl radicals, in particular triarylmethyl radicals where each of the three aromatic substituent groups may be the same or different and where two or three such groups may optionally be linked together. Particularly preferably the radical comprises optionally substituted six-membered carbocyclic or heterocyclic aromatic rings optionally carrying one or more fused carbocyclic or heterocyclic rings.

The possibility exists to optimize different characteristics, e.g. solubility, stability, line broadening, of the overall radical by appropriate combinations of different aryl substituents on the methyl carbon. Combinations, where two such aryl substituents, preferably identical, are selected to optimize stability and line broadening, and one aryl substituent is selected to optimize solubility are considered particularly interesting.

In order to optimize the above-mentioned desirable properties, a number of criteria need to be borne in mind in selecting or constructing triarylmethyl radicals for use according to the invention.

Thus, the aromatic rings of the triarylmethyl radical advantageously are substituted and the nuclear identities of nuclei in all substituents and their position within the molecule should be selected so as to minimise their effect (line splitting or broadening) on the esr transition.

In such cases, a six-membered aromatic ring is preferably substituted at the ortho and para positions. This is desirable in order to minimise dimerisation and oxygen attack on the molecule. The meta position is optionally substituted, preferably with a bulky substituent, again to minimise attack by oxygen and at least one of the substituents should conveniently comprise a water solubilizing moiety. Such substituents preferably have no magnetic moment, or have a very low effective spin density. Alternatively, in order to minimise their effect on the esr transition, the substituents should be bonded in such a manner that they are capable of free rotation.

Particularly preferred inert carbon free radicals include the triarylmethyl radicals of formula I

.C(Ar$^1$)$_3$          (I)

(where each group Ar$^1$, which may be the same or different, is preferably a substituted thienyl, phenyl, 4-pyridinyl, 3-pyridinyl, 2-pyridinyl, 5-pyrimidyl or 4-pyrimidyl group). Other preferred triarylmethyl radicals include those of formula Ia

(Ar$^{12}$)$_3$C.          (Ia)

where each Ar$^{12}$, which may be the same or different, comprises an optionally substituted 5–7 membered carbocyclic or heterocyclic aromatic ring optionally carying one or more fused carbocyclic or heterocyclic rings, one or more such Ar$^{12}$ groups preferably being a group Ar$^1$ as defined herein.

Particularly preferably each group Ar$^1$ represents a 6 membered carbon-attached carbocyclic or heterocyclic aromatic ring containing up to 2 non-adjacent ring nitrogens optionally substituted at the or any ortho carbon by a group R$^1$ to R$^4$, at the or any meta carbon by a group R$^2$ or R$^3$ and at any para carbon by a group R$^1$,R$^2$,R$^3$ or R$^4$, with the proviso that no more than two ring carbons are unsubstituted, preferably only one ring carbon at most being unsubstituted;

each of R$^1$ to R$^4$, which may be the same or different, independently represents a group of formula —M, —XM, —XAr$^2$ or —Ar$^2$; M represents a water solubilizing group, each group X, which may be the same or different, represents an oxygen or sulphur atom or a NH or CH$_2$ group;

Ar$^2$ represents a 5 to 10 membered aromatic ring. optionally substituted by a solubilizing group M; or groups R$^1$ and/or R$^4$ on different Ar$^1$ groups may together represent bridging oxygen or sulphur atoms or NR$^5$ or CR$^5$$_2$ groups, where R$^5$ represents a hydrogen atom or an optionally hydroxylated, optionally aminated, optionally alkoxylated, optionally carboxylated alkyl, oxoalkyl, alkenyl or alkaryl group;

or groups R$^2$ and R$^3$ may also represent hydrogen atoms or alkyl groups;

or adjacent groups R$^1$, R$^2$, R$^3$ or R$^4$, preferably groups at the ortho and meta portions, together with the two intervening carbon atoms may represent groups of formula

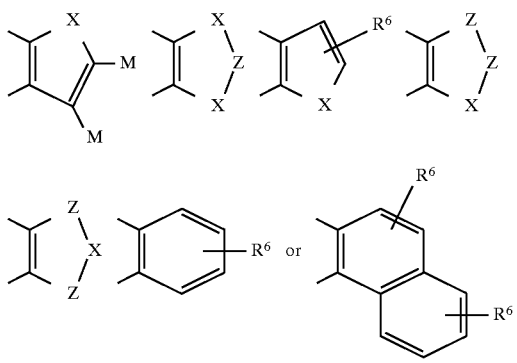

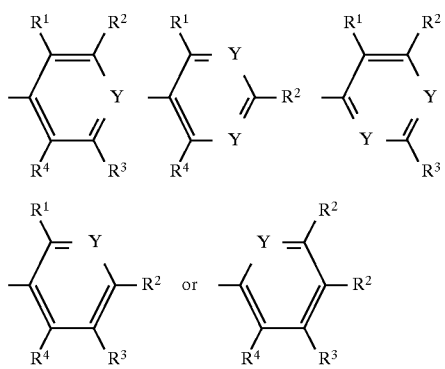

where $R^6$ represents a hydrogen atom, a hydroxyl group, an optionally alkoxylated, optionally hydroxylated acyloxy or alkyl group or a solubilising group M; Z represents an oxygen or sulphur atom or a group $NR^5$, $CR^7{}_2$, or $SiR^7{}_2$; each $R^7$, which may be the same or different, represents a hydrogen atom, an alkyl, hydroxyalkyl, alkoxycarbonyl or carbamoyl group or two groups $R^7$ together with the atom to which they are bound represent a carbonyl group or a 5 to 8 membered cycloalkylidene, mono- or di-oxacycloalkylidene, mono- or di-azacycloalkylidene or mono- or di-thiacycloalkylidene group optionally with the ring attachment carbon replaced by a silicon atom (preferably however in any Spiro structure the ring linking atom will be bonded to no more than three heteroatoms) and $R^7$ where it is other than hydrogen, is optionally substituted by a group $R^6$;
or a salt thereof.

In the radicals of formula I, the groups $Ar^1$ are preferably groups of formula

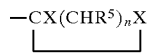

where each Y independently represents CH, or more preferably CM, C—XM, C—$Ar^2$, C—$XAr^2$ or a nitrogen atom.

Certain of the radicals of formula I are new and they, their salts and their non-radical precursors (i.e. compounds of formula $(Ar^{12})_3CX^4$ or $(Ar^1)_3CX^4$ where $X^4$ is a leaving group, e.g. hydrogen, hydroxyl, halogen, carboxyl, $CO_2OCO.C(Ar^{12})_3$ or $NNC(Ar^{12})_3$) form further aspects of the present invention.

In the inert carbon radicals of formula I, the solubilizing groups M may be any of the solubilizing groups conventionally used in diagnostic and pharmaceutical products. Particularly preferred solubilizing groups M include optionally hydroxylated, optionally alkoxylated alkyl or oxo-alkyl groups and groups of formulae $R^5$, $COOR^5$, $OCOR^5$, CHO, CN, $CH_2S(O)R^5$, $CONR^5{}_2$, $NR^5COR^5$, $NR^5{}_2$, $SO_2NR^5{}_2$, $OR^5$, $PO_3{}^{2-}$, $SOR^5$, $SO_2R^5$, $SO_3M^1$, $COOM^1$ (where $M^1$ is one equivalent of a physiologically tolerable cation, for example an alkali or alkaline earth metal cation, an ammonium ion or an organic amine cation, for example a meglumine ion), $—(O(CH_2)_n)_mOR^5$ (where n is an integer having a value of from 1 to 3 and m is an integer having a value of from 1 to 5), $$—CX(CHR^5)_nX$$

or $CH_2R^8$ (where $R^8$ is a hydrophilic $R^5$ group) or $SR^{10}$ where $R^{10}$ is a group $R^5$ or an alkyl group optionally substituted by one or more, especially two or three groups $COOR^5$, $OCOR^5$, CHO, CN, $CONR^5{}_2$, $NR^5COR^5$, $NR^5{}_2$, $SO_2NR^5{}_2$, $OR^5$, $PO_3{}^{2-}$, $SOR^5$, $SO_2R^5$, $SO_3M^1$, $COOM^1$, or $—(O(CH_2)_n)_mOR^5$.

Especially preferred as solubilizing groups M are groups of formula $C(H)_{3-n}(CH_2OH)_n$, $R^9$, $COR^9$, $SR^9$, $SOR^9$, $SO_2R^9$, $CON(R^9)_2$, $NR^9{}_2$, $NHR^9$ and $CONHR^9$ [where $R^9$ may represent a group

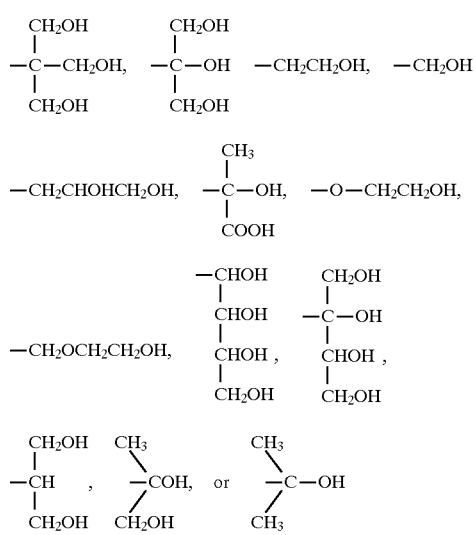

(although any $R^9$ group attached to a sulphur, nitrogen or oxygen atom is preferably not hydroxylated at the α carbon)], and groups of formula $SR^{12}$ where $R^{12}$ is a group $CH_2COOR^{13}$, $CH(COOR^{13})_2$, $CH_2CONHR^9$, $CH_2CONR^9{}_2$, $CR^5(COOR^{13})_2$, $CH(CN)CO_2R^{13}$, $(CH_2)_nSO_3{}^-M^1$, $(CH_2)_nCOR^1$, $CH(COR^9)CH_2COR^9$ and $CH(R^5)COR^9$ where n, $M^1$ and $R^5$ are as earlier defined and $R^{13}$ is a hydrogen atom, an alkyl group or a group $M^1$ or $R^9$.

Further especially preferred solubilising groups M or XM include groups of formula $X'C((CH_2)_nCOOR^{13})_2R^{14}$, $X'C((CH_2)_nCOOR^{13})_3$ and $X'C((CH_2)_nCOOR^{13})R^{14}{}_2$, where $R^{13}$ is as defined above, n is an integer from 1 to 3, X' is an oxygen or sulphur atom, and $R^{14}$ is a hydroxyalkyl group such as a group $R^9$ as earlier defined.

Other examples of preferred $R^1$ groups include for example the following structures —S—(CH₂CH₂O)ₙ' R¹⁹ — where n' is 0, 1 or 2 and R¹⁹ is hydrogen or C₁₋₄ alkyl —S—(CH₂)ₙ'—CO—R²³ — where R²³ is C₁₋₄ alkyl (e.g. methyl, ethyl or t-butyl), NR₂²¹ or OR²¹ and R²¹ is C₁₋₄ alkyl —COR²² — where R²² is hydrogen, hydroxyl, R²³, or COOR²¹

—CH₂O[CH₂CH₂O]ₙ'CH₃

—CH₂OCOR²¹ and

—CHX—CR₂⁵CR₂⁵—X — where X is oxygen or sulphur.

—CHX—CR⁵₂CR⁵₂—X where X is oxygen or sulphur.

Where M represents a group containing a moiety NR⁵₂, this may also represent an optionally substituted nitrogen-attached 5 to 7 membered heterocyclic ring optionally containing at least one further ring heteroatom, e.g. N or O, for example a group of formula

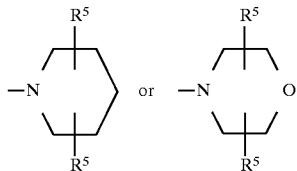

In the inert carbon radicals of formula (I), any alkyl or alkenyl moiety conveniently will contain up to 6, especially up to 4, carbon atoms and any aryl moiety will preferably contain 5 to 7 ring atoms in the or any aromatic ring and especially preferably will comprise an aromatic ring with 0, 1 or 2 further aromatic rings fused directly or indirectly thereto.

Preferred structures for the aryl substituents on the carbon radical centre include those in which at least one of such substituents carries at least one, and preferably two, fused rings of formula

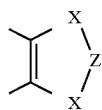

where X and Z are as defined before, especially rings of formulae

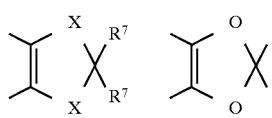

where X is oxygen or sulphur and R⁷ is hydrogen or optionally hydroxylated methyl.

Particularly preferred structures for the aryl groups Ar¹ in the inert carbon free radicals of formula I include the following:

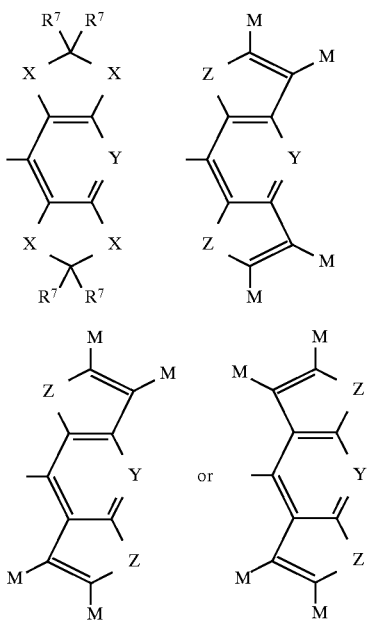

wherein X is oxygen or sulphur, Y is N, CCOOR⁵, CSR⁵, CM or C—XM and M, R⁵ and Z are as earlier defined.

Particularly referred structures include those in which CR⁷₂ represents CH₂, C(CH₂OH)₂ or C(CH₃)₂, X represents an oxygen or sulphur atom and those of formula

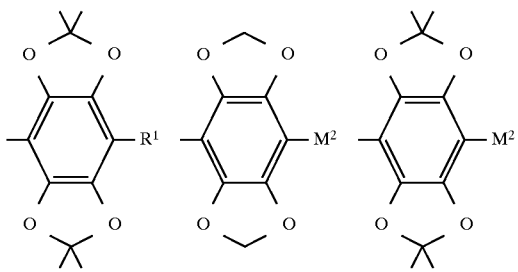

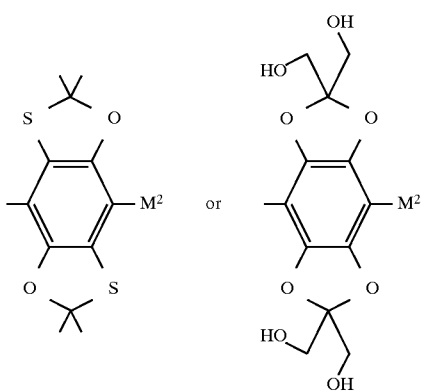

where R¹ is a group M or XM as hereinbefore defined and M² represents a solubilising group M or a group SCH₃, S(O)CH₃, S(O₂)CH₃, SCH₂CH₂N(CH₃)₂, SCH₂COOH, SCH₂COOCH₃, SCH₂COOCH₂CH₃ and SC(H)₃₋ₙ(CH₂OH)ₙ where n is an integer of from 1 to 3.

Especially preferred groups Ar¹ include optionally substituted benzo[1,2-d:4,5-d']bis[1,3]dioxole, benzo[1,2-d:4,5-d']bis[1,3]dithiole, and benzo[1,2-d:4,5-d']bis[1,3]oxathiole groups.

Preferred inert carbon free radicals for use according to the invention include the following:

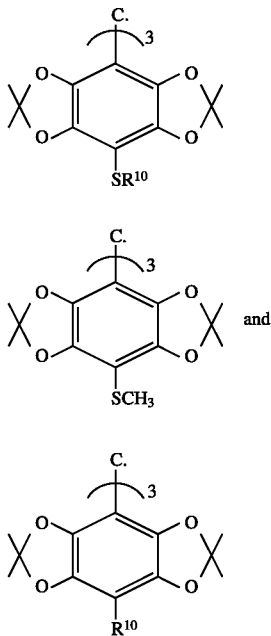

Especially preferred inert cation free radicals include

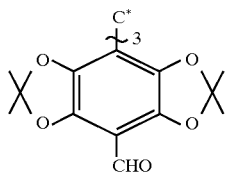

and water soluble derivatives thereof such as

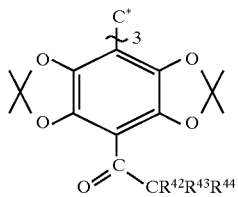

(where each of $R^{42}$, $R^{43}$ and $R^{44}$ are non-ionic solubilising groups e.g. hydroxyalkyl or alkoxyalkyl groups);

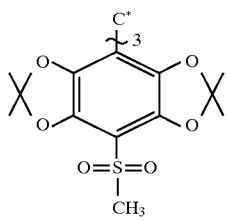

and water soluble derivatives thereof such as

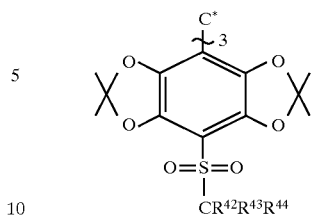

(where $R^{42}$, $R^{43}$ and $R^{44}$ are as defined above).

Inert free radicals which have relatively few transitions, e.g. less than 15, preferably less than 10, in their ESR spectra and radicals having narrow linewidth ESR transitions, e.g. up to 500 mG, preferably less than 150 mG, especially less than 60 mG and particularly less than 25 mG, are especially preferred for use as ESREMRI contrast agents. (The linewidths referred to are conveniently the intrinsic linewidths (full width at half maximum in the absorption spectrum) at ambient conditions).

Whilst low numbers of ESR transition lines are generally preferred to obtain more effective coupling of the ESR and NMR transitions, we have found that surprisingly good coupling, and therefore enhancement of the MR signal, may also be achieved with radicals showing a large number of ESR transitions.

Where the radicals have a multiplicity of ESR transitions, the hyperfine splitting constant is preferably very small. In this connection radicals having as few as possible non-zero spin nuclei, positioned as far away as possible from the paramagnetic centre are thus especially preferred.

Certain of the triarylmethyl free radicals of formula I are themselves novel and in a further aspect the present invention also provides novel inert carbon free radicals of formula I or salts thereof.

Most known triarylmethyl radicals have short relaxation times and half lives and are generally unstable, being oxygen-sensitive and particularly susceptible to dimerization, and thus would not generally be considered for use as contrast agents. Moreover known triarylmethyl radicals are water-insoluble and are therefore generally not suited for administration to the body. It was not therefore obvious to use triaryl methyl radicals as ESREMRI contrast agents.

The novel triarylmethyl radicals of the invention include radicals which surprisingly are stable at physiological pH, have long half lives (at least one minute, and preferably at least one hour), long relaxation times, and exhibit surprisingly good relaxivity. Water-soluble triaryl methyl radicals are a particularly important aspect of the invention.

The triarylmethyl radicals may be coupled to further molecules for example to lipophilic moieties such as long chain fatty acids or to macromolecules, such as polymers, proteins, polysaccharides (e.g. dextrans), polypeptides and polyethyleneimines. The macromolecule may be a tissue-specific biomolecule such as an antibody or a backbone polymer such as polylysine capable of carrying a number of independent radical groups which may itself be attached to a further macromolecule. Coupling to lipophilic molecules or substitution of the radical with lipophilic groups is particularly useful since it may enhance the relaxivity of the radicals in certain systems such as blood. Such lipophilic and macromolecular derivatives of the radicals of formula I and salts thereof form a further aspect of the present invention.

The linkage of a compound of formula I to the further molecule may be effected by any of the conventional methods such as the carbodiimide method, the mixed anhydride procedure of Krejcarek et al. (see Biochemical and Biophysical Research Communications 77: 581 (1977)), the cyclic anhydride method of Hnatowich et al. (see Science 220: 613 (1983) and elsewhere), the backbone conjugation techniques of Meares et al. (see Anal. Biochem. 142: 68 (1984) and elsewhere) and Schering (see EP-A-331616 for example) and by the use of linker molecules as described for example by Nycomed in WO-A-89/06979.

In view of their surprisingly beneficial properties, the novel triarylmethyl radicals of the invention may also be used as ESR spin labels in ESR imaging or in magnetometry.

The inert carbon free radicals may be prepared from their non-radical precursor compounds by conventional radical generation methods. Suitable non-radical precursor compounds include the corresponding triaryl methanes, triaryl methyl halides and triaryl methanols, and derivatives, e.g. ethers, of the triaryl methanols.

Thus in a further aspect the invention provides a process for the preparation of the novel triarylmethyl radicals of the invention which comprises subjecting a radical precursor therefor to a radical generation step and optionally subsequently modifying the substitution on the aryl moieties, e.g. by oxidation or reduction. By such modification for example sulphide substituents, (e.g. —SCH$_3$ or —SCH$_2$COOEt) may be oxidized to the corresponding sulphones so avoiding problems of acidic hydrogens prior to radical formulation. Similarly lipophilic substituents (such as —SCH$_2$COOEt) may be reduced to corresponding hydrophilic substituents (e.g. —SCH$_2$CH$_2$OH).

Thus by way of illustration the radical-precursor can be represented by formula XXXV

(Ar$^{12}$)$_3$CLv (Lv)    (XXXV)

where Lv is a group displaceable to produce a radical Formula XXXV embrace formulae such as

(Ar$^{12}$)$_3$COH    (II)

(Ar$^{12}$)$_3$CHal    (III)

(Ar$^{12}$)$_3$CH    (IV)

(Ar$^{12}$)$_3$CCOOH    (XXXI)

(Ar$^{12}$)$_3$C.CO.O.O.CO.C(Ar$^{12}$)$_3$    (XXXII)

(Ar$^{12}$)$_3$C.NN C(Ar$^{12}$)$_3$    (XXXIII)

Where Hal represents halogen, e.g. Br or Cl).

Thus for example carbon free radicals may conveniently be prepared from corresponding triaryl methyl halides by reduction with a metal catalyst, such as copper, zinc or silver, or by electrolytic reaction on an electrode or by photochemical reaction in the presence of a chlorine radical scavenger, e.g. an olefin. Alternatively, carbon free radicals may be prepared from the corresponding triaryl methanes by reaction with a base, e.g. in the presence of sodium hydride followed by a reaction with an oxidant, e.g. iodine in the presence of oxygen or a quinone such as chloranil, following for example the method described in U.S. Pat. No. 3,347,941. Another method to prepare triarylmethyl radicals is to react triarylmethanes with other, less stable radicals such as tert-butoxyl radicals. The latter radicals are generated in situ via thermolysis or photolysis of an appropriate precursor, such as a peroxide or an azo compound. A further example of a method by which radical preparation may be effected is reaction of the corresponding triaryl methanols in the presence of an acid to form a carbonium ion followed by reduction to the free radical in the presence of a suitable reducing agent, such as metal ions e.g. Cr$^{2+}$, Fe$^{2+}$, or by electrochemical reduction. The carbon free radicals may also be generated by a comproportionation reaction between cations and anions of a corresponding radical precursor. In such a reaction an electron is exchanged between the anion and the cation, and two radicals are generated. Triarylmethyl radicals may thus be prepared by mixing together a triarylmethyl radical precursor cation with a corresponding anion. Triarylmethyl radicals may also be prepared by thermolysis or photolysis or a corresponding dimeric triarylmethyl structure, for example an azobistriarylmethyl or a bis (triarylmethylcarboxylic acid) peroxide. An alternative method of preparation of triarylmethyl radicals is the electrochemical decarboxylation of a triarylmethylcarboxylate.

While radicals with long half lives in aqueous solution, for example at least one hour, preferably ten days, more preferably fifty days and especially preferably at least one year are clearly particularly desirable for use in in vivo imaging, shorter lived inert free radicals may still be utilised in imaging (e.g. of inanimate samples) and these may particularly conveniently be prepared immediately pre-administration.

The non-radical precursors may themselves be prepared by methods conventional in the art. Thus a process for the preparation of a triaryl methyl radical precursor may comprise one or more of the following steps:

a) (to prepare a triarylmethanol of Formula II

HO—C(Ar$^{12}$)$_3$    (II)

wherein Ar$^{12}$ is as hereinbefore defined) reacting a compound of formula XXIII

H—Ar$^{12}$    (XXIII)

with alkyl lithium (e.g. BuLi) and a compound of formula CO(OR")$_2$ (where R" is an alkyl group, e.g. a C$_{1-9}$ alkyl especially ethyl);

b) (to prepare a triarylmethanol of Formula II

HO—C(Ar$^{12}$)$_3$    (II)

wherein Ar$^{12}$ is as hereinbefore defined)

reacting an organometallic compound comprising a metal linked Ar$^{12}$ moiety (e.g. Ar$^{12}$Li or Ar$^{12}$ MgHal) with a compound of formula XXV, XXVI or XXVII

R"OCOOR"    (XXV)

Ar$^{12}$COOR"    (XXVI)

(Ar$^{12}$)$_2$CO    (XXVII)

where R" is as hereinbefore defined, especially methyl);

c) (to prepare a triarylmethanol of Formula II

HO—C(Ar$^{12}$)$_3$    (II)

wherein Ar$^{12}$ is as hereinbefore defined)
hydrolysing a compound of formula III

Hal—C(Ar$^{12}$)$_3$    (II)

(where Hal and Ar$^{12}$ are as hereinbefore defined);

d) (to prepare a triarylmethanol of Formula II

HO—C(Ar$^{12}$)$_3$    (III)

wherein $Ar^{12}$ is as hereinbefore defined)

reacting a compound of formula XXVII with a compound of formula Hal—$Ar^2$;

e) (to prepare a triarylmethyl halide of Formula III

HO—C($Ar^{12}$)$_3$ (III)

wherein $Ar^{12}$ is as hereinbefore defined)

halogenating a triarylmethane of formula IV

HC($Ar^{12}$)$_3$ (IV)

(e.g. under illumination or by reaction with N-bromosuccinimide or thionyl chloride or by reaction with a tetrahalomethane, e.g. $CCl_4$, in the presence of $AlCl_3$) or halogenating a triarylmethanol of formula II;

f) (to prepare a triarylmethane of formula IV) reacting a compound of formula XXIII with a trialkoxymethane of formula XXVIII

(R"O)$_3$CH (XXVIII)

(where R" is as hereinbefore defined, especially methyl), e.g. in the presence of $AlCl_3$;

g) (to prepare a triarylmethane of formula IV) hydrogenating or otherwise reducing a triarylmethyl halide of formula III or a triarylmethanol of formula II (e.g. using sodium borohydride or trimethylsilylchloride and potassium iodide;

h) (to prepare a triarylmethane of formula IV) reacting a compound of formula XXIII with a compound of formula XXIX ($Ar^{12}$)$_{n_1}$CHHal$_{n_2}$ (XXIX)

(wherein $n_1$ is 0, 1 or 2 and $n_2$ is 1, 2 or 3 and $n_1+n_2$ is 3), e.g. in the presence of $AlCl_3$;

i) (to prepare a triarylmethane of formula IV) reacting a compound of formula XXX

($Ar^{12}$)$_2$CHLv (XXX)

(where Lv is a leaving group, e.g. OTs) with an organometallic compound comprising a metal linked $Ar^{12}$ moiety (e.g. $Ar^{12}$CuLi);

j) (to prepare a triarylacetic acid of formula XXXI

($Ar^{12}$)$_3$CCOOH (XXXI)

(where $Ar^{12}$ is as hereinbefore defined) reacting a triarylmethyl halide of formula III with carbon monoxide (e.g. in the presence of $CO_2(CO)_8$) on a triarylmethyl organometallic compound with carbon dioxide;

k) (to prepare a compound of formula XXXII

($Ar^{12}$)$_3$CCOOOCOC($Ar^{12}$)$_3$ (XXXII)

(where $Ar^{12}$ is as hereinbefore defined) reacting a triarylacetic acid with thionyl chloride and a peroxide, e.g. $H_2O_2$;

l) (to prepare a compound of formula XXXIII ($Ar^{12}$)$_3$CN=NC($Ar^{12}$)$_3$ (XXXIII)

(where $Ar^{12}$ is as hereinbefore defined) oxidizing a triarylmethylamine halide of formula XXXIV

($Ar^{12}$)$_3$CNHHal (XXXIV)

e.g. with silveroxide;

m) reacting a triarylmethyl radical precursor to modify the substitution on one or more of the aryl moieties.

For process step (b), the starting ketone of formula XXVII may be prepared by oxidation, e.g. with $CrO_3$, of the corresponding alcohol ($Ar_{12}$)$_2$CHOH (itself preparable by reaction of the monoaldehyde $Ar^{12}$CHO with an $Ar^{12}$ containing organometallic, e.g. $Ar^{12}$Li or $Ar^{12}$MgHal), or by reaction of such an organometallic with the corresponding carboxylic acid $Ar^{12}$COOH, or by reaction of the acid chloride $Ar^{12}$COCl with $Ar^{12}$H, e.g. in the presence of $AlCl_3$.

For process step (d), the starting material of formula XXXIV may be prepared by reaction of a corresponding triarylmethyl carbanion with $NH_2Cl$ and subsequently with bromate.

The reduction of step (g) may be effected using borane or $LiAlH_4$ and $AlCl_3$.

Triaryl methyl halides may be prepared following the procedures described by Dunnebacke et al. in Chem. Ber. 122:53–535 (1989).

In synthesising substituted triaryl methyl radicals, the substituents may be introduced onto individual $Ar^{12}$ groups before they are trimerized to form the triaryl radical precursor compounds, or they may be introduced directly onto the triaryl precursor compound or the actual radical itself. It is also possible to effect the substitution and trimerization steps simultaneously in a "one-pot" reaction.

The $Ar^{12}$ groups may be prepared by following reaction schemes such as those suggested below

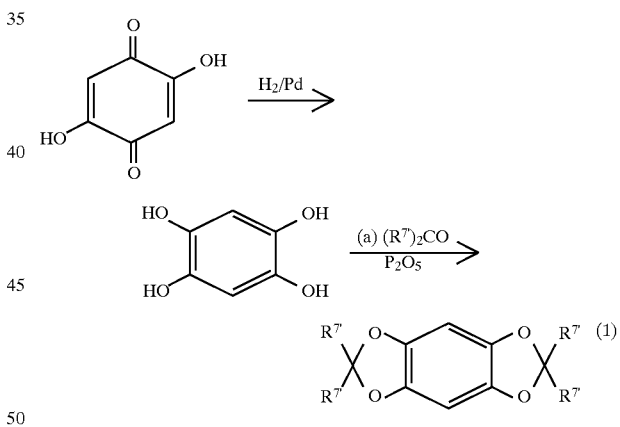

(wherein $R^{7'}$ is a hydrogen atom or a group $R^7$ as hereinbefore defined, optionally protected by a protecting group).

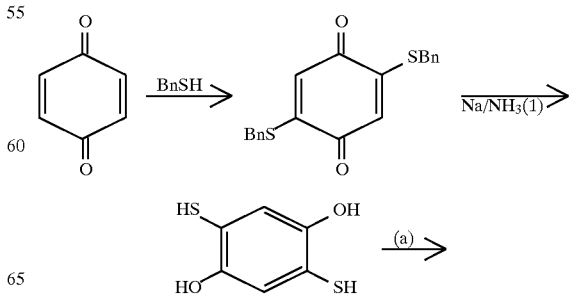

-continued
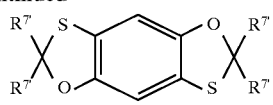
(wherein R⁷' is as defined above)
(3)
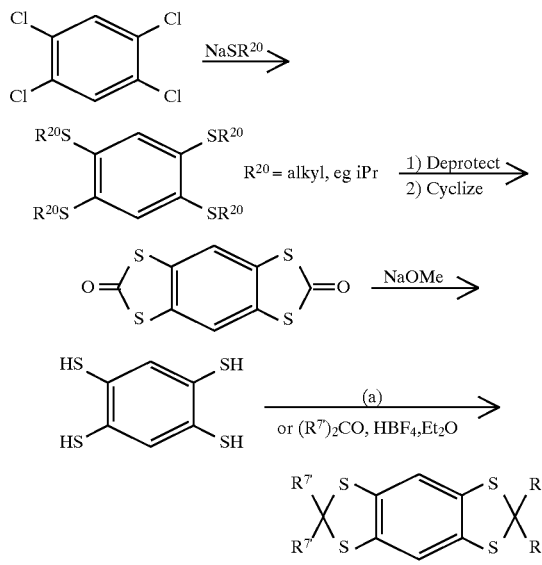
(4)
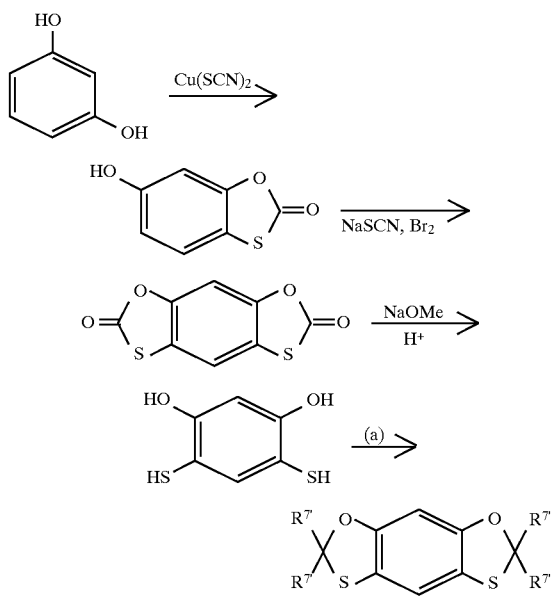
(5)
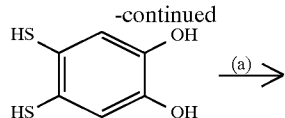
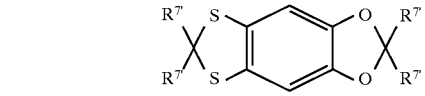
To introduce substituents onto the $Ar^{12}$ groups such as solubilising groups M for example, reaction schemes such as the following may be used
(i)
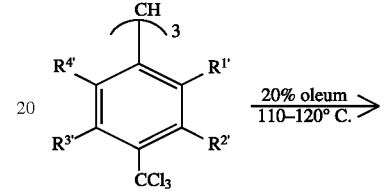
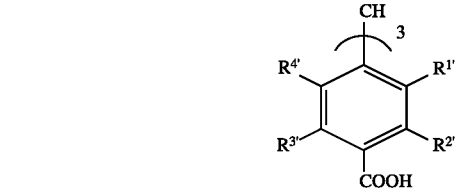
(iia)
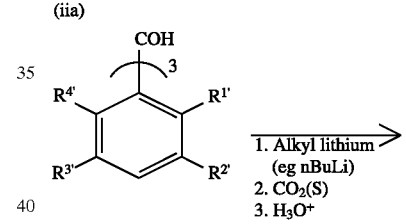
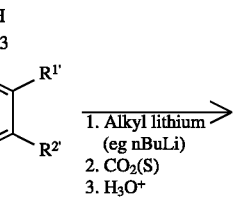
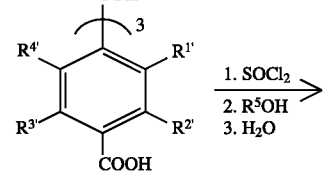
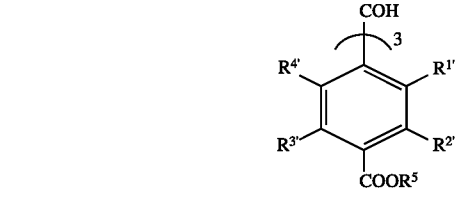
(iib)
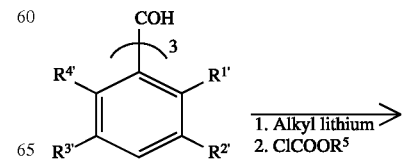

-continued
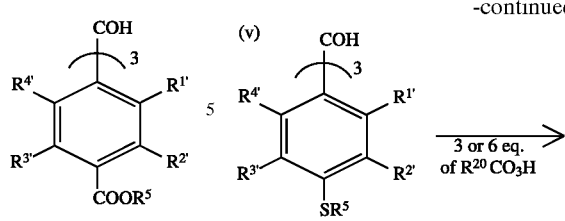
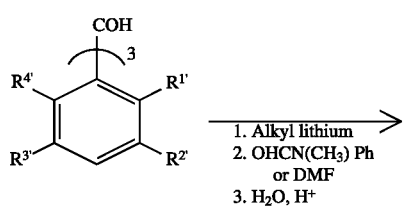
(iii)
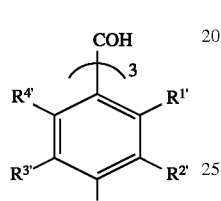
(iva)
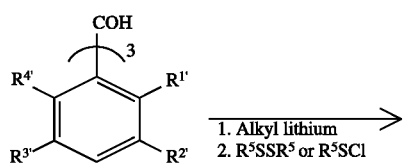
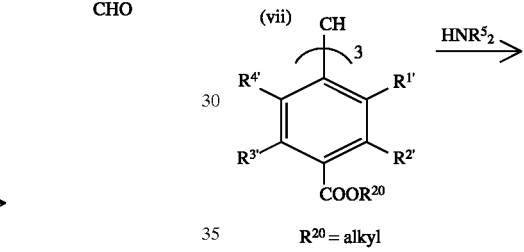
(b)
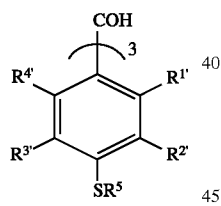
(ivb)
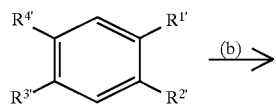
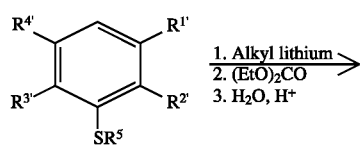
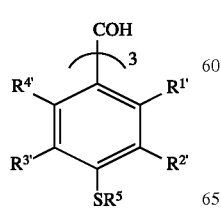
-continued
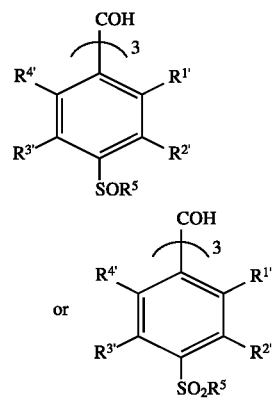
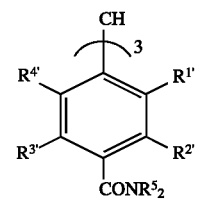
(viii)
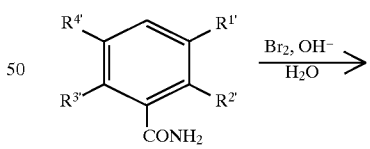
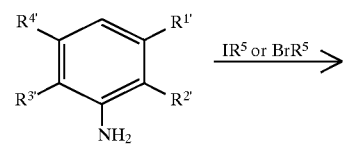
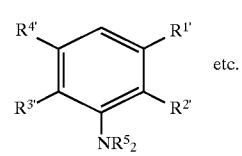
etc.

19
-continued
(ix)
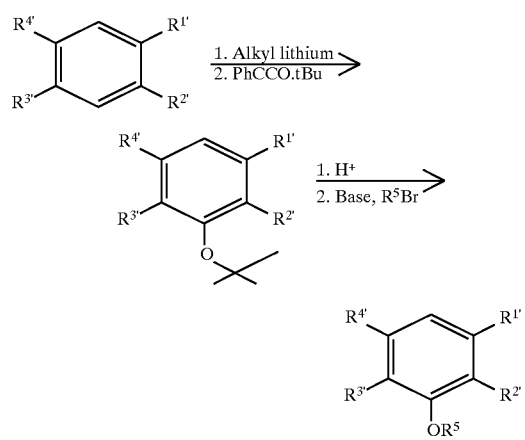
etc.
(x)
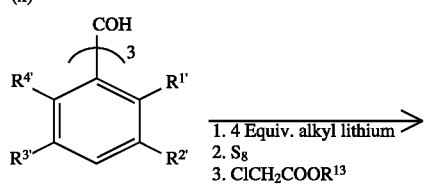
(xi)
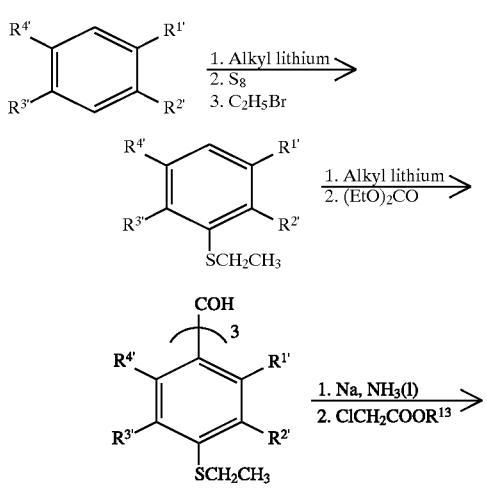
20
-continued
(xii)
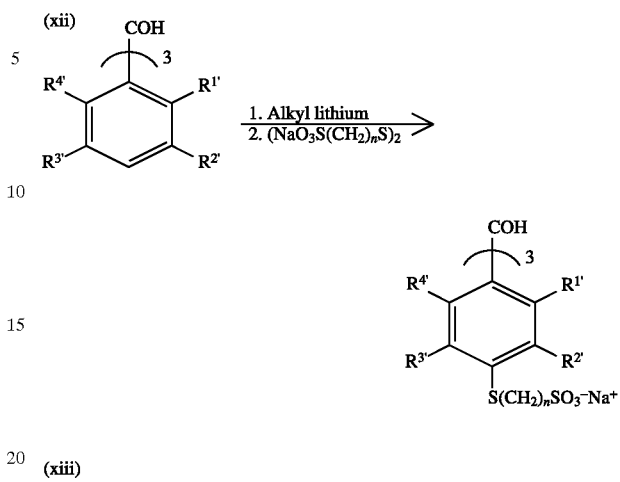
(xiii)
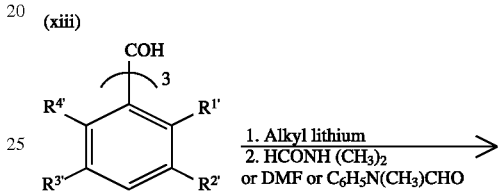
(xiv)
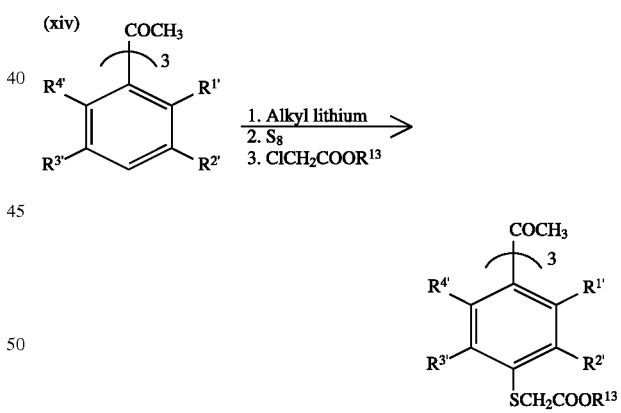
(xv)
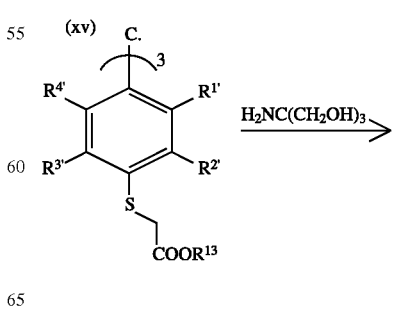

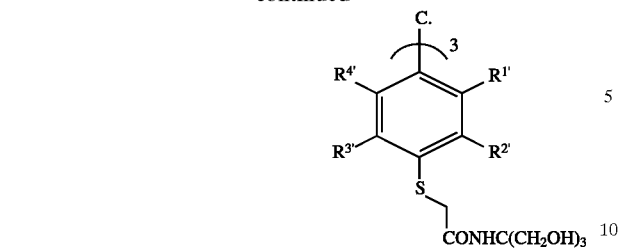
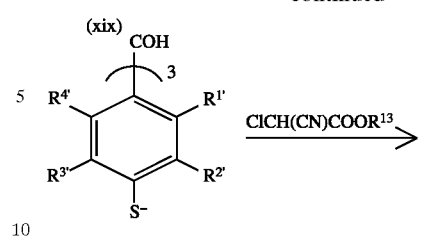
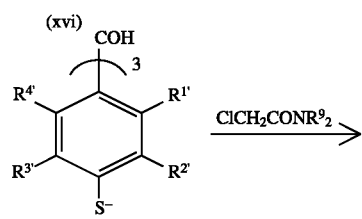
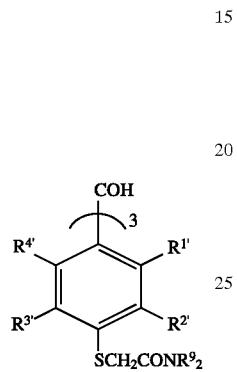
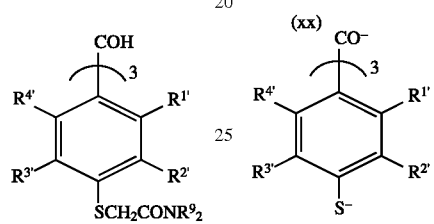
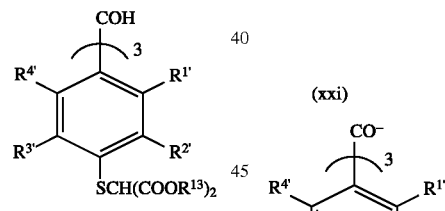
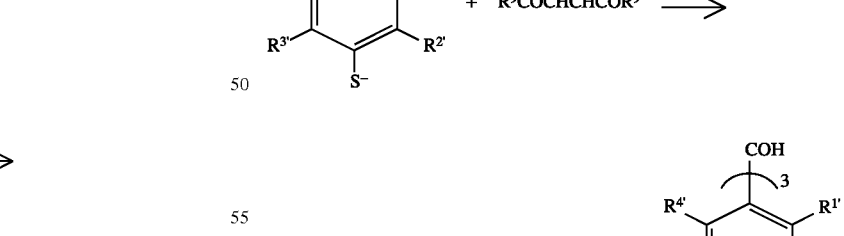
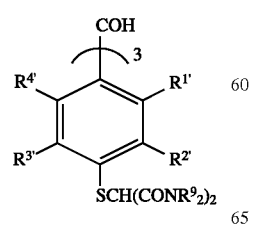

(xxii)

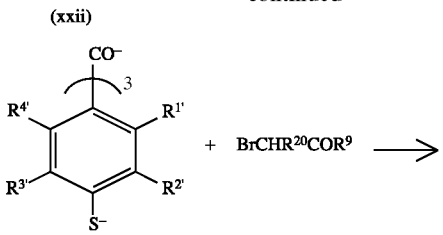

(xxiii)

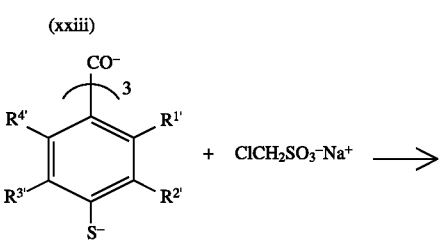

(xxiv)

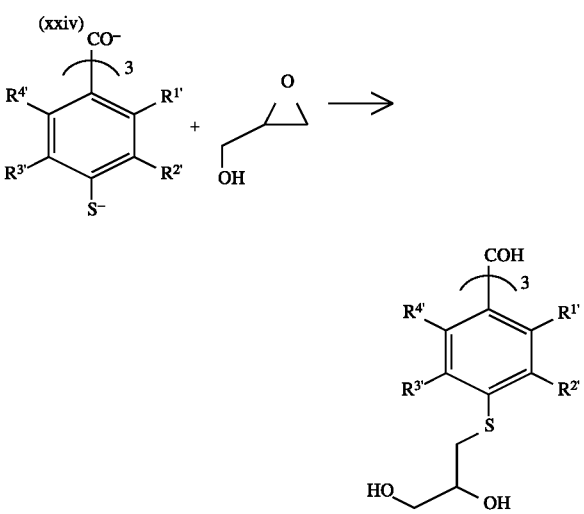

wherein in each of schemes (i) to (xxiv) set out above $R^{1'}$ to $R^{4'}$ are optionally protected groups $R^1$ to $R^4$ and $R^5$ is as hereinbefore defined. Particularly preferably, $R^{1'}$ and $R^{2'}$ and $R^{3'}$ and $R^{4'}$ may represent ring-forming groups —X—$CR^{7'}_2$—X—, e.g. $OC(CH_3)_2O$—.

Similar procedures may be used for the introduction of substitutents onto heterocyclic $Ar^{12}$ groups.

The following are examples of schemes for "one-pot" synthesis of triaryl methyl radical precursors.

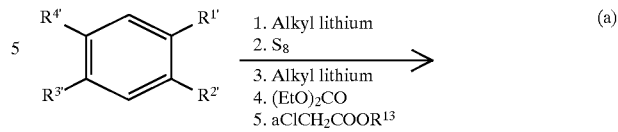

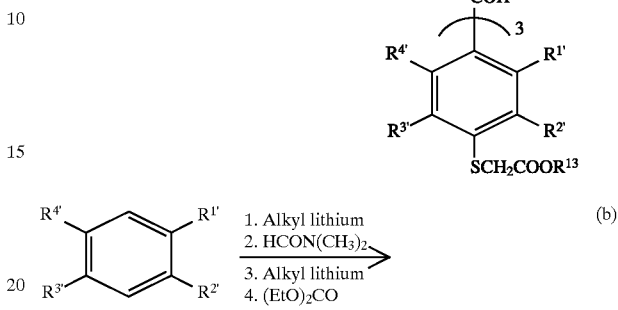

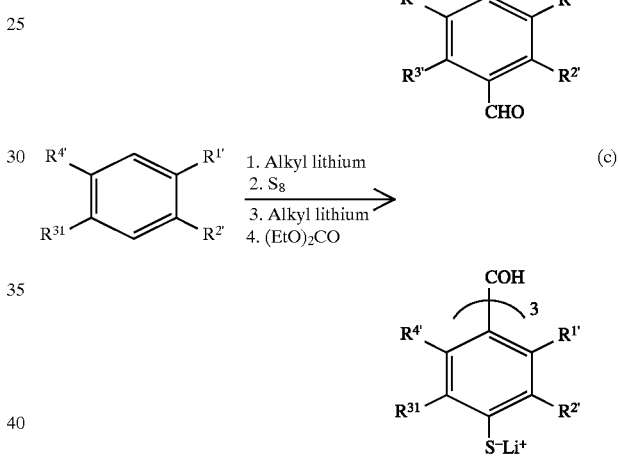

As indicated above, a particularly interesting group of radicals for use according to the invention includes compounds of Formula $.C(Ar^{12})_3$, where one, two or three $Ar^{12}$ groups comprises a central 5–6 membered carbocyclic or heterocyclic aromatic ring bearing two five-membered fused rings, each said fused ring comprising two ring heteroatoms selected from oxygen and sulphur.

The "monomer" and "dimer" compounds, having this structure are particularly useful for the preparation of the radical precursors and thus in a further aspect the invention provides tricylic compound comprising a central 5–6 membered carbocyclic or heterocyclic aromatic ring bearing two five-membered fused rings, each said fused ring comprising two ring heteroatoms selected from oxygen and suphur. Particularly preferred embodiments of such compounds are the compounds of formula XL

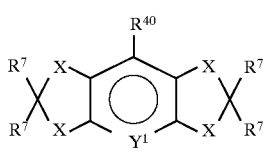

(XL)

(where X and $R^7$ are as hereinbefore defined, $Y^1$ is a group CH, N, $CCOOR^5$, $CSR^5$, CM or CXM, $R^5$ and M are as defined in claim 6 and $R^{40}$ is a hydrogen atom, or a optionally substituted hydroxyl, methyl or formyl group or group

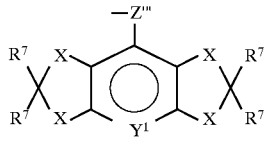 (XL)

where $Z'''$ is CHOH, C=O or CHHal and Hal is a halogen atom), or a salt thereof.

Particularly preferred compounds of formula XL include those wherein each X is oxygen, each $R^7$ is optionally hydroxylated methyl and $Y^1$ is other than N.

The invention also provides, in another aspect, process for the preparation of a compound of formula XL, said process comprising condensing a compound of formula XLI

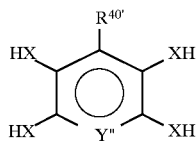 (XLI)

(wherein $R^{40'}$ and $Y''$ are groups $R^{40}$ or $Y_1$ as defined in claim 23 or protected such groups, and X is as defined in claim 23) with a compound of formula $(R^{7'})_2$ CX (where $R^{7'}$ is a group $R^7$ as defined in claim 23 or a protected $R^7$ group) under oxidizing conditions and if necessary removing any protecting groups, optionally after reduction (eg with Fe/HCl) of a compound of formula XLII

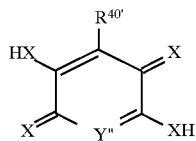 (XLII)

to yield the starting material of formula XLI.

For use in ESREMRI, the inert carbon free radicals are conveniently formulated into contrast media together with conventional pharmaceutical carriers or excipients. Contrast media manufactured or used according to this invention may contain, besides the inert free radicals (or the non-radical precursor where radical formation is to be effected immediately before administration), formulation aids such as are conventional for therapeutic and diagnostic compositions in human or veterinary medicine. Thus the media may for example include solubilizing agents, emulsifiers, viscosity enhancers, buffers, etc. The media may be in forms suitable for parenteral (e.g. intravenous) or enteral (e.g. oral) application, for example for application directly into body cavities having external voidance ducts (such as the gastrointestinal tract, the bladder and the uterus), or for injection or infusion into the cardiovascular system. However solutions, suspensions and dispersions in physiological tolerable media will generally be preferred.

Free radicals which are relatively unstable or insoluble in the sample environment may be encapsulated, e.g. in gastric juice resistant capsules containing a medium in which they are stable. Alternatively, the radical may be presented as an encapsulated freeze dried powder in a soluble capsule. Such formulations might conveniently be dissolved shortly before in vivo use.

For use in in vivo diagnostic imaging, the medium, which preferably will be substantially isotonic, may conveniently be administered at a concentration sufficient to yield a 1 micromolar to 10 mM concentration of the free radical in the imaging zone; however the precise concentration and dosage will of course depend upon a range of factors such as toxicity, the organ targetting ability of the contrast agent, and the administration route. The optimum concentration for the free radical represents a balance between various factors. In general, optimum concentrations would in most cases lie in the range 0.1 to 100 mM, especially 0.2 to 10 mM, more especially 0.5 to 5 mM. Compositions for intravenous administration would preferably contain the free radical in concentrations of 10 to 100 mM especially 50 to 500 mM. For ionic materials, the concentration will particularly preferably be in the range 50 to 200 mM, especially 130 to 170 mM and for non-ionic materials 200 to 400 mM, especially 290 to 330 mM. For imaging of the urinary tract or the renal or biliary system however, compositions may perhaps be used having concentrations of for example 10 to 100 mM for ionic or 20 to 200 mM for non-ionic materials. Moreover for bolus injection the concentration may conveniently be 0.1 to 100 mM, preferably 5 to 25 mM, especially preferably 6 to 15 mM.

BRIEF DESCRIPTION OF DRAWINGS

The accompanying drawing.

Figure 1:
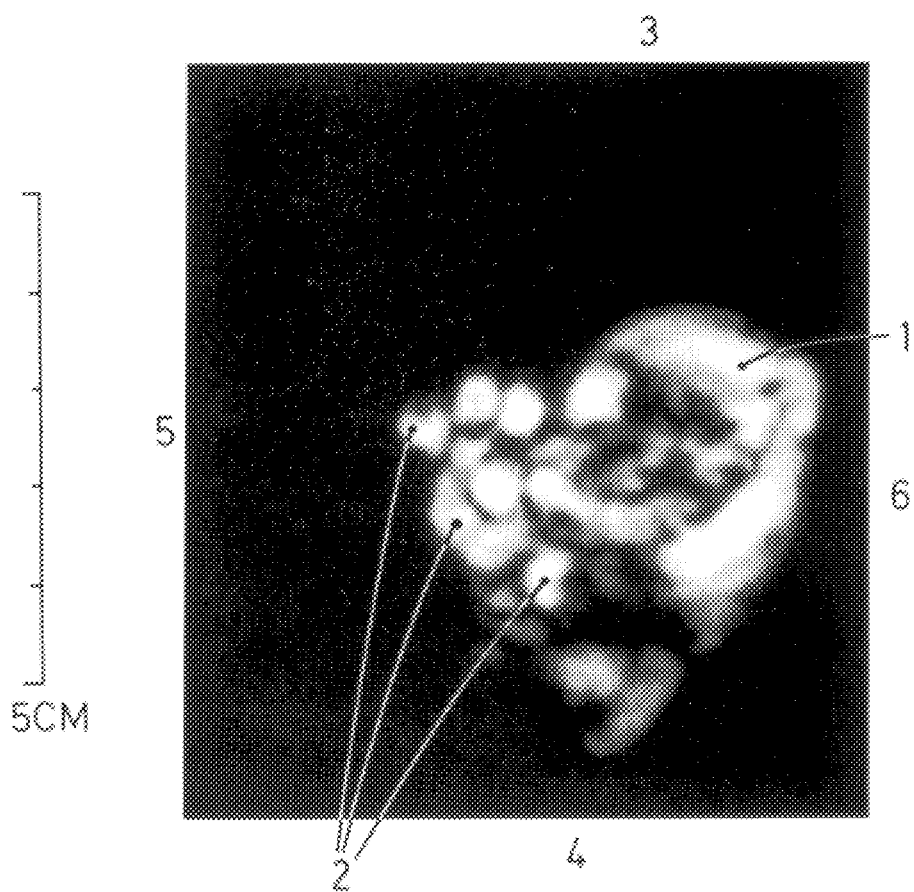
FIG. 1, shows a magnetic resonance image produced according to the invention. Specifically, there is shown a coronal slice through a rat following peroral administration of a contrast medium containing tris(2,2,6,6-tetramethyl sodium-8-carboxylate methylthiobenzo[1,2-d:4,5-d']bis(1,3)dioxole)methyl (the radical of Example 11). The gastrointestinal tract can be seen very clearly In FIG. 1.

1. indicates the stomach;
2. indicates the intestines;
3. indicates the head end of the rat;
4. indicates the tail end of the rat;
5. indicates the right hand side of the rat;
6. indicates the left hand side of the rat.

The image was acquired under the following conditions:
a) TR=0.5 sec, UHF Irradiation Time=0.38 sec. 256 excitations (256×256 matrix). Slice thickness 1 cm. Field of view 25 cm.90° flip angle (SR). Single echo (gradient). TE=30 ms. Single slice. 1. Average.
b) The instrumental parameters were:

Proton frequency 417 kHz (H=100 G) UHF frequency= 274 MHz. The UHF-resonator had a very low loaded $Q \leq 10$ (200 g rat), and a volume of approximately 1 L (diameter 10 cm). The applied UHF power was $\leq 30$ W of which only a small fraction was deposited in the animal (<1/10). The proton coil had a diameter of 126 cm and thus a very low filling factor when loaded with a rat (5 cm). The Q factor of this coil was high (>1000), but loaded with both UHF-resonator and animal decreased to below 500.
c) The signal/noise (S/N) ratio was approximately 100.

The perorally applied volume of contrast medium was approxmiately 5 ml and the concentration of radical was less than 0.5 mM.

In the unenhanced image, where no contrast medium was administratired, the S/N ratio was −3 resulting in an image where no details could be distinguished from the background noise.

The present invention will now be further illustrated by the following non-limiting Examples (percentages, parts and ratios are by weight and temperatures are in degrees Celsius unless otherwise stated).

EXAMPLE 1

2,5-Dimercapto-1,4-dihydroxybenzene

Ammonia was condensed (ca 200 ml) into 150 ml of dry diethylether in a 3-necked flask, with external cooling. Then 9.0 g (0.0256 mole) of 2,5-dibenzylmercapto-p-benzoquinone was dissolved into the liquid. Sodium (5.9 g, 0.256 mole) cut into fine pieces was added portionwise with efficient stirring. After stirring for an additional 2.5 hours, abs. ethanol (20 ml) was added and the ammonia was evaporated. Water (170 ml) was added to the reaction product and it was extracted with 2×30 ml of ether. The aqueous phase was then acidified to pH 1–2, with conc. hydrochloric acid, and extracted with 3×80 ml of ether. The ether extracts were collected, dried ($Na_2SO_4$), the solvent evaporated leaving a fluffy light brown glistening residue, 4.3 g (90%).

MS (Silated Product): M/e 462 (42% $M^+$) 447 (5% $M^+$–15)

EXAMPLE 2

2,2,6,6-Tetramethylbenzo[1.2-d:4,5-d']bis(1,3) dithiole

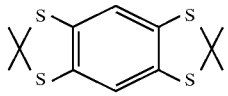

1,3,5,7-Tetrathia-S-indacene-2,6-dione (4.0 g, 0.016 mole, prepared according to Larsen and Bechgaard J. Org Chem 52: 3287 (1987)) was suspended in 60 ml of a 1M solution of sodium methoxide in methanol. Stirring was maintained for ½ hour at ambient temp. until a clear solution was formed. The reaction mixture was then evaporated to dryness and the residue acidified with 5N hydrochloric acid to pH 1. The aqueous phase was extracted with 3×70 ml of methylene chloride. The organic phases were dried ($Na_2SO_4$), the solvent evaporated leaving a light tan coloured crystalline residue. This was suspended in 50 ml of dry toluene, and 3 ml of acetone and 2.5 ml of fluoroboric acid etherate ($HBF_4 \cdot Et_2O$) were added. The mixture was stirred at ambient temperature for 5 hours then refluxed over night. The reaction mixture was then poured into 100 ml of cold saturated sodium hydrogen carbonate solution. The phases were separated and the organic phase was washed with 30 ml of water. The aqueous phases were back-extracted with 40 ml of methylene chloride. The organic phases were collected, dried ($Na_2SO_4$) and the solvent evaporated leaving a light yellow cryst. residue, 4.1 g (92%). IR(film): 2960,2920 $CM^{-1}$, 1H-NMR ($CDCl_3$) δ: 1.88 ($CH_3$ 12H), 7.02 (arom H, 2H) ppm MS: m/e 286 (14% $M^+$)

EXAMPLE 3

Tris(benzo[1,2-d:4,5-d']bis(1,3)dioxole-4-yl) methanol

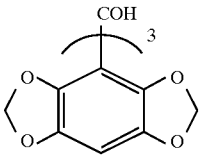

3.2 g Benzo[1,2-d: 4,5-d']bis(1,3)dioxole prepared according to F. Dallacker et al. Liebigs Ann. Chem. 725, 99–105 (1969) (0.019 mole) was dissolved in 100 ml dry ether under Argon. After cooling in ice-acetone to 15° C., 10 ml 2.5M butyllithium in hexanes (Aldrich) was added from a syringe. The cooling bath was removed and the mixture was stirred for 2 hours. 0.8 ml diethylcarbonate (0.0068 mole) was added with a slig increase in temperature and color change to yellow-brown. The mixture was stirred at room temperature overnight and then poured over 150 ml ice-water and extracted with 3×75 ml $CH_2Cl_2$. The organic phase was washed with 100 ml water, dried over $MgSO_4$ and evaporated to dryness to yield 2.96 g (88%) m; 125° C. (unsharp).

$^1$H-NMR ($CDCl_3$) δ: 5.75 ($CH_2$, 12H); 6.25 (Arom H, 3H) ppm

MS: m/e 524 (100% $M^+$)

The corresponding radical showed a linewidth of 500 mG in its ESR spectrum and an Overhauser enhancement of 8 at 5 hr UHF power.

EXAMPLE 4

1,2,4,5-Tetrahydroxybenzene[1,2-d:4,5-d']bis(1,3) dioxole 14 g 2.5-dihydroxy-1,4-benzoquinone (0.10 mole) was suspended in 100 ml 96% ethanol. 0.1 g 10% Pd on C was added under $N_2$ and reduced at 40 Psig in a Parr apparatus (in the usual manner) until 0.10 mole $H_2$ was absorbed. The dark reaction mixture was filtered to remove the catalyst and evaporated to dryness to afford the product in quantitative yield.

EXAMPLE 5

2,2,6,6-Tetramethylbenzo[1,2-d:4,5-d']bis(1,3) dioxole

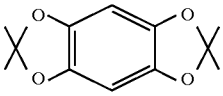

18.6 g of the 1,2,4,5-tetrahydroxybenzene prepared according to Example 4 (0.13 mole) and 70 ml acetone (58.6 g, 1.0 mole) was dissolved in 1 1 tetrahydrofuran. 168 g $P_2O_5$ (1.18 mole) was added to the vigorously stirred mixture in portions as fast as possible. The mixture was heated to reflux for 4 hours. After cooling to room temperature the solids were filtered with suction and washed with 0.5 L ether. The combined filtrates were treated with 10 g $K_2CO_3$ and stirred 1 hour, filtered and evaporated to dryness yielding a yellow-brown oily solid. The product was triturated with petroleum ether, decanted and evaporated to yield 13.8 g of the title compound (48%) as white-yellow crystals, mp=122° C., which can be recrystalized from a small amount of petroleum ether.

$^1$H NMR (CDCl$_3$) δ: 1.65 (CH$_3$, 12H); 6.75 (Arom H, 2H) ppm $^{13}$C NMR δ: 25.49 (CH$_3$); 92.75 (Arom CH); 117.81 (CMe$_2$); 140.43 (Arom C) ppm MS: m/e 222 (90% M$^+$), 207 (100%, M$^+$−15)

EXAMPLE 6

3-Methylthio-2,2,6,6-tetramethylbenzo[1,2-d:4,5-d'] bis(1,3)dioxole

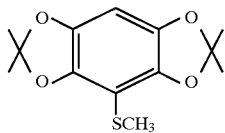

1.1 g of 2,2,6,6,-tetramethylbenzo(1,2-d:4,5-d']bis(1,3) dioxole prepared according to Example 5 (0.005 mole) was dissolved in 25 ml dry ether under argon and treated with 2.2 ml 2.5M butyllithium in hexane, at room temperature. After 1 hour 0.52 g dimethyldisulfide (0.0055 mole) was added and the mixture stirred overnight at room temp. The reaction mixture was then poured into 50 ml ice-water. The phases were separated and the water phase extracted with 50 ml ether. The combined organic phase was washed with 50 ml 2M NaOH, dried over MgSO$_4$ and evaporated to yield 1.1 g (82%) as white crystals, mp=108° C., which can be recrystallized from a small amount of methanol.

$^1$H NMR (CDCl$_3$) δ: 1.67 (CH$_3$; 12H); 2.45 (—SCH$_2$, 3H) 6.26 (Arom CH,1H)

EXAMPLE 7

Tris(8-Methylthio-2,2,6,6-tetramethylbenzo[1,2-d:4, 5-d']bis(1,3)dioxole)methanol

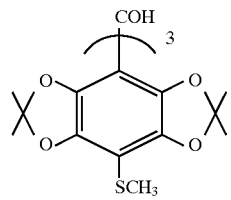

6.2 g 3-methylthio-2,2,6,6-tetramethylbenzo[1,2-d:4,5-d'] bis(1,3)-dioxole prepared according to Example 6 (0.0235 mole) was dissolved in 150 ml dry ether under argon. The solution was cooled in an ice-methanol bath, while 10 ml 2.5M butyllithium in hexane (0.025 mole) was added and then left with stirring at room temperature for one hour. 0.95 ml diethylcarbonate (0.0078 mole) was added.

After 18 hours the reaction mixture was poured over 200 ml ice-water and the product extracted with 3×75 ml CH$_2$Cl$_2$. The organic phase was washed with 100 ml H$_2$O, dried over MgSO$_4$ and evaporated to dryness, yielding ca 5 g yellow solid. The product was triturated with a little cold petroleum ether and filtered to yield 2.1 g of the title compound (32%) as yellow crystals, mp>260° C.

$^1$H NMR (CDCl$_3$) δ: 1.51 (CH$_3$, 36H); 2.40 (SCH$_3$, 9H); 4.20 (OH,1H) ppm $^{13}$C-NMR δ: 17.28; 25.48; 72.56; 99.87, 111.97 138.71; 140.97.

MS: m/e 830 (80% M$^+$), 714 (100% M$^+$−116)

EXAMPLE 8

Tris(8-methylthio-2,2,6,6-tetramethylbenzo[1,2-d:4, 5-d']-bis(1,3)dioxole)methyl

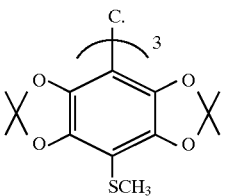

250 mg Tris-(3-methylthio-2,2,6,6-tetramethylbenzo[1,2-d:4,5-d']bis(1,3)dioxole)methanol (0.3 mmol, Example 7) was dissolved in 50 ml dry THF (Al$_2$O$_3$, super I, basic) under Argon. 0.5 g CrCl$_2$ and then 0.5 ml BF$_3$ etherate was added to the vigorously stirred mixture. After 15 minutes the reaction mixture was poured over 50 ml 4M NaOH. The organic phase was separated and filtered through a short column of SiO$_2$ and eluted with dry ether. The dark violet solution was evaporated to dryness yielding 176 mg (71%) of the title compound as a black powder. A solution of this material in tetrahydrofuran was shown to contain 41% radical according to the method of Evans (J. Chem. Soc. 2003 (1959)).

MS: m/e 814 (60% M$^+$−1)

EXAMPLE 9

Tris(8-ethoxycarbonylmethylthio-2,2,6,6-tetramethylbenzo[1,2-d:4,5-d']bis(1,3)dioxole) methanol

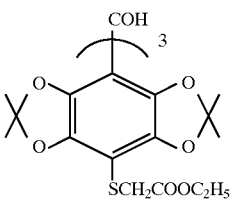

2.25 g (0.010 mole) of the benzobisdioxole of Example 5 in 50 ml tetrahydrofuran (THF, HPLC-grade) was cooled to −80° in an dry ice-acetone bath. 4.4 ml (1.1 eqv) 2.5M n-butyl lithium was added and the mixture allowed to come to ambient temperature. After about 15 minutes 0.35 g of sulphur (S$_8$) was added in one portion. After about 20 minutes the sulphur had reacted and the brownish solution was cooled to −80° C. and treated with 4.4 mL 2.5M n-butyl lithium. The cooling bath was removed and the temperature allowed to rise again to ambient temperature. After about 20 minutes a cloudy suspension was obtained. 0.4 mL diethylcarbonate was added.

After 1 hour, 5.5 ml (0.05 mole) of chloroacetic acid ethylester was added in one portion (slight heat formation). The reaction mixture become very dark and homogeneous. TLC in CHCl$_3$ showed that a "trimer" was formed along with dimeric ketones (and other products). After another ½ hour the reaction mixture was poured into 200 mL ice-water and extracted with 3×75 mL diethyl ether. The organic phase was washed with 2×50 mL H$_2$O, dried over MgSO$_4$ and evaporated to dryness yielding an orange oil it was separated on silica with CHCl$_3$-diethyl ether as eluent.

Evaporation of the solvent yielded 1.46 g orange oil (very viscous) yield: 42%. The product was verified using $^1$H NMR, $^{13}$C NMR and mass spectrometry.

$^1$H NMR (CDCl$_3$) δ: 1.22 (t) (CH$_3$,9H); 1.50 (CH$_3$,36H), 3.57 (CH$_2$,6H); 4.1 (CH$_2$,6H) ppm $^{13}$CNMR δ: 14.10; 25.44; 35.49; 61.22; 96.64; 112.45, 117.77, 138.67, 141.25, 169.016 ppm MS m/e 1407 (10%, M+1), 1031 (30% M$^+$–15)

EXAMPLE 10

Tris(8-ethoxycarbonylmethylthio-2,2,6,6-tetramethylbenzo[1,2-d:4,5-d']bis(1,3)dioxole) methyl

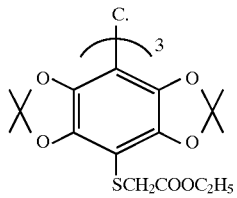

250 mg of tris(8-ethoxycarbonylmethylthio-2,2,6,6-tetramethylbenzo[1,2-d:4,5-d']bis(1,3)dioxole)methanol prepared according to Example 9 was dissolved in about 100 mL THF (HPLC-grade) and placed in a 250 mL separating funnel. A rapid stream of argon was bubbled through the solution. 200 mg CrCl$_2$ was added followed by 0.4 mL BF$_3$-diethylether. After 5 minutes 75 mL diethylether was added and then the mixture was extracted with 2×75 ml H$_2$O and 1×75 ml 2M NaOH. The dark organic phase was filtered through 5cm SiO$_2$, eluted with diethylether and evaporated to dryness in vacuo affording a black-brown oil that slowly solidified on addition of 5 ml methanol 177 mg black crystals were obtained, and washed with petroleum ether.

Radical content: 60% (NMR—Evans method)

ESR 0.2 mM in Toluene: 7 lines A$_{CH2}$: 66 Milli Gauss linewidth: 33 Milli Gauss

EXAMPLE 11

Tris(2,2,6,6-tetramethyl sodium-8-carboxylatemethylthiobenzo[1,2-d:4,5-d']bis(1,3) dioxole)methyl

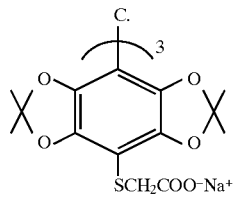

70 mg of tris(8-ethoxycarbonylmethylthio-2,2,6,6-tetramethylbenzo[1,2-d:4,5-d']bis(1,3)dioxole)methyl prepared according to Example 10 in 2 mL methanol, 120 μL NaOH/H$_2$O (0.019 g NaOH) were sonicated for 0.5 hr. A test sample (few drops) was diluted in H$_2$O and diethylether was added. No color appeared in the etheric phase. The hydrolysis mixture was evaporated to dryness yielding 53 mg of the title product.

EXAMPLE 12

Tris(8-methoxycarbonylmethylthio-2,2,6,6-tetramethylbenzo[1,2-d:4,5-d']bis(1,3)dioxole) methanol

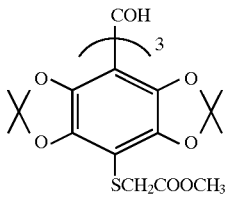

11.38 g of the benzobisdioxole of Example 5 (0.051 mole) was dissolved in 250 ml HPLC grade tetrahydrofuran under argon and cooled to –45° C. in dry ice. 26.2 mL n-butyl lithium (0.055 mole) 2.1M, was added from a syringe over about 1 minute. The temperature rose to –30° C., the cooling bath was removed and the mixture was left with stirring for 30 min. It was cooled to –30° and 1.75 g S$_8$ was added in one portion. The cooling bath was removed and after 35 minutes the temperature had risen to 0° C. and all the sulphur had reacted. The mixture was cooled to –40° and 26.2 ml n-butyl lithium was added in one portion. The cooling bath was removed and a slightly colored suspension was formed just above 0° C. After 1 hour the temperature has risen to 15° C. and a white suspension had formed, which was then cooled to –20° C. and 2 mL diethylcarbonate was added. The mixture changed color from yellow through green to brown and the cooling bath was removed. After 1 hour the temperature had risen to –20° C., was again cooled to –10° C. and 10 mL chloro-acetic acid methyl ether was added (exothermic). The cooling bath was removed and the mixture become homogeneous and very dark. After ½ hour the reaction mixture was poured into ice-water (500 ml) and 20 mL acetic acid added. 300 mL diethyl ether was added and the phases were separated. The water phase was extracted with additional diethyl ether. The organic phase was stirred for 15 minutes with 10 g K$_2$CO$_3$(anhydrous), decanted and washed with two lots of 200 mL H$_2$O, dried over MgSO$_4$ and evaporated. It was then separated on a "TLC-SiO$_2$"-column with CHCl$_3$/CH$_2$Cl-$_2$/diethylether. Fraction 3 (the diethylether-phase) contained 9.6 g of the product (57%). It was crystallized from cyclohexane to yield 2.5 g yellow crystalline powder.

$^1$H NMR (CDCl$_3$) δ: 1.485 (CH$_3$, 36H); 3.65 (OCH$_3$; 9H); 3.54 (CH$_2$ 6H)ppm $^{13}$C NMR: 25.25, 35.31, 52.23; 72.41; 96.43, 112.42, 117.71, 138.57; 141.22; 169.43.

MS M/e 1004 (70% M$^+$); 988 (50% M$^+$–16)

EXAMPLE 13

Tris(8-methoxycarbonylmethylthio-2,2,6,6-tetramethylbenzo[1,2-d:4,5-d']bis(1,3)dioxole)methyl

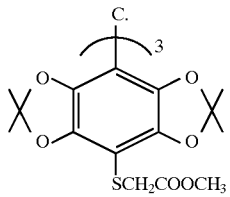

1.0 g of tris(8-methoxycarbonylmethylthio-2,2,6,6,-tetramethylbenzo[1,2-d:4,5-d']bis(1,3)dioxole)methanol prepared according to Example 12 was dissolved in 150 mL THF (HPLC-grade) in a separating funnel. 1.0 g $CrCl_2$ (anhydrous) was added and a rapid stream of argon was passed through the solution. 2 mL $BF_3$/diethylether was added followed by diethylether after 10 min. Inorganic salts were extracted with $H_2O$ and 2M NaOH. The organic phase was filtered through a short column of $SiO_2$ and exaporated to a brown-black oil. It was taken up in about 20 mL methanol and precipitated with a half volume of $H_2O$, filtered and dried in vacuum to yield 0.78 g of a black brown powder.

EXAMPLE 14

Tris(8-mercapto-2,2,6,6-tetramethylbenzo[1,2-d:4,5-d:4,5-d']bis(1,3)dioxole)methanol

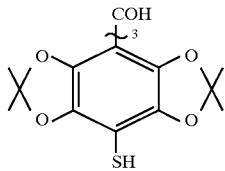

4.5 g of the benzobisdioxole of Example 5 were dissolved (under $N_2$) in about 100 ml THF (HPLC-grade) and cooled to −78° C. in dry-ice acetone bath, 85 ml 2.5 m butyllithium (BuLi) (in hexane) was added. A transient color change to red was observed with the first drops of BuLi, but almost immediately the color changed to very pale yellow. The cooling-bath was removed. After 20 minutes the reaction mixture was temporarily coooled and 0.64 g $S_8$ (powder) was added in one portion. The cooling bath was removed and the color changed to light yellow as the particles of sulphur reacted just below 0° C. The reaction mixture was left to stand with stirring at ambient temperature for an additional 30 minutes. After cooling to −78° C., 2.5 ml BuLi 2.5 m) was added. After stirring for 1 hour at room temperature a white, thin, slurry had formed. It was cooled to −78° C. and 0.81 ml diethylcarbonate was added slowly. The mixture was left to stir at ambient temperature and the white suspension thickened and changed colour from yellow to brown.

After 1.5 hours the reaction mixture was poured into 100 ml diethylether with about 30 g $NaH_2PO_4$ saturated with $N_2$. The phases were separated and the $H_2O$-phase was extracted once with 100 ml diethylether. The combined organic phase was washed once with $H_2O$ with about 15 g $NaH_2PO_4$, dried over $MgSO_4$, filtered and evaporated in vacuo to yield 5.0 g voluminous semi solid. The product was taken up in approximately 20 ml diethylether and slowly precipitated with heptane, filtered off and dried in vac. to afford 4.55 g yellow powder. It was purified on TLC-silica 60M (Merck). 1 g material was dissolved in 20 ml diethylether applied to a flash column (400 ml $SiO_2$ in diethylether-heptane (7:3) and eluted with diethylether until the first yellow band appeared, yielding 0.20 g of a nearly colorless yellow crystalline solid.

$^1$H NMR ($CDCl_3$) δ: 1.49 ($CH_3$), 3.25 (SH), 4.10 (OH)

$^{13}$C NMR δ: 25.48, 72.33, 93.55, 110.66, 117.51, 138.26 and 138.54.

EXAMPLE 15

Tris(8-methoxycarbonyl-2,2,6,6-tetramethylbenzo[1,2-d:4,5-d']bis(1,3)dioxole-4-yl)methanol

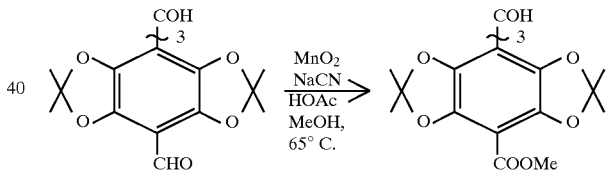

Tris(8-formyl-2,2,6,6-tetramethylbenzo[1,2-d:4,5-d]-bis(1,3)dioxole-4-yl)methanol (1.26 g, 1.62 mmol (prepared by reaction of tris(2,2,6,6-tetramethylbenzo[1,2-d:4,5-d']bis(1,3)dioxol-4-yl)methanol (See Example 44) with nBuLi in DMF)) was dissolved in dry MeOH (80 mL). To this solution was added $MnO_2$ (18.9 g, 217 mmol), NaCN (1.26 g, 25.7 mmol) and acetic acid (HOAc) (1.26 mL). The reaction mixture was heated to 65° C. for 40 h and was then filtered through Celite and the filtrate was evaporated to dryness. The residue was partitioned between $CH_2Cl_2$ (100 mL) and water (40 mL). The organic phase was washed with another 2×30 mL of water, the organic phase was separated, dried ($Na_2SO_4$) and the solvent was evaporated to yield a yellow to brown residue, which was further pumped to dryness. The residual foam was chromatographed on a column packed with $SiO_2$, eluting with $CH_2Cl_2/Et_2O$ (4:1). The fractions containing pure product were collected and the solvent was evaporated to yield 1.1 g (77%) of pure tris(8-methoxycarbonyl-2,2,6,6-tetramethylbenzo[1,2-d:4,5-d']bis(1,3)dioxole-4-yl)methanol.

¹H NMR (CDCl₃, 300 MHz) δ: 1.44 (CH₃, 36H, s), 3.78 (OCH₃, 9H, s), 4.24 (OH, 1H, s).

¹³C NMR (CDCl₃, 75 MHz) δ: 163.4 (C=O), 140.5 139.2 (aromatic C—O), 118.3 (alifatic O—C—O), 115.0 (quart. C-subst. aromatic), 99.1 (quart. p-C-subst. aromatic), 72.6 (quart. alifatic C—OH), 51.9 (OCH₃), 25.5 (CH₃).

MS (Thermospray): M⁺+23 (Na) 888, 889.

EXAMPLE 16

Tris(8-carboxyl-2,2,6,6-tetramethylbenzo[1,2-d:4,5-d']bis(1,3)dioxole-4-yl)methanol

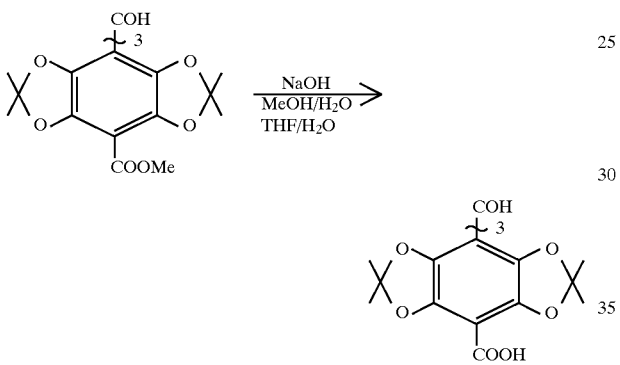

The ester of Example 15, tris(8-methoxycarbonyl-2,2,6,6-tetramethyl-benzo[1,2-d:4,5-d']bis(1,3)dioxole-4-yl)methanol (0.30 g, 0.34 mmol) was dissolved in MeOH (10 mL), and NaOH (0.041 g, 1.02 mmol) dissolved in MeOH/H₂O (2.32M NaOH solution) was added until pH reached 7. In total 0.44 mL of the basic solution was used. The MeOH was evaporated in vacuum due to solubility problems and THF (3.5 mL) was added. The reaction mixture cleared with this treatment. After 12 h the reaction mixture was turbid and a precipitate had formed. This precipitate dissolved with the addition of water (10 mL). The THF was evaporated under reduced pressure and water (10 mL) was added and the aqueous phase was extracted with ether (10 mL). The organic phase was separated and the aqueous phase was acidified (pH 3.5) with 2M HCl. A yellow precipitate was formed and the aqueous phase was extracted with ether (3×20 mL) and CH₂Cl₂ (30 mL). The organic phases were collected, dried (Na₂SO₄) and the solvent was evaporated to yield the product tris(8-carboxy-2,2,6,6-tetramethyl-benzo[1,2-d:4,5-d']bis(1,3)dioxole-4-yl)methanol as a slightly tanned residue (0.25 g, 87%). The product contained a small impurity (appreciated to about 2% at the same extinction) according to HPLC (C18, ion pair (tetrabutyl-ammonium acetate) chromatography, CH₃CN:H₂O) with UV (254 nm) detection.

¹H NMR (D₂O, 300 MHz) δ: 1.26 (CH₃, 36H, s).

¹³C NMR (D₂O, 300 MHz) δ: 169.6 (C=O), 138.9 138.8 (aromatic C—O), 118.2 (alifatic O—C—O), 111.9 (quart. C-subst. aromatic), 105.9 (quart. p-C-subst. aromatic), 72.1 (quart. alifatic C—OH), 24.6 (CH₃).

IR (KBr, cm-1): 3450 (OH-stretching broad), 1670 (C=O stretching s).

EXAMPLE 17

Tris(2,2,6,6-tetramethyl-benzo[1,2-d:4,5-d']bis(1,3)-dioxole-4-yl)methane

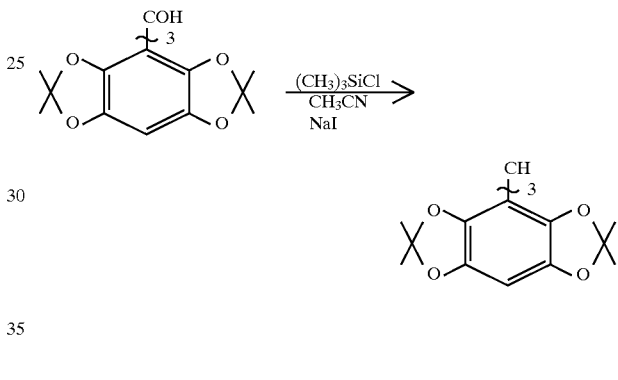

Trimethylsilyl chloride (68.1 mL, 539 mmol) and sodium iodide (81.0 g, 540 mmol) were mixed in acetonitrile (500 mL), and tris(2,2,6,6-tetramethylbenzo[1,2-d:4,5-d']-bis(1,3)dioxole-4-yl)methanol (62.4 g, 90.2 mmol, Example 44) and was added with efficient stirring at room temperature. The reaction flask was surrounded with aluminum foil to prevent light to enter. After stirring for 24 h, the reaction mixture was poured into 2 L of a Na₂S₂O₃ solution (70 g of Na₂S₂O₃×5H₂O in 2 L of water). A yellow precipitate was formed, filtered off and was left to dry on the filter under suction (2 h). The product was triturated with i-PrOH twice, filtered and washed with cold diisopropyl ether (15 mL) to yield 54.1 g (88%) of the product tris(2,2,6,6-tetramethyl-benzo[1,2-d:4,5-d']bis(1,3)dioxole-4-yl)methane.

¹H NMR (CDCl₃, 300 MHz) δ: 1.47 (CH₃, ₃₆H, s), 5.42 (CH, 1H, q, J=0.37 Hz), 6.20 (aromatic H, 3H, d, J=0.37 Hz).

¹³C NMR (CDCl₃, 75 MHz) δ: 139.5 139.8 (aromatic C—O), 116.7 (alifatic O—C—O), 107.6 (quart. aromatic), 90.7 (aromatic C—H), 30.7 (C—H), 25.3 (CH₃).

MS (EI): M⁺-16 (676, 100%), M⁺-15 (678, 40%), 338.5 (70%).

EXAMPLE 18

Tris(8-carboxyl-2,2,6,6-tetramethyl-benzo[1,2-d:4,5-d']bis(1,3)dioxole-4-yl)methane and bis(8-carboxyl-2,2,6,6-tetramethyl-benzo[1,2-d:4,5-d']-bis(1,3)dioxole-4-yl)-(2,2,6,6-tetramethyl-benzo[1,2-d:4,5-d']-bis(1,3)dioxole-4-yl)methane

EXAMPLE 19

Tris(8-methoxycarbonyl-2,2,6,6-tetramethyl-benzo[1,2-d:4,5-d']-bis(1,3)dioxole-4-yl)methane and bis(8-methoxycarbonyl-2,2,6,6-tetramethyl-benzo[1,2-d:4,5-d']-bis(1,3)dioxole-4-yl)-(2,2,6,6-tetramethyl-benzo[1,2-d:4,5-d']-bis(1,3)dioxole-4-yl)methane

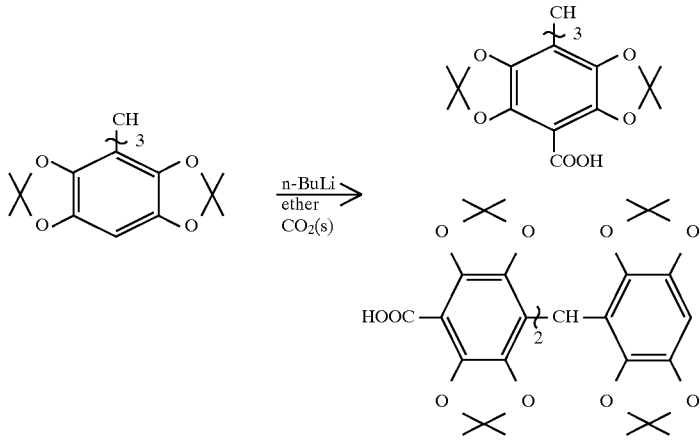

Tris(2,2,6,6-tetramethyl-benzo[1,2-d:4,5-d']bis(1,3)dioxole-4-yl)methane (1.65 g, 0.244 mmol, Example 17) was dissolved in dry diethyl ether (150 mL) n-BuLi (5.86 mL, 2.5M in toluene, 1.465 mmol) was added in two portions (⅔ and ⅓), and the temperature of the mixture was raised to 40° C. (the ether refluxed). After maintaining this temp. for 15–20 min, the mixture was poured onto $CO_2(s)$,

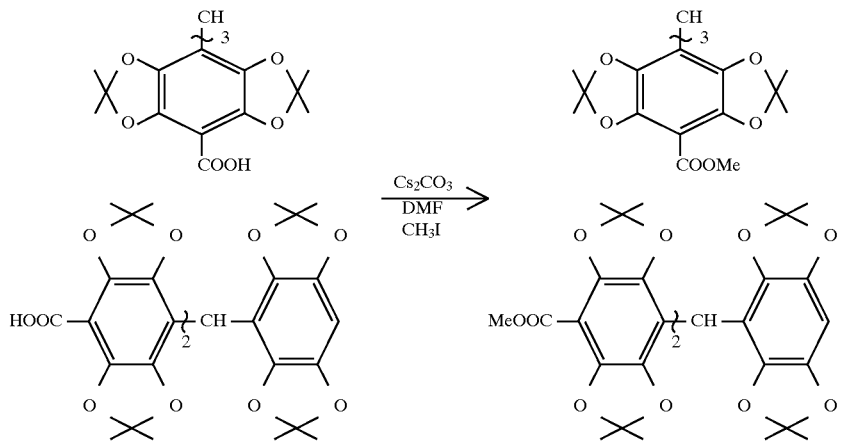

and left overnight. Water (90 mL) was added to dissolve the solid residue. The aqueous phase was washed with ether (50 mL). The aqueous phase was then acidified with 2M HCl to pH 1–2, and the tan coloured precipitate which formed was filtered off, washed with of water (7 mL) and dried. RP-TLC ($SiO_2$ RP18: glassplates) in $MeOH:H_2O$ (4:1) showed mainly two spots, (diacid and triacid with Rf=0.51 and 0.81, respectively). The product tris(8-carboxyl-2,2,6,6-tetramethylbenzo[1,2-d:4,5-d']-bis(1,3)dioxole-4-yl)methane was not separated from the mixture (1.43+0.10= 1.53 g (raw material of acids)) but was used without further purification in esterification or amidation reactions. The products of these reactions can be separated by chromatography.

A mixture of the acids tris(8-carboxy-2,2,6,6-tetramethyl-benzo[1,2-d:4,5-d']-bis(1,3)dioxole-4-yl)methane and bis(8-carboxy-2,2,6,6-tetramethyl-benzo[1,2-d:4,5-d']-bis(1,3)-dioxole-4-yl)-(2,2,6,6-tetramethyl-benzo[1,2-d:4,5-d']-bis(1,3)dioxole-4-yl)methane (3.0 g, 0.36 mmol, Example 18) were dissolved in dry DMF (70 mL) and $Cs_2CO_3$ (9.8 g, 30 mmol) was added. The mixture was heated to 70° C. for 1.5 h and was then cooled to room temperature and $CH_3I$ (6.74 mL, 108 mmol) was added with efficient stirring at 35° C. for 40 h, and the reaction mixture was filtered and the solvent (DMF) evaporated at reduced pressure. The residue was partitioned between $CH_2Cl_2$ (200 mL) and water (70 mL). The organic phase was extracted with another portion of water (70 mL). The aqueous phases were extracted back with of CH₂Cl₂ (70 mL). The organic phases were extracted with a solution of saturated NaHCO₃, dried (Na₂SO₄) and the solvent evaporated, leaving a light brown crystalline residue (3.05 g), which was chromatographed on a semi preparative reversed phase column (30 cm i.d., packed with 10 μm Kromasil, C8), eluting with CN:H₂O (75:25).

Yield of tris(8-methoxycarbonyl-2,2,6,6-tetramethylbenzo[1,2-d:4,5-d']-bis(1,3)dioxole-4-yl)methane 1.70 g (55%).

¹H NMR (CDCl₃, 300 MHz) δ: 1.53 (s, CH₃, 36H, 3.87 (s, OCH₃, 9H), 5.42 (s, CH, 1H).

¹³C NMR (CDCl₃, 75 MHz) δ: 163.8 (C=O) 140.1, 140.0 (aromatic C—O), 118.4 (aliphatic O—C—O), 110.3 (quart. arom. C), 98.5 (p-substituted quart. aromatic), 51.8 (OCH₃), 31.3 (C—H), 25.5 (CH₃).

MS (Thermospray: M⁺+23 (Na) 873.

Yield of bis(8-methoxycarbonyl-2,2,6,6,-tetramethylbenzo[1,2-d:4,5-d']-bis(1,3)dioxole-4-yl)-(2,2,6,6-tetramethylbenzo[1,2-d:4,5-d']-bis(1,3)dioxole-4-yl) methane=0.60 g (20%).

¹H NMR (CDCl₃, 300 MHz) δ: 1.47 (s, CH₃, 12H, 1.53 (s, CH₃, 24H), 3.87 (s, OCH₃, 6H) 5.42 (s, CH, 1H), 6.21 (s, aromatic H, 1H).

Ms (Thermospray): M⁺+23 (Na) 815.

EXAMPLE 20

Tris(8-methoxycarbonyl-2,2,6,6-tetramethylbenzo[1,2-d:4,5-d']-bis(1,3)-dioxole-4-yl)methane and bis(8-methoxycarbonyl-2,2,6,6-tetramethylbenzo[2-d:4,5-d']bis(1,3)-dioxole-4-yl)-(2,2,6,6-tetramethylbenzo[1,2-d:4,5-d']-bis(1,3)-dioxole-4-yl)methane

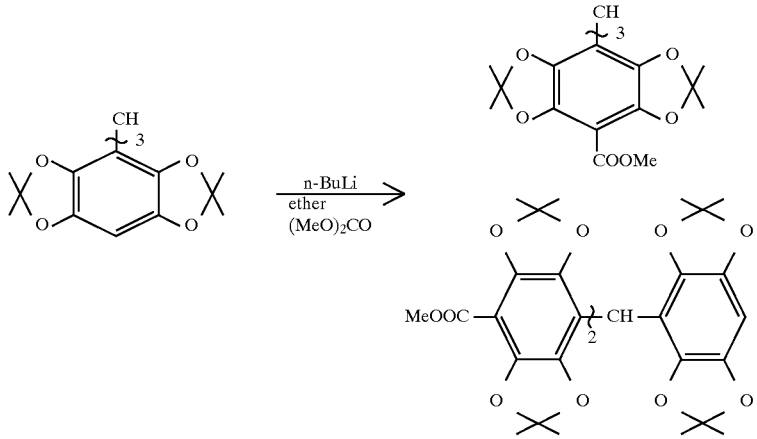

Tris(2,2,6,6-tetramethylbenzo[1,2-d:4,5-d']bis(1,3) dioxole-4-yl)methane (3.00 g, 4.40 mmol (Example 17)) was dissolved in ether (100 mL) and n-BuLi (10.8 mL, 27.0 mmol) was added. The mixture was refluxed for 20 min, and after cooling to room temperature dimethylcarbonate (5.60 mL, 67.0 mmol) was added. The mixture turned dark brown, and the reaction mixture was stirred over night at room temperature. Water (40 mL) was added and the phases were separated. The aqueous phase was extracted with another portion of ether (50 mL). The organic phases were pooled, dried and filtered, and the solvent evaporated leaving a semisolid brown residue. This was chromatographed on a SiO₂ column (0.040–0.063 mm), eluting first with petroleum-ether/ether (1:4) and then with ethyl acetate (EtOAc). The diester bis(8-methoxycarbonyl-2,2,6,6-tetramethylbenzo[1,2-d:4,5-d']bis(1,3) dioxole-4-yl)-(2,2,6,6-tetramethylbenzo[1,2-d:4,5-d']-bis(1,3)dioxole-4-yl) methane (1.27 g, 33.1%) and the triester tris(8-methoxycarbonyl-2,2,6,6-tetramethylbenzo[1,2-d:4,5-d']-bis(1,3)dioxole-4-yl)methane (0.37 g, 11.0%) were isolated. For spectroscopic data see Example 19.

EXAMPLE 21

Tris(8-ethoxycarbonyl-2,2,6,6-tetramethylbenzo[1,2-d:4,5-d']-bis(1,3)dioxole-4-yl)methane

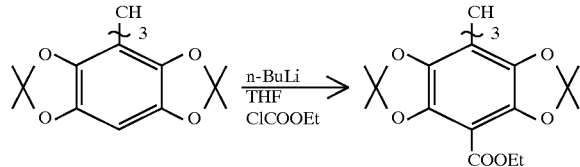

Tris(2,2,6,6-tetramethylbenzo[1,2-d:4,5-d']bis(1,3) dioxole-4-yl)methane (1.35 g, 2.0 mmol (Example 17)) was dissolved in dry THF (400 mL) under N₂, and the temp was lowered to −40° C. and n-BuLi (4.86 mL, 12.2 mmol) was added and the temperature was allowed to rise gradually to 0° C. The mixture was cooled to −60° C., and a solution of ethylchloroformate (4.0, 36.7 mmol) in THF (50 mL) was added. The reaction mixture was left overnight and worked up as described under Example 20 above. The chromatography gave (0.41 g, 24%) of tris(8-ethoxycarbonyl-2,2,6,6-tetramethylbenzo[1,2-d:4,5-d']-dioxole-4-yl) methane.

¹H NMR (CDCl₃, 300 MHz) δ: 1.35 (t, CH₃, 9H), 1.52 (s, CH₃, 36H), 4.34 (q, $_{CH2}$, 6H), 5.41 (s, CH, 1H).

¹³C NMR (CDCl₃, 75 MHz) δ: 163.4 (C—O), 140.1, 140.0 (aromatic C—O), 118.3 (aliphatic O—C—O), 110.2 (quart. aromatic C), 98.8 (quart. C-substituted aromatic), 60.7 (CH₂), 31.3 (C—H), 25.5 (CH₃), 14.2 (CH₃).

EXAMPLE 22

Tris(8-methylcarbonyloxymethyl-2,2,6,6-tetramethylbenzo[1,2-d:4,5-d']-bis(1,3)dioxole-4-yl)methanol

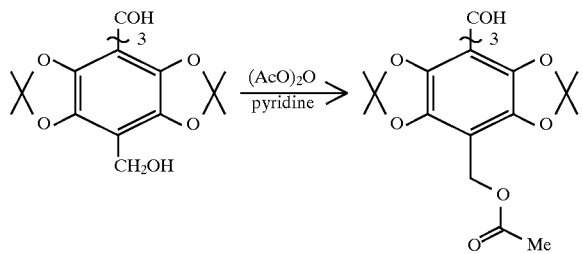

Acetic anhydride (AcO)$_2$O (30 mL) was added to pyridine (35 mL). Tris(8-hydroxymethyl-2,2,6,6-tetramethylbenzo[1,2-d:4,5-d']-bis(1,3)dioxole-4-yl)methanol (0.400 g, 0.51 mmol (Example 33) was added under stirring, which was maintained at room temperature for two days. Pyridine and excess anhydride were evaporated (oil-pump) at 40°–50° C. to a syrup, which was taken up in 70 mL of CH$_2$Cl$_2$. The organic phase was washed with water (30 mL), 0.5M HCl (40 mL), water (50 mL) and NaHCO$_3$ (saturated, 30 mL). The organic phase was separated, dried and the solvent was evaporated, leaving a syrup, which crystallized after standing for ca 1 h and the product tris(8-methylcarbonyloxymethyl-2,2,6,6-tetramethyl-benzo[1,2-d:4,5-d']-bis(1,3)dioxole-4-yl)methanol was isolated (0.460 g, 100%).

$^1$H NMR (300 MHz, CDCl$_3$) δ: 1.48 (s, CH$_3$, 36H), 2.05 (s, CH$_3$CO, 9H), 5.25 (s, CH$_2$, 6H), 4.19 (s, OH, 1H)

Ms (Thermospray): M$^+$+23 (Na) 931.

EXAMPLE 23

Tris(8-formyl-2,2,6,6-tetramethylbenzo[1,2-d:4,5-d']-bis(1,3)dioxole-4-yl)methane and bis(8-formyl-2,2,6,6-tetramethylbenzo[1,2-d:4,5-d']-bis(1,3)dioxole-4-yl)-(2,2,6,6-tetramethylbenzo[1,2-d:4,5-d']-bis(1,3)dioxole-4-yl)methane Tris(2,2,6,6-tetramethyl-benzo[1,2-d:4,5-d']-bis(1,3)-dioxole-4-yl)methane (2.0 g, 3.5 mmol (Example 17)) was dissolved in dry ether (100 mL) at room temperature. Under an inert atmosphere n-butyl lithium (6 mL) was added, and the reaction mixture was heated to reflux (15 min). At this temperature another portion of n-butyl lithium (2 mL) was added and the heating was interrupted. After 5 min DMF (2.7 mL, 35 mmol) was carefully added and the reaction mixture was left stirring at room temperature overnight. Water (100 mL) and glacial acetic acid (1.5 mL) were added to the reaction mixture and the phases were separated. The aqueous phase was extracted with water (2×50 mL), and dried over a mixture of Na$_2$SO$_4$ and K$_2$CO$_3$. After filtering through a bed of SiO$_2$ the solvent was evaporated leaving a yellow to red crystalline residue, which was chromatographed on a column of SiO$_2$ with CH$_2$Cl$_2$/ether (4:1) as eluent, yielding pure dialdehyde bis(8-formyl-2,2,6,6-tetramethylbenzo[1,2-d:4,5-d']-bis(1,3)-dioxol-4-yl)-(2,2,6,6-tetramethylbenzo[1,2-d:4,5-d']-bis(1,3)-dioxol-4-yl)methane 0.610 g (20%) and trialdehyde tris(8-formyl-2,2,6,6-tetramethylbenzo[1,2-d:4,5-d']-bis(1,3)dioxol-4-yl)methane 1.23 g (51%). Bis(8-formyl-2,2,6,6-tetramethylbenzo[1,2-d:4,5-d']bis(1,3)dioxole-4-yl)-(2,2,6,6-tetramethylbenzo[1,2-d:4,5-d']-bis(1,3)dioxol-4-yl)methane:

$^1$H NMR (300 MHz CDCl$_3$) δ: 1.50 (s, CH$_3$, 12H) 1.55 (s, CH$_3$, 24H) 5.42 (s, C—H, 1H) 6.24 (s, aromatic H, 1H) 10.06 (s, CHO, 2H).

$^{13}$C NMR (75 MHz, CDCl$_3$) d:185.59, 140.19, 140.15, 139.67, 139.59, 119.46, 117.15, 113.10, 105.36, 105.21, 91.40, 31.43, 25.52, 25.36.

MS (Thermospray): M$^+$+23 (Na) 770.

Tris(8-formyl-2,2,6,6-tetramethylbenzo[1,2-d:4,5-d']-bis(1,3)-dioxole-4-yl)methane:

$^1$H NMR (300 MHz, CDCl$_3$) δ: 1.56 (s. CH$_3$, 36H) 5.44 (s. C—H, 1H) 10.07 (s. CHO, 3H).

$^{13}$C NMR (75 MHz, CDCl$_3$) δ: 185.5 (C—O) 140.3 140.1 (arom C—O) 119.7 (alif. O—C—O) 111.9 (quart. arom C) 105.4 (p-sub. quart. arom C) 31.7 (C—H) 25.6 (CH$_3$).

IR (KBr, cm-1): 1700 (s. C—O) 2980 (m, C—H str) 1040 (s. Ar—O—C).

MS (Thermospray): M$^+$+23 (Na) 783.0.

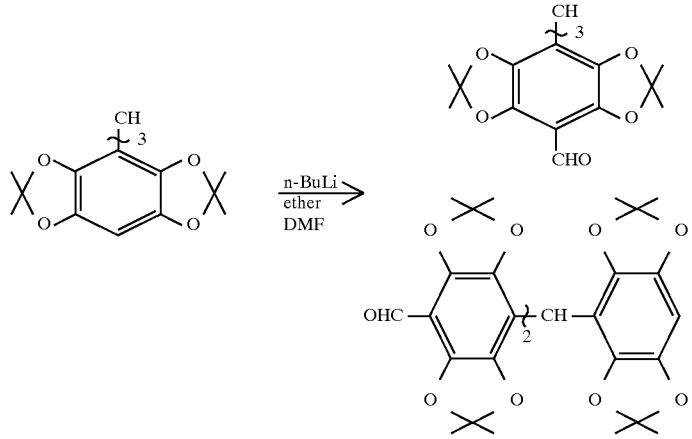

EXAMPLE 24

Tris(8-formyl-2,2,6,6-tetramethylbenzo[1,2-d:4,5-d']-bis(1,3)-dioxole-4-yl)methyl

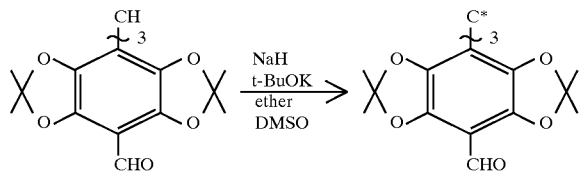

Tris(8-formyl-2,2,6,6-tetramethylbenzo[1,2-d:4,5-d']-bis(1,3)-dioxole-4-yl)methane (140 mg, 0.18 mmol, Example 23) was dissolved in a mixture of dry DMSO (15 mL) and of dry ether (50 mL). NaH (5 mg, 0.19 mmol) and t-BuOK (catalytic amount) were added under $N_2$-atmosphere. The color of the solution changed from yellow to deep green-blue. After 4 h of stirring at room temperature under $N_2$ $I_2$ (46 mg, 0.18 mmol) was added, and after 2 min the reaction mixture was poured into a saturated solution of $Na_2S_2O_3$ (100 mL). The organic phase was separated, dried ($Na_2SO_4$) and the solvent was evaporated leaving a black crystalline residue weighing 0.120 g (88%).

MS (Thermospray): $M^+ +23$ (Na) 782.0.

Radical content (NMR method) >50%.

ESR: 4 lines (internal ratio 1:3:3:1) with line widths of ca 70 mG.

Overhauser enhancements: 9 mW: 13 18 mW: 25 5 mW: 152 5 mW: 254 after dilution to 10 mM.

EXAMPLE 25

Tris(8-formyl-2,2,6,6-tetramethylbenzo[1,2-d:4,5-d']-bis(1,3)dioxol-4-yl)methyl

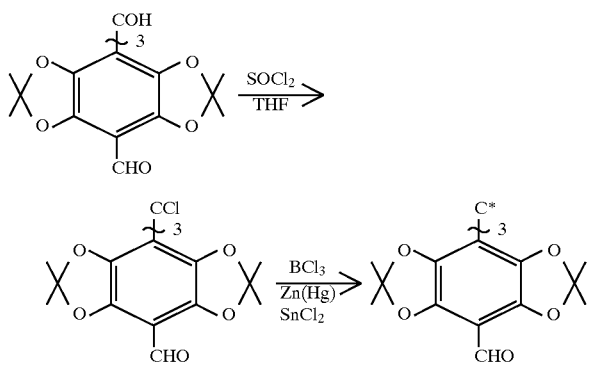

Tris(8-formyl-2,2,6,6-tetramethylbenzo[1,2-d:4,5-d]-bis(1,3)dioxole-4-yl)methanol (200 mg, 0.20 mmol) was dissolved in of dry THF (15 mL) and $SOCl_2$ (80 mg, 0.20 mmol) was added. After stirring at room temperature for 2 h the solvent was evaporated (<70° C.) and the residue was pumped dry overnight. The orange product tris(8-formyl-2,2,6,6-tetramethyl-benzo[1,2-d:4,5-d]bis(1,3)-dioxol-4-yl)methylchloride was dissolved in of dry THF (15 mL) and $BCl_3$ (0.26 mL, 1M in $CH_2Cl_2$) was added at room temperature and the solution immediately turned black. After 0.5 h of stirring under $N_2$-atmosphere was added; first $SnCl_2$ (0.15 g, 0.80 mmol) and then Zn(Hg), (0.15 g, 2.20 mmol) (prepared by treating 120 g zinc powder with a mixture of 12 g $HgCl_2$, 6 mL conc. HCl and 150 mL of water for 5 min.

and decanting off the liquid). Stirring was maintained for 0.5 h. The reaction mixture was applied to a column (1 cm diameter) consisting of 3 cm of $SiO_2$ at the bottom and 15 cm of Chelex 100 on top. Elution was performed with dry THF under $N_2$-atmosphere. The eluent was evaporated to dryness, leaving a brown-black crystalline residue (0.19 g, 100%).

Radical content was ca 27% according to HPLC (ion pair, tetrabutylammoniumacetate, $SiO_2$ C18, $CH_3CN/H_2O$ (75:25)). ESR spectrum of 4 peaks (int ratio 1:3:3:1) with 70 mG linewidth.

EXAMPLE 26

Tris(8-methoxycarbonyl-2,2,6,6-tetramethylbenzo[1,2-d:4,5-d']-bis(1,3)dioxole-4-yl)methyl

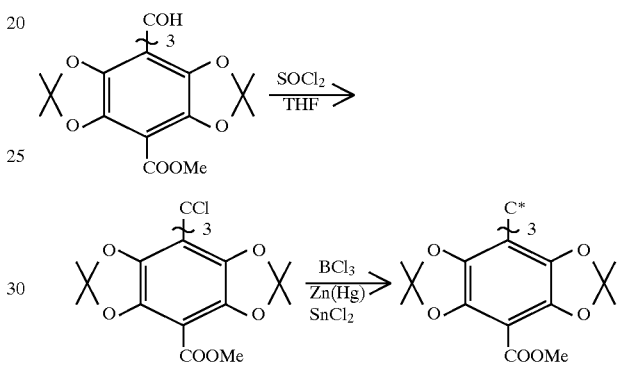

Tris(8-methoxycarbonyl-2,2,6,6-tetramethylbenzo[1,2-d:4,5-d']-bis(1,3)dioxol-4-yl)methanol (240 mg, Example 15) was dissolved in of dry THF (25 mL) and $SOCl_2$ (38 mg, 23 L) was added at room temperature. Stirring was maintained for 2.5 h. The solvent of the reaction mixture was then evaporated to dryness (<70° C.). After pump drying over night tris(8-methoxycarbonyl-2,2,6,6-tetramethylbenzo[1,2-d:4,5-d']-bis(1,3)dioxole-4-yl)methylchloride was dissolved in of dry THF (25 mL) and, in turn $SnCl_2$ (0.10 g, 0.53 mmol) and then Zn(Hg) (see Example 25) (0.10 g, 1.52 mmol) were added under $N_2$. The solution turned black and was filtered through a column (1 cm diameter) of 15 cm Chelex 100 (top) and 3 cm of $SiO_2$ (bottom), under $N_2$ with THF as eluent. The solvent was evaporated leaving a black crystalline residue (0.20 g).

ESR spectrum showed 10 lines with linewidths=48 mG. A radical content of ca 5% was estimated by ESR. At 75 mW, the Overhauser enhancement was 80.

EXAMPLE 27

Tris(8-ethoxycarbonylmethylthio-2,2,6,6-tetramethylbenzo[1,2-d:4,5-d']-bis(1,3)dioxole-4-yl)methanol

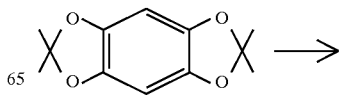

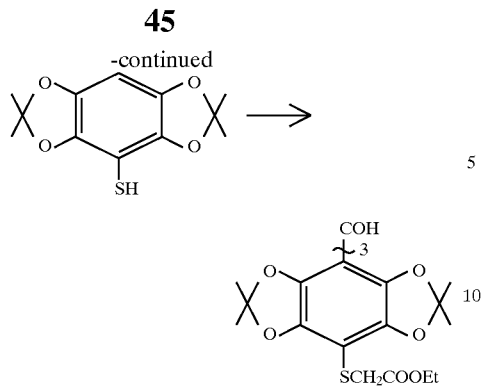

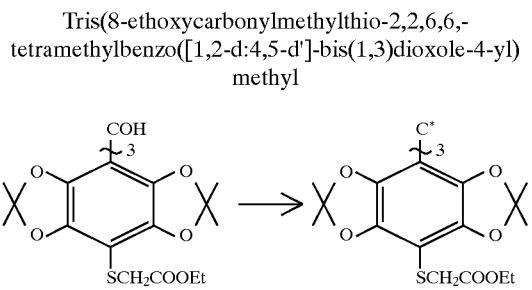

EXAMPLE 28

Tris(8-ethoxycarbonylmethylthio-2,2,6,6,-tetramethylbenzo([1,2-d:4,5-d']-bis(1,3)dioxole-4-yl) methyl 2,2,6,6-Tetramethylbenzo[1,2-d:4,5-d']bis(1,3)dioxole (2.22 g, 10 mmol (Example 5)) was dissolved in dry tetrahydrofuran (dried using sodium benzophenone ketyl) and cooled to −78° C. under argon. n-Butyllithium (4.25 mL, 2.5M in hexane, 10.6 mmol) was added. The cooling bath was removed 35 minutes later and the mixture stirred for 40 minutes, when dry sulfur (S8, 0.320 g, 1.25 mmol) was added in one portion. The sulfur had dissolved one hour and fifteen minutes later. The reaction mixture was then recooled to −78° C. and n-butyllithium (4.25 mL, 10.6 mmol) was added. The dry ice/acetone bath was exchanged with a water/ice bath. The new cooling bath was removed after one hour and forty five minutes. Cold (−78° C.) diethylcarbonate (0.363 mL, 3 mmol) in THF (10 mL) was cannulated into the reaction mixture over a period of 10 minutes. The resulting mixture was kept at (−70)°–(−78)°C. for two hours, followed by a period of one hour and thirty minutes at approximately 0° C. (ice/water bath). The mixture was then stirred till noon the following day without addition of ice, at which time the temperature inside the reaction flask was +16° C. The mixture was then stirred without external cooling for three more hours, poured into a half saturated sodium dihydrogenphosphate buffer (100 mL) and extracted with diethylether (4×100 mL). The organic phase was washed with the same buffer (50 mL) and dried (MgSO$_4$). This yielded 2.93 g of product, which by 1H NMR (300 MHz, CDCl$_3$) was shown to contain approximately 50% of tris(8-mercapto-2,2,6,6-tetramethylbenzo[1,2-d:4,5-d']-bis(1,3)dioxol-4-yl)methanol. The was used immediately in the next step.

Tris(8-mercapto-2,2,6,6-tetramethylbenzo[1,2-d:4,5-d']-bis(1,3)dioxol-4-yl)methanol (2.93 g, 50%, 1.86 mmol) was dissolved in dry DMF (100 mL) under argon. K$_2$CO$_3$ (4 g) was added and the solution cooled to the freezing point. Ethylchloroacetate (5 mL, 46.7 mmol, Janssen 11822.85) was added, and the reaction mixture was stirred at room temperature overnight. Most of the DMF and excess ethylchloroacetate were removed by high vacuum distillation at 30°–40° C. The residue was mixed with saturated sodium dihydrogenphosphate buffer (100 mL) and extracted with diethyl ether (4×150 mL). The etheral phase was washed with phosphate buffer (2×50 mL) and water (50 mL), dried (MgSO$_4$) and evaporated. Purification was achieved through two flash chromatography (E. Merck 0.040–0.063 mm SiO$_2$) separations with n-heptane: ethyl acetate (1:1), followed by straight phase (E.Merck 20–45 mm CH$_2$Cl$_2$:EtOAc 9:1) and reversed phase (Prep-pak C18, MeOH:H$_2$O, 8:2, 15% CH$_2$Cl$_2$ in application volume) HPLC chromatography, and finally recrystallization from diisopropyl ether. Yield (1.57 g, 15%, 1.5 mmol).

UV (maxima/minima): 220 (p), 249(v), 259(p), 297(v), 344(p). Other spectroscopic data; see Example 9.

Tris(8-ethoxycarbonylmethylthio-2,2,6,6,-tetramethylbenzo([1,2-d:4,5-d]-bis(1,3)dioxole-4-yl) methanol (2.00 g 1.91 mmol) (prepared as described in Example 27) was dissolved in dry (sodium benzophenone ketyl) degassed (Ar) THF (1.0 L) in a separatory funnel (2.0 L). A rapid stream of argon was bubbled through the solution. Borontrifluoroethyl etherate (2.88 mL 48% Fluka 15720) was added with a syringe. The clear solution turned immediately dark blue, indicating formation of the corresponding cation. Tin(II)chloride (2.90 g 15.3 mmol E.Merck 818150) was added. The color changed from blue to colorless to geen in a couple of minutes, and the resulting mixture was bubbled with argon for 10 minutes, when Zinc (2.50 g, 38.2 mmol Janssen 19.834.46) (activated by treatment with 1M hydrochloric acid followed by water, ethanol and diethylether washings and high vacum drying) was added. The argon bubbling was continued for another 20 minutes, when more zinc (2.5 g) was added. 45 Minutes later the last amount of zinc (3.0 g) was added, followed by borontrifluoroethyl etherate (1.44 mL). The reaction was continously monitored by HPLC. The substrate and the radical separated on an analytical RP18 column (Nucleosil 5 mm) with acetonitrile:water (75:25) containing the ion pair tetrabutylammonium acetate (5 mM) (pH 6.7). The detector system consisted of a diode array UV detector (Varian 9065 polychrome). The radical was distinguished from the substrate by the UV spectra (see below). The reaction was stopped when the radical content reached a maximum (~90% by UV, not considering different extinction coefficients). The volume of the reaction mixture was reduced to about 700 mL during the reaction period. The reaction mixture was diluted with dry (sodium benzophenone ketyl) diethylether (1.0 L) and extracted with dry, oxygen free sodium hydroxide (2×100 mL, 2M, 0° C., He). The organic phase was filtered through a SiO$_2$ column (40 cm long, I.D. 5 cm, E. Merck 9385 0.0040–0.063 mm). The column was preconditioned with dry oxygen free diethylether before the filtration. The last portion of the radical was eluted with pure diethylether (sodium benzophenone ketyl, Ar). The radical was obtained as black/green crystals after evaporation under argon. Yield (1.87 g, 1.814 mmol, 95%).

MS (Thermospray): M$^+$+23 (Na) 1052.

UV (Absorbtion maxima/minima): 195(p), 229(sh), 302 (v), 339(p), 348(v).

ESR (THF): 7 lines, 1 w 30 mG, aH 60 mG.

Overhauser (THF less than 1 mM conc., 200 G): freq. 548.9 MHz, 9 mW 78 enhancement, 18 mW 116 enhancement.

EXAMPLE 29

Tris(2,2,6,6-tetramethyl sodium-8-carboxylatomethylthiobenzo[1,2-d:4,5-d']-bis(1,3)dioxole-4-yl)methyl

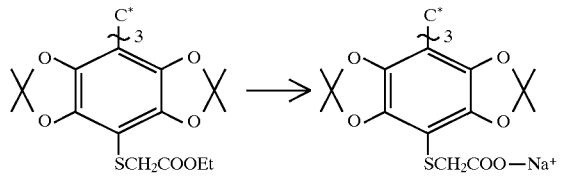

Tris(8-ethoxycarbonylmethylthio-2,2,6,6,-tetramethylbenzo-[1,2-d:4,5-d']-bis(1,3)dioxole-4-yl)methyl (1.97 g, 1.91 mmol 90% pure) was dissolved in a degassed (helium followed by argon) mixture of dioxane (Lab Scan C2512 HPLC quality) and water (200 mL (3:1)). Sodium hydroxide (4.3 mL, 2M, 8.58 mmol, He, Ar, 0° C.) was added and the hydrolysis performed in an ultrasound bath (Sonorex RK 2555). The reaction was followed by HPLC, RP18 column (Nucleosil 5 mm) with acetonitrile:water (75:25) containing tetrabutylammonium acetate (5 mM, pH 6.7). The detector system consisted of a diode array UV detector—Varian 9065 polychrome). During the reaction the diester—and monoester radicals were observed as well as the tricarboxylic acid salts. The reaction mixture was frozen when the HPLC analysis showed pure tricarboxylic acid sodium salt (mixture of radical and carbinol) and subjected to freeze drying. Yield (2.07 g, 100% 1.90 mmol) of a black/brown, fluffy material, containing excess NaOH.

Radical content: 50% (NMR—Evans method).

ESR ($H_2O$ 0.3 mM, 200 G): 7 lines, Lw 27 mG, $a_H$ 60 mG, 200 G, Freq. 548.9 MHz.

Overhauser:($H_2O$ 0.3 mM, 200 G): Freq. 548.9 MHz, 9 mW 63 enhancement, 18 mW 81 enhancement.

EXAMPLE 30

8-Mercapto-2,2,6,6-tetramethylbenzo[1,2-d:4,5-d']-bis(1,3)dioxole

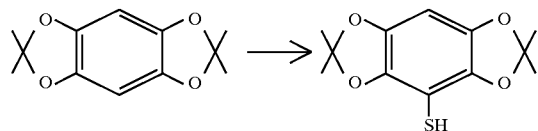

2,2,6,6-Tetramethylbenzo[1,2-d:4,5-d']bis(1,3)dioxole (30.0 g, 135 mmol (Example 5)) was dissolved in dry (sodium benzophenoneketyl) diethylether (250 mL), and heated to reflux. n-Butyllithium (50 mL, 2.68M in toluene, 134 mmol) was added and the reflux continued one hour. The flask was cooled to −78° C. and sulfur (4.297 g, 134 mmol) added. The cooling bath was exchanged with an ice/water cooling bath and the reaction mixture was stirred for one hour before alkaline water was added (150 mL, 1M, degassed with argon) followed by vigorous stirring in ten minutes. The phases were separated and the water phase was washed with diethylether (100 mL, degassed with argon). The water phase was acidified with HCl (5M). The precipitated crystals were taken up in diethylether (degassed argon), dried ($MgSO_4$) and evaporated to dryness. The pure crystals are stable for weeks under argon in the freezer. Yield: 24.86 g (72.5%).

$^1$H NMR ($CDCl_3$, 300 MHz) δ: 1.65, 3.28, 6.13.

$^{13}$C NMR ($CDCl_3$, 75 MHz) δ: 139.87, 138.33, 118.31, 94.99, 90.23, 25.54.

EXAMPLE 31

Tris(8-mercapto-2,2,6,6-tetramethylbenzo[1,2-d:4,5-d']bis(1,3)dioxole-4-yl)methanol

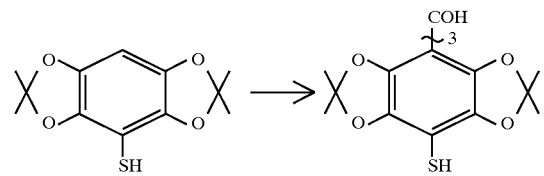

8-Mercapto-2,2,6,6-tetramethylbenzo[1,2-d:4,5-d']-bis(1,3)dioxole (24.9 g, 97.9 mmol (Example 30)) was-dissolved in dry diethylether (200 mL) in a three necked round-bottomed flask, equipped with a sintered glass filter (no. 4) at one of the outlets. The reaction mixture was cooled to (−78)°C. and n-butyllithium (36.5 mL, 97.9 mmol, in toluene) was added. The dry ice/acetone bath was exchanged with a water/ice bath. The new cooling bath was removed after one hour. The solvent, and most of the soluble impurities were removed from the lithium salt by filtration through the sintered glass filter. The whole filtration took about ten minutes. The salt was washed to the bottom of the flask with dry diethylether (30 mL). Tetrahydrofuran (250 mL, sodium benzophenone ketyl dried) was added and the solution was cooled to (−78° C.). n-Butyl lithium (36.5 mL, 97.9 mmol, in toluene) was added. After a period of ten minutes, the temperature was gradually raised to 0° C. with a water/ice bath. The mixture was stirred with this cooling for one hour and twenty minutes, followed by a period of thirty minutes at room temperature. After recooling to (−78) °C., diethylcarbonate (3.63 mL, 30 mmol) in tetrahydrofuran (20 mL) was added to the reaction mixture over a period of one minute. The temperature was raised gradually with the help of a water/ice bath. The reaction was followed by taking samples (quench of small samples in sodium dihydrogenphosphate buffer under argon, evaporating organic phase) and running $^1$H NMR. The trimerisation was complete after four hours. The mixture was quenched with sodium dihydrogenphosphate buffer (saturated, 130 mL), stirred twenty minutes and the phases were separated. The water phase was extracted with diethylether (50 mL, argon) and the organic phases were combined, washed (sodium dihydrogen phosphate buffer, 30 mL), dried ($MgSO_4$, 30 min) and evaporated to dryness. Diethylether (dry, argon) was added to the brown oil to induce the crystallization. Upon the dissolution of the oil the title compound crystallized as porous yellow crystals. The product was isolated by filtration.

Yield: 10.0 g (12.7 mmol, 39%).

$^1$H NMR ($CDCl_3$, 300 MHz) δ: 1.49, 3.25, 4.10.

$^{13}$C NMR ($CDCl_3$, 75 MHz) δ: 138.54, 138.26, 117.51, 110.16, 93.55, 72.33, 25.53.

MS (Thermospray): $M^+$+23 (Na) 811.

Crystallization of the mother liquor gave ($^1$H NMR) 0.8 g of dimeric (ketone) product. (See Example 51).

EXAMPLE 32

Tris(8-ethoxycarbonylmethylthio-2,2,6,6-tetramethylbenzo[1,2-d:4,5-d']-bis(1,3)dioxole-4-yl)methanol

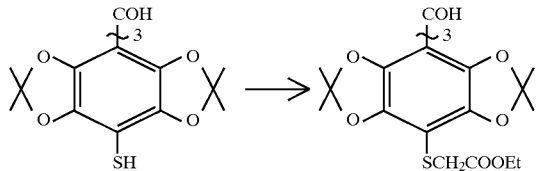

The title compound was made with pure tris(8-mercapto-2,2,6,6-tetramethylbenzo[1,2-d:4,5-d']-bis(1,3)-dioxole-4-yl)methanol (from Example 31) (2.10 g 2.67 mmol) and ethylchloroacetate (16.0 mmol), using a procedure analogous to that described in Example 27. Yield 1.93 g (98%).

$^1$H NMR (CDCl$_3$, 300 MHz) δ: 4.12, 3.54, 1.51, 1.24.

$^{13}$C NMR (CDCl$_3$, 75 MHz) δ: 169.00, 141.22, 138.64, 117.75, 112.40, 96.62, 72.48, 61.20, 35.47, 25.42, 14.08.

EXAMPLE 33

Tris(8-hydroxymethyl-2,2,6,6-tetramethylbenzo[1,2-d:4,5-d']-bis(1,3)-dioxol-4-yl)methanol

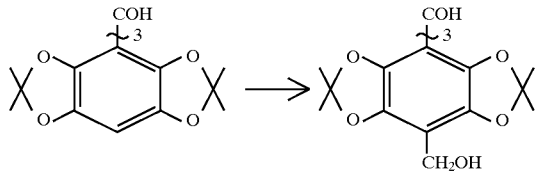

Tris(2,2,6,6-tetramethylbenzo([1,2-d:4,5-d']-bis(1,3) dioxol-4-yl)methanol (6.35 g, 9.38 mmol) was dissolved in dry diethylether (200 mL) under argon and cooled to 0° C. n-Butyllithium (22.5 mL, 56.30.10−3 mol) was added and the temperature was increased to induce reflux. The reaction mixture was refluxed for 25 minutes. After cooling to 0° C., dry formaldehyde (gas, formed by sublimation) (4.0 g, 133 mmol) was added and the resulting mixture was stirred over night while the temperature gradually was increased to room temperature. After quenching with sodium dihydrogenphosphate buffer (200 mL; saturated), extraction with diethylether (5×250 mL), drying (MgSO$_4$) and evaporation, the product was isolated by column chromatography (E. Merck 0.040–0.063 mm SiO$_2$, 6.27 cm, CH$_2$Cl$_2$:EtOAc 3:2 (2.0 L), CH$_2$Cl$_2$:EtOAc (1:1) (2.0 L), CH$_2$Cl$_2$:EtOAc (2:3) (2.0 L). Yield 0.239 g (0.305 mmol (3.3%).

$^1$H NMR (300 MHz, CDCl$_3$) δ: 4.59 (s, CH$_2$, 6H), 1.23 (s, CH$_3$, 36H), OH not seen.

$^{13}$C NMR (75 MHz, CDCl$_3$) δ: 138.70, 139.38, 117.23, 105.88, 72.51, 56.66, 25.48.

EXAMPLE 34

Tris(8-methoxymethyl-2,2,6,6-tetramethylbenzo[1,2-d:4,5-d'](1,3)dioxole-4-yl)methanol

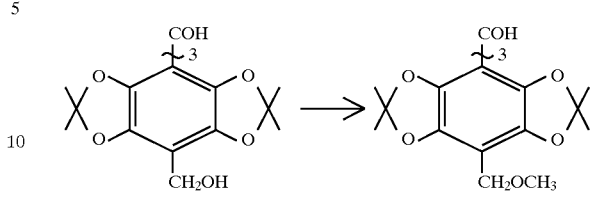

Tris(8-hydroxymethyl-2,2,6,6-tetramethylbenzo[1,2-d:4,5-d'](1,3)dioxole-4-yl)methanol (0.105 g, 0.134 mmol (Example 33)) and a catalytic amount of tetrabutylammoniumhydrogen sulfate were added to a preformed solution of dimethylsulfate (0.2 mL) and sodium hydroxide (50%, 1.0 mL) in CH$_2$Cl$_2$ (2 mL). The resulting solution was stirred at ambient temperature for 48 hours. The mixture was evaporated and the resulting oil chromatographed on silica (CH$_2$Cl$_2$:diethylether (5:1)). The major product was not completely pure according to TLC, but upon dissolution in CDCl$_3$ the impurities did not dissolve. Evaporation of the filtered solution yielded 94 mg (0.114 mmol, 85%) of pure title compound.

$^1$H NMR (300 MHz, CDCl$_3$) δ: 4.40 (s, CH$_2$, 6H), 3.30 (s, CH$_3$, 9H), 1.47 (s, CH$_3$, 36H), OH not seen.

$^{13}$C NMR (75 MHz, CDCl$_3$) δ: 139.64, 138.58, 116.97, 112.37, 102.65, 72.61, 63.49, 57.16, 25.46.

EXAMPLE 35

Tris(8-methoxymethyl-2,2,6,6-tetramethylbenzo[1,2-d:4,5-d']bis(1,3)dioxole-4-yl)methyl

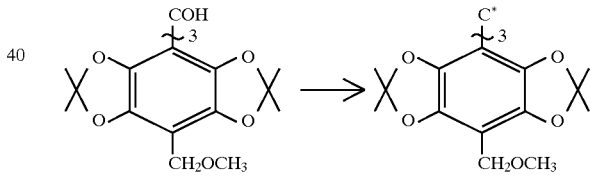

Tris(8-methoxymethyl-2,2,6,6-tetramethylbenzo[1,2-d:4,5-d']bis(1,3)dioxole-4-yl)methanol (94.0 mg, 0.114 mmol (Example 34)) and thionyl chloride (40 mL, 0.57 mmol) were stirred in tetrahydrofuran (2 mL) (sodium benzophenone ketyl dried) for 45 minutes and evaporated. The residue was dissolved in fresh tetrahydrofuran (10 mL) and boron trichloride (330 mL, 1M in CH$_2$Cl$_2$). The color of the solution turned light brown. Tin(II)chloride (127 mg, 0.986 mmol) was added 10 minutes after the boron compound, and zinc (187 mg, 2.85 mmol) was added after another 15 minutes. One hour and fifteen minutes later the reaction mixture was green. The solution was evaporated, and subsequently filtered through a SiO$_2$ column with tetrahydrofuran as the eluent. The residue (80 mg, 0.099 mmol, 87% (containing some radical precur) was dissolved in tetrahydrofuran and the radical characterized by ESR and Overhauser enhancements:

ESR (200 G): Linewidth 1.5 G (70 overlapping lines).

Overhauser enhancements (548.9 MHz, 200 G): 5 W 60 enhancements.

EXAMPLE 36

Tris(8-hydroxyethylthio-2,2,6,6-tetramethylbenzo[1,2-d:4,5- d']-bis(1,3)dioxole-4-yl)methanol

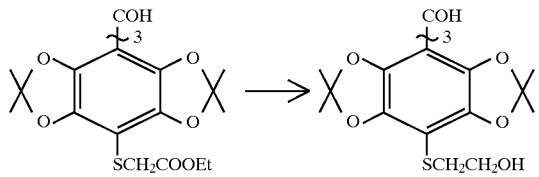

LiAlH$_4$ (15.2 mg, 0.40 mmol) was added to a solution of tris(8-ethoxycarbonylmethylthio-2,2,6,6-tetramethylbenzo-[[1,2-d:4,5-d']-bis(1,3)dioxole-4-yl)methanol (10.5 mg 0.10 mmol (Example 27)) in diethyl ether (10 mL) under nitrogen at 20° C. The reaction was followed by HPLC (reversed phase C18, acetonitrile:water (3:1), 5 mM tetrabutylammonium acetate). The mixture was quenched with ethylacetate when no more substrate was seen by HPLC. Dilute sulfuric acid was then added until pH 6–7. The ether phase was separated, and the water phase was extracted with diethyl ether. The combined etheric phases were dried (MgSO$_4$) and evaporated, yielding 0.0901 g (97.8%, 0.0978 mmol) of a yellowish oil, which gradually crystallized upon standing.

$^1$H NMR (300 MHz, Acetone d$_6$) δ: 1.49 (s, CH$_3$, 36H), 2.51 (bs, OH, 3H), 2.59 (t, CH$_2$, 6H), 4.38 (s, OH 1H).

$^{13}$C NMR (75 MHz, Acetone d$_6$) δ: 141.96, 138.93, 117.80, 112.52, 98.06, 72.50, 60.98, 36.25, 25.18.

MS (Thermospray): M$^+$+23 (Na) 943, M$^+$–18 902.

EXAMPLE 37

Tris(8-hydroxyethylthio-2,2,6,6-tetramethylbenzo[1,2-d:4,5- d']-bis(1,3)dioxole-4-yl)methyl

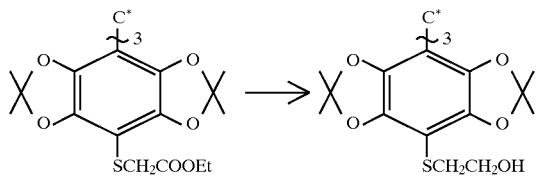

LiAlH$_4$ (95.8 mg, 2.52 mmol) was added to a solution of tris(8-ethoxycarbonylmethylthio-2,2,6,6-tetramethylbenzo-[1,2-δ:4,5-d']-bis(1,3)dioxole-4-yl)methyl (1.30 g, 1.26 mmol, 50% radical content (Example 28)) in diethylether (50 mL) under nitrogen at 20° C. The reaction was followed by HPLC (reversed phase C18, acetonitrile:water (3:1), 5 mM tetrabutylammonium acetate). The mixture was quenched with ethylacetate when no more substrate was seen according to HPLC Dilute sulfuric acid was then added until pH 6–7. The ether phase was separated, and the water phase extracted with diethylether (2×100 mL). The combined etheric phases were dried (Na$_2$SO$_4$) and evaporated, yielding 0.96 g (84%, 1.06 mmol) of a yellowish oil. The product was characterized by ESR and Overhauser measurements. HPLC chromatography in combination with diode array detection and UV spectral analysis showed a radical content of about 6–7% after evaporation overnight.

EXAMPLE 38

Tris(8-di(methylcarbonyloxyethyl) aminocarbonylmethylthio-2,2,6,6-tetramethylbenzo [1,2-d:4,5-d']-bis(1,3)dioxole-4-yl) methanol

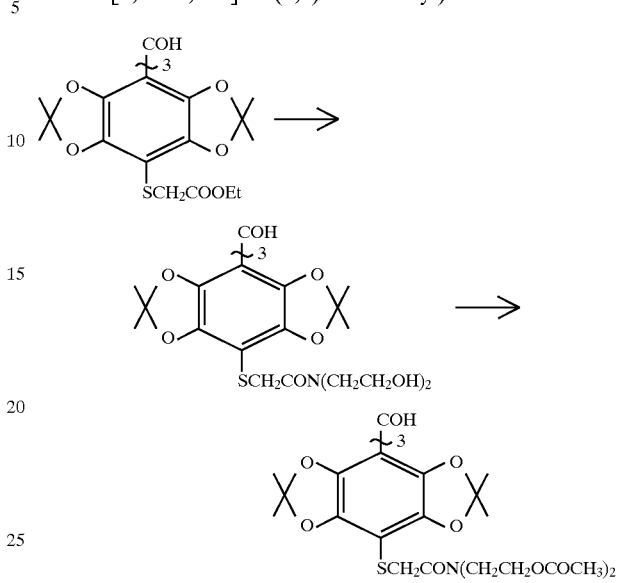

Tris(8-ethoxycarbonylmethylthio-2,2,6,6,-tetramethylbenzo-([1,2-d:4,5-d']-bis(1,3)dioxole-4-yl) methanol (0.4675 g, 0.446 mmol (Example 27)) and diethanolamine (0.939 g, 8.93 mmol) were mixed and aminolysis was performed in toluene at reflux temperature under nitrogen for thirty six hours. At this time HPLC analysis (reversed phase C18, acetonitrile: water (3:1), 5 mM tetrabutylammonium acetate, 254 nm UV detection) showed complete consumption of the starting material. The crude reaction mixture was evaporated and checked with $^{13}$C NMR without removing the excess diethanol amine from the intermediary tris(8-di(hydroxyethyl) aminocarbonylmethylthio-2,2,6,6-tetramethylbenzo[1,2-d:4,5-d']-bis(1,3)dioxole-4-yl)methanol: [(CD$_3$OD, 75 MHz) δ: 171.34, 142.55, 139.97, 119.12, 112.99, 98.94, 60.73, 60.58, 52.97, 50.36, 36.84, 25.88, central COH at ca. 72 ppm was not seen.] and redissolved in a mixture of pyridine (7.0 mL) and acetic anhydride (5.0 mL) and stirred over night at room temperature. TLC analysis (SiO$_2$ 1 methanol:ethylacetate (3:7)) showed formation of a more lipophilic product. This product was purified by two consecutive chromatographic separations on SiO$_2$ (E. Merck 0.040–0.063 mm). The first column was eluted with n-heptane:ethylacetate (1:1) and ethylacetate:ethanol (1:1). The second column was eluted with ethylacetate/n-butanol (95:5). The solvents were evaporated and the last amounts of butanol was removed by high vacuum evaporation under a period of forty eight hours. Yield 0.151 g (23%, 0.102 mmol) (about 20% more substance in the impure fractions).

$^1$H NMR (CDCl$_3$, 300 MHz) δ: 4.23 (t, CH$_2$, 6H), 4.15 (t, CH$_2$, 6H), 3.74 (s, CH$_2$, 6H), 3.70 (t, CH$_2$, 6H), 3.54(t, CH$_2$, 6H), 2.02 (s, CH$_3$, 18H), 1.49 (s, CH$_3$, 36H).

$^{13}$C NMR (CDCl$_3$, 75 MHz) δ: 170.63, 170.37, 168.40, 141.30, 138.60, 117.72, 112.38, 96.38, 72.45, 61.85, 61.83, 47.78, 45.52, 35.43, 25.39, 20.78, 20.66, (61.85 and 61.83 are nonequivalent possibly due to restricted rotation arising from the amide).

MS (Thermospray): M$^+$+23 (Na) 1495, 1496, 1497 and 1498 (scale not calibrated).

EXAMPLE 39

Tris(8-carboxylmethylthio-2,2,6,6-tetramethylbenzo-[1,2-d:4,5-d']-bis(1,3)dioxole-4-yl)methanol

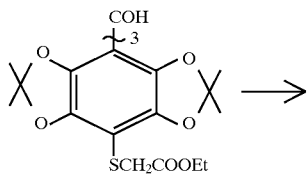

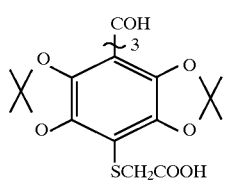

Tris(8-ethoxycarbonylmethylthio-2,2,6,6-tetramethylbenzo-[1,2-d:4,5-d']-bis(1,3)dioxole-4-yl)methanol (4.00 g, 3.819 mmol (Example 27)) was dissolved/suspended in a mixture of water and ethanol (200 mL, (1:1)) and cooled to approximately 5° C. Sodium hydroxide (15.3 mL, 1.0M, 15.3 mmol) was added and the reaction was followed by HPLC. The next day more sodium hydroxide (3.82 mL, 1.0M, 3.82 mmol) and (7.64 mL, 1.0M, 7.64 mmol) was added. The ethanol was evaporated after complete conversion had been observed (HPLC). The alkaline aqueous phase was extracted with heptane (2×100 mL) and then acidified with HCl (2.0M) to pH 5. The product was taken up in diethylether (2×100 mL). Upon further acidification of the aqueous phase (to pH 3), more precipitate was formed. This was also taken up in diethylether (2×100 mL). The combined ether phases were extracted once with water (100 mL) and dried (Na₂SO₄). Evaporation yielded 3.11 g (3.23 mmol, 85%) of a white crystalline material. When the material was dried at very high vacuum and high temperature the substance turned blue, possibly due to the formation of an internal zwitter ion. Upon exposure to moist air the white color returns.

$^1$H NMR (300 MHz, DMSOd$_6$) δ: 12.55 (bs, COOH, 3H), 3.59 (s, CH$_2$, 6H), 3.31 (bs, OH, 3H), 1.44 (s, CH$_3$, 36H).

$^{13}$C NMR (75 MHz, DMSOd$_6$) δ: 170.04, 140.18, 138.17, 117.17, 111.83, 97.13, 71.47, 34.70, 24.98.

MS (Electrospray): Calc. 962.17, found 962.17.

Titration with sodium hydroxide (0.01M) gave a purity (% of molecules with three carboxylic acids) of 99.7%±1.9% (SD).

EXAMPLE 40

8-Hydroxy-2,2,6,6-tetramethylbenzo[1,2-d:4,5-d']-(13)-dioxole

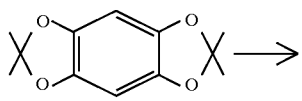

-continued

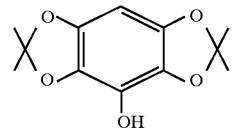

2,2,6,6-Tetramethylbenzo[1,2-d:4,5-d']-(1,3)dioxole (5.00 g, 22.5 mmol (Example 5)) was dissolved in diethyl ether (150 mL, sodium benzophenone ketyl) under argon. n-Butyl lithium (10.0 mL, 25 mmol, 2.5M in toluene) was added at room temperature followed by methyl magnesium bromide (4.25 mL, 13 mmol, 3.0M in diethyl ether, Aldrich). the resulting mixture was stirred at room temperature for 1 h. Oxygen was bubbled through the solution over a period of 2 hours, while cooling with a cold water bath. The reaction mixture was poured into a solution of NaOH (50 mL, 1M) and extracted with diethyl ether (100 mL). The aqueous phase was acidified with conc. HCl to pH 2 while stirring. The product was isolated by extracting with diethyl ether (3×50 mL). The ether was dried (Na₂SO₄) and evaporated yielding 1.50 g (6.3 mmol, 28%) of 8-hydroxy-2,2,6,6-tetramethyl-benzo[1,2-d:4,5-d']bis(1,3)dioxole.

$^1$H NMR (300 MHz, DMSOd$_6$) δ: 6.00 (s, aromatic H, 1H), 1.66 (s, CH$_3$, 12H).

MS (Thermospray): M$^+$+23 (Na$^+$) 261

EXAMPLE 41

8-Methoxy-2,2,6,6-tetramethylbenzo[1,2-d:4,5-d']-(1,3)dioxole

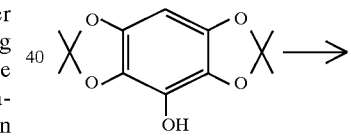

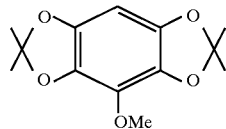

8-Hydroxy-2,2,6,6-tetramethylbenzo[1,2-d:4,5-d']-(1,3)dioxole (1.00 g, 4.20 mmol (Example 40)) was dissolved in CH₂Cl₂ (30 mL) and dimethyl sulfate (0.6 mL, 6.30 mmol), tetrabutyl-ammonium hydrogensulfate (catalytic amount) and sodium hydroxide (1.0 mL, 40%) were added. The resulting mixture was stirred at room temperature for 24 hours. The phases were separated and the aqueous phase was extracted with diethyl ether (2×50 mL). The combined organic solution was extracted with ammonia (25 mL, 25%) and water (50 mL), dried (Na₂SO₄) and evaporated. Yield 0.9 g (83%) of a yellow oil.

$^1$H NMR (CDCl$_3$, 300 MHz) δ: 6.05 (s, CH, 1H), 4.02 (s, CH$_3$, 3H), 1.65 (s, CH$_3$, 12H).

MS (Thermospray): M$^+$+23 (Na+) 275.

EXAMPLE 42

Tris(8-ethoxycarbonylmethylthio-2,2,6,6-tetramethylbenzo[1,2-d:4,5-d']-bis(1,3)dioxole-4-yl)methane

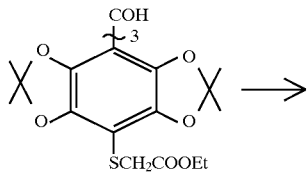

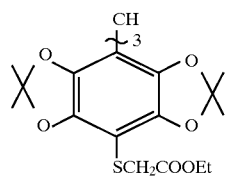

Tris(8-ethoxycarbonylmethylthio-2,2,6,6-tetramethylbenzo[1,2-d:4,5-d']-bis(1,3)dioxole-4-yl)methanol (1.06 g, 1.01 mmol (Example 27)) was added to a solution of trimethyl silylchloride (0.767 mL, 6.07 mmol) and sodium iodide (0.91 g, 6.07 mmol) in acetonitrile (50 mL) and stirred for ten minutes. Saturated sodium thiosulfate (30 mL) was added, followed by diethylether (70 mL), and the mixture was stirred for 10 minutes. The phases were separated and the organic phase was washed with water (30 mL). The organic phase was diluted with more ether (100 mL), since crystals had started to form in the funnel. The solution was kept in the freezer over night after drying (MgSO$_4$) and filtration. The crystals formed were removed (impurity) and the solution evaporated to dryness. The product was purified by dissolving the substance at room temperature in diisopropyl ether (E. Merck 118867, 30 mL), followed by bubbling with helium. The flask was stoppered and put in the refrigerator for two and a half hours. The product was collected by filtration (glass sinter no. 3), and the mother liquor was evaporated to approximately half the volume. The total yield after collecting the second crop was 640 mg (0.621 mmol, 61%).

$^1$H NMR (300 MHz, CDCl$_3$) δ: 1.23 (t), 1.51 (s), 3.55 (s), 4.11 (q), 5.34 (s).

$^{13}$C NMR (75 MHz, CDCl$_3$) δ: 169.09, 140.810, 139.50, 117.81, 107.65, 95.37, 61.18, 35.71, 30.70, 25.38, 14.11.

MS (Thermospray): M$^+$+23 (Na) 1053.

EXAMPLE 43

Tris(8-dimethylaminocarbonylthio-2,2,6,6-tetramethylbenzo[1,2-d:4,5-di bis(1,3)dioxole-4-yl)methanol

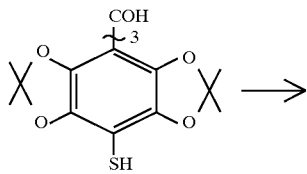

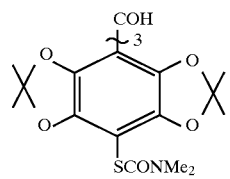

Tris(8-mercapto-2,2,6,6-tetramethylbenzo[1,2-d:4,5-d']-bis (1,3)dioxole-4-yl)methanol (1.00 g, 1.27 mmol (Example 31)) was added to an oxygen free (argon bubbling five min.) solution of K$_2$CO$_3$ (5.00 g) and dimethylcarbamoyl chloride (Fluka 39871, 0.367 mL, 4.0 mmol). A sample taken after forty five minutes, and controlled by $^1$H NMR, showed complete consumption of the substrate. The solution was filtered and evaporated. The crude product was 93% pure according to HPLC (C8, CH$_3$CN:H$_2$O, (3:1), 254 nm).

The substance was dissolved in diethylether (30 mL, dry, sodium benzophenone ketyl) and ultrasonicated for five minutes, followed by rotation at 35° C. for five minutes on a rotavapor at normal pressure. Cooling in the freezer for thirty minutes gave greyish crystals. Yield 0.580 g (0.579 mmol, 45.6%).

$^1$H NMR (300 MHz, CDCl$_3$) δ: 1.54 (s), 3.3 (bd), 4.20 (bs).

$^{13}$C NMR (75 MHz, CDCl$_3$) δ: 163.02, 142.80, 138.78, 118.05, 113.52, 92.07, 72.63, 37.01, 25.45.

MS (Thermospray): W$^+$+23 (Na) 1024.

EXAMPLE 44

Tris(2,2,6,6-tetramethylbenzo[1,2-d:4,5-d']bis(1,3)dioxole-4-yl)methanol

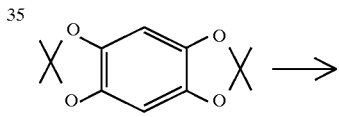

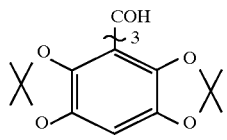

2,2,6,6-Tetramethylbenzo[1,2-d:4,5-d']bis(1,3)dioxole (17.570 g, 79.0 mmol (Example 5)) was dissolved in THF (300 mL, sodium benzophenone ketyl) and cooled to -20° C. with an ethanol/dry ice bath while maintaining an argon atmosphere. n-Butyl lithium (37.8 mL, 2.5M in hexane, 95.0 mmol) was added with a syringe, and the resulting mixture was allowed to reach room temperature. The mixture was recooled to -20° C. and dimethyl carbonate (2.37 g, 2.20 mL, 26.0 mmol) was added. The cooling bath was removed and the reaction mixture was stirred at room temperature for 3.5 hours. The mixture was then poured onto ice/water containing HOAc (2%) and extracted with diethyl ether (2×300 ml). The organic phase was washed with water (2×100 mL) and dried (Na$_2$SO$_4$). The solvent was evaporated and the product triturated with petroleum ether. Yield 13.56 g (74.4%)

$^1$H NMR (CDCl$_3$, 300 MHz) δ: 6.26 (s, arom. H, 3H), 1.48 (s, CH$_3$, 36H), 4.28 (s, OH, $^1$H).

$^{13}$C NMR (CDCl$_3$, 75 MHz) δ: 140.10, 139.00, 116.71, 112.57, 91.64, 72.69, 25.38.

MS (Thermospray): M$^+$+23 (Na) 715.

EXAMPLE 45

Tris(8-ethyloxycarbonylthio-2,2,6,6-tetramethylbenzo[1,2-d:4,5-d']bis(1,3)dioxole-4-yl)methanol

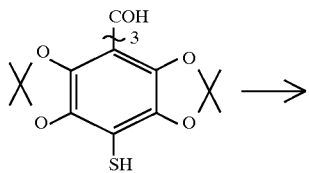 → 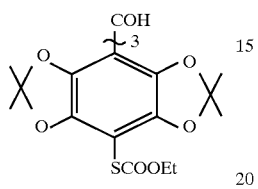

Tris(8-mercapto-2,2,6,6-tetramethylbenzo[1,2-d:4,5-d']bis(1,3)dioxole-4-yl)methanol (1.000 g, 1.269 mmol Example 31) was added to a solution of acetonitrile (75 mL, argon bubbled) and potassium carbonate (6.0 g). ClCO$_2$Et (0.725 mL, 8.00 mmol) was added and the resulting mixture was vigourously stirred for 30 minutes. An NMR sample showed complete conversion at this time. The mixture was filtered and evaporated. The pure product was obtained by chromatography on a silica column eluting with ethyl acetate:heptane 1:1. Yield 1.26 g (98.7%).

$^1$H NMR (CDCl$_3$, 300 MHz) δ: 4.26 (q, CH$_2$, 6H), 4.21 (s, COH, $^1$H), 1.54 (s, CH$_3$, 36H), 1.30 (t, CH$_3$, 9H).

$^{13}$C NMR (CDCl$_3$, 75 MHz) δ: 166.18, 142.30, 138.80, 118.35 113.70, 91.26, 72.51, 64.09, 25.42, 14.22.

MS (Thermospray): M$^+$+23 (Na) 1027.

EXAMPLE 46

Tris(8-ethyloxycarbonylthio-2,2,6,6-tetramethylbenzo[1,2-d:4,5-d']bis(1,3)dioxole-4-yl)methyl

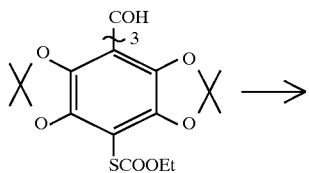 → 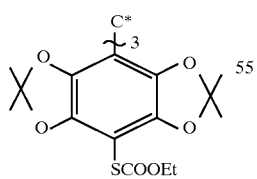

Tris(8-ethyloxycarbonylthio-2,2,6,6-tetramethylbenzo[1,2-d:4,5-d']bis(1,3)dioxole-4-yl)methanol (0.100 g, 0.099 mmol, Example 45) was dissolved in THF (5 mL, sodium benzophenone ketyl) and SOCl$_2$ (0.073 mL, 0.998 mmol) was added. The mixture was stirred for 3 hours and then evaporated under argon. More THF (3×50 mL, sodium benzophenone ketyl) was added and evaporated after each addition. The residue was dissolved in THF (50 mL, sodium benzophenone ketyl) and bCl$_3$ (955 mL, 0.998 mmol, 1M soln. in CH$_2$Cl$_2$) and stirred for 15 minutes, when SnCl$_2$ (0.189 g, 0.999 mmol) was added. The mixture was stirred for 10 minutes and zinc (0.653 g, 9.985 mmol, specially activated by p.a. HCl (2M), water, ethanol, ether, high vacuum drying 250° C. the same day)) was added. The reaction mixture was worked up after 3 hours stirring, by diluting with dry, oxygen-free diethyl ether (300 mL), extracting with NaOH (2×50 mL, 2M, oxygen free) and filtering the solution through a silica column, eluting with ether. Yield 0.058 g,(0.0594 mmol 60%).

ESR (THF, 200 G): Linewidth 109 mG (one wide line containing 70 resonances).

Overhauser enhancements (THF, 548.9 MHz, 200 G): 9 mW 12 enhancement, 18 mW 25 enhancement.

EXAMPLE 47

Tris(8-tertbutylcarbonylthio-2,2,6,6-tetramethylbenzo[1,2-d:4,5-d']bis(1,3)dioxole-4-yl)methanol

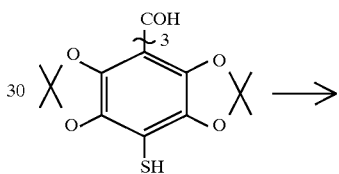 → 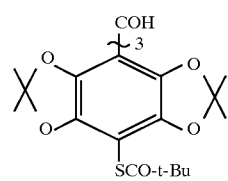

Tris(8-mercapto-2,2,6,6-tetramethylbenzo[1,2-d:4,5-d']bis(1,3)dioxole-4-yl)methanol (1.000 g, 1.268 mmol, Example 31), pyridine (0.620 mL, 7.606 mmol) and N,N-dimethylamino-pyridine (catalytic amount) were added to degassed (argon bubbled) acetonitrile (50 mL) and cooled close to the freezing point. 2,2-Dimethylpropanoic acid chloride (0.940 mL, 7.606 mmol) was added with a syringe, and the reaction mixture was allowed to reach room temperature over a period of 4 hours. The solvent was evaporated and the residue was dissolved in diethyl ether (200 mL). The ether was extracted with NaH$_2$PO$_4$ (50 mL, sat.), HCl (50 mL, 1M), NaH$_2$PO$_4$ (50 mL, sat.) and NaCl (50 mL, sat.) and dried (Na$_2$SO$_3$). Yield after filtration and evaporation: 1.00 g (0.9604 mmol, 75.7%). The compound was taken to analyical purity by dissolving in diisopropyl ether (80 mL) at room temperature with the help of ultrasound. Cooling in the refrigerator for 30 minutes gave 0.29 g (0.2785 mmol, 22.0%) of the pure compound.

$^1$H NMR (CDCl$_3$, 300 MHz) δ: 4.21 (s, CH, $^1$H), 1.53 (s, CH$_3$, 36H), 1.30 (s, CH$_3$, 36H).

$^{13}$C NMR (CDCl$_3$, 75 MHz) δ: 200.00, 142.05, 138.87, 118.01,

MS (Thermospray): M$^+$+23 (Na) 1063.

EXAMPLE 48

Tris(8-tertbutylcarbonylthio-2,2,6,6-tetramethylbenzo[1,2-d:4,5-d']bis(1,3)dioxole-4-yl)methyl

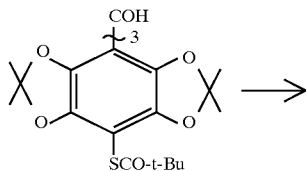

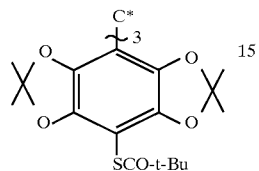

Tris(8-tertbutylcarbonylthio-2,2,6,6-tetramethylbenzo[1,2-d:4,5-d']bis(1,3)dioxole-4-yl)methanol (0.0957 g, 0.0919 mmol, Example 47) was dissolved in THF (25 mL, argon atmosphere., potassium benzophenone ketyl dried), and $BF_3.OEt_2$ (0.5 mL, 48% in diethyl ether, Fluka) was added. After stirring for 5 minutes $SnCl_2$ (0.1249 g, 0.659 mmol) was added followed by a gradual change in color to light brown. Zinc (0.5 g, 7.646 mmol) was added 1.5 hours after the $SnCl_2$. Two hours later the color had changed to green. A sample taken (after letting the Zn settle) with a gas tight syringe showed a large Overhauser enhancement. The reaction mixture was poured onto a column consisting of three layers; top layer $SiO_2$, intermediate layer $SiO_2$ and $K_2CO_3$ 1:1 and bottom layer $SiO_2$. The $K_2CO_3$ binds the $BF_3.OEt_2$, which has to be removed to avoid destabilizing the corresponding cation radicals. Yield: 0.079 g (0.07713 mmol, 83.9%).

ESR (THF, 200 G): Linewidth 109 mG, one unresolved line.

Overhauser enhancements (THF, 548.9 MHz, 200 G, conc.<1 mM): 9 mW 96 enhancement, 18 mW 114 enhancement.

EXAMPLE 49

Tris(8-methylcarbonylthio-2,2,6,6-tetramethylbenzo[1,2-d:4,5-d']bis(1,3)dioxole-4-yl)methanol

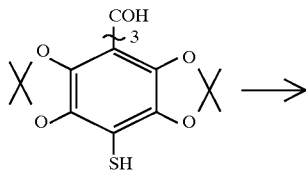

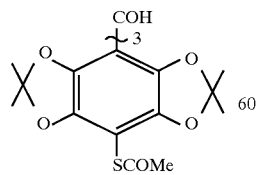

Tris(8-mercapto-2,2,6,6-tetramethylbenzo[1,2-d:4,5-d']bis(1,3)dioxole-4-yl)methanol (1.000 g, 1.268 mmol, Example 31), acetyl chloride (0.540 mL, 7.605 mmol) and $K_2CO_3$ (2.0 g, 1.447 mmol) were added to $CH_3CN$ (25 mL, degassed with argon). An NMR sample showed complete reaction after 90 minutes. The solvent was evaporated and the product was purified by flash chromatography ($SiO_2$, 230–400 mesh, i.d.35 mm, 40 cm length) followed by crystallization in diisopropyl ether (50 mL). The product was dissolved at room temperature with the help of ultrasound. The product was collected after 2 hours in the freezer. Yield: 0.61 g (0.667 mmol, 52.6%)

$^1$H NMR ($CDCl_3$, 300 MHz) δ: 2.42 (s, $CH_3$, 9H), 1.55 (s, $CH_3$, 36H).

$^{13}$C NMR ($CDCl_3$, 75 MHz) δ: 190.58, 141.81, 138.86, 118.32, 113.55, 91.44, 72.50, 29.97, 25.42.

MS (Thermospray): $M^+$+23 (Na) 937.

EXAMPLE 50

Tris(8-methylcarbonylthio-2,2,6,6-tetramethylbenzo[1,2-d:4,5-d']bis(1,3)dioxole-4-yl)methyl

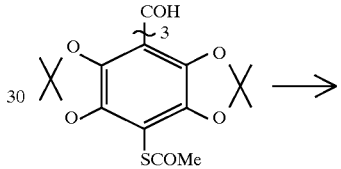

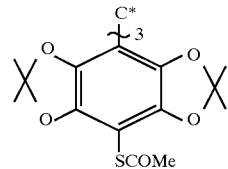

Tris(8-methylcarbonylthio-2,2,6,6-tetramethylbenzo[1,2-d:4,5-d']bis(1,3)dioxole-4-yl)methanol (0.0915 g, 0.0999 mmol, Example 49) was dissolved in THF (25 mL, argon atmosphere, potassium benzophenone ketyl dried), and $BF_3.OEt_2$ (0.5 mL, 48% in diethyl ether Fluka) was added. A temporary red color was seen when the drops were hitting the surface of the solution. After stirring for 5 minutes, $SnCl_2$ (0.1249 g, 0.659 mmol) was added followed by a gradual change in color to light brown. Zinc (0.500 g, 7.646 mmol, prepared as described above) was added 1.5 hours after the $SnCl_2$. Two hours later the color had changed to green. A sample taken (after letting the Zn settle) with a gas tight syringe showed an enormous Overhauser enhancement. The reaction mixture was poured onto a column consisting of three layers: top layer $SiO_2$ intermediate layer $SiO_2$ and $K_2CO_3$, 1:1 and bottom layer $SiO_2$. The $K_2CO_3$ binds the $BF_3$. $OEt_2$, which has to be removed to avoid destabilizing the corresponding cation radicals. Yield: 0.0720 g (0.0802 mmol, 80.3%, unknown radical content).

ESR (THF, 200 G): One line;Linewidth 117 mG.

Overhauser enhancements (THF, 548.9 MHz, 200 G, <1 mM):11 mW 89 enhancement, 18 mW 110 enhancement.

EXAMPLE 51

Bis(8-mercapto-2,2,6,6-tetramethylbenzo[1,2-d:4,5-d']bis(1,3)dioxole-4-yl)ketone

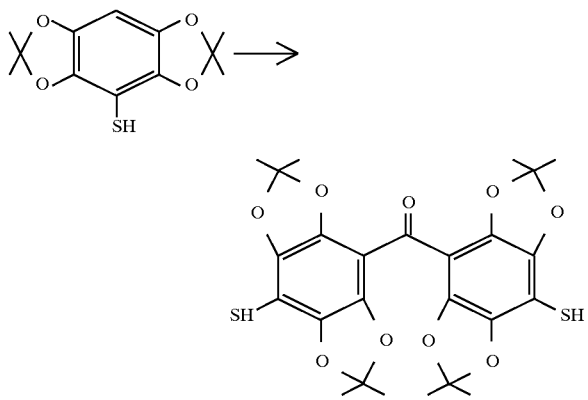

The title compound was isolated as a by product in the reaction between diethyl carbonate and the lithium salt of 8-mercapto-2,2,6,6-tetramethylbenzo[1,2-d:4,5-d']bis(1,3) dioxole, see Example 31.

$^1$H NMR (CDCl$_3$, 300 MHz) δ: 3.46 (s, SH, 2H), 1.63 (s, CH$_3$, 24H).

$^{13}$C NMR (CDCl$_3$, 75 MHz) δ: 183.42, 138.96, 137.90, 119.55, 106.84, 100.36, 15.24.

MS (Thermospray): M$^+$+23 (Na) 557.

EXAMPLE 52

Benzo[1,2-d:4,5-d']bis(1,3)dioxole-2,6-dispirocyclohexane

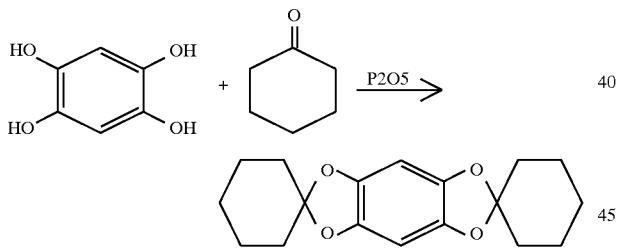

1,2,4,5-Tetrahydroxybenzene (5.00 g, 35.00 mmol, Example 4) was dissolved in THF (200 mL) and cyclohexanone (13.0 mL, 140.00 mmol) was added in one portion. P$_2$O$_5$ was then added in small portions under efficient stirring. After addition was completed the temperature was increased to 80° C. for 4 hours. One large ball was formed in the flask during this time. After cooling to room temperature the ball was broken up and the reaction mixture was poured on a mixture of ice (210 g) and NaOH (250 mL, 2M). Ether (100 mL) was added and the phases separated. The aqueous was extracted with ether (2×50 mL). The combined organic phase was dried (Na$_2$SO$_4$), filtered and evaporated. The product was dissolved in MeOH (20 mL), heated, filtered, cooled and the product was collected by filtration. Yield 1.70 g (16%).

$^1$H NMR (CDCl$_3$, 300 MHz) δ: 6.35 (s, CH arom., 2H), 1.87 (t, CH$_2$, 8H), 1.69 (t, CH$_2$, 8H), 1.47 (m, CH$_2$, 4H).

$^{13}$C NMR (CDCl$_3$, 75 MHz) δ: 140.37, 118.54, 92.80, 34.84, 24.57, 23.13.

EXAMPLE 53

Tris(benzo[1,2-d:4,5-d']bis(1,3)dioxole-2,6-dispirocyclohexane)methanol

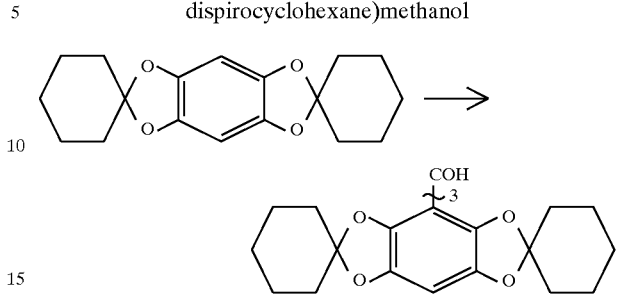

Benzo[1,2-d:4,5-d']bis(1,3)dioxole-2,6-dispirocyclohexane (2.00 g, 6.60 mmol, Example 52) was dissolved in diethyl ether (80 ml, dried over Al$_2$O$_3$) and cooled to -10° C. in an ice acetone bath. n-Butyl lithium (3.70 mL, 2.5M in hexane) was added with a syringe over a period of five minutes. The mixture was stirred at the same temperature for 1 hour and overnight at room temperature. Diethyl carbonate (0.28 mL, 2.4 mmol) was added at room temperature and the mixture immediately changed color to red-brown. After stirring for 1 hour it was poured on ice/water (100 mL). The organic phase was separated and the waterphase extracted with CH$_2$Cl$_2$ (100 mL). To facilitate the phase separation HCl (20 mL, 1M) was added. The combined organic phase was dried (MgSO$_2$), filtered and evaporated. Yield 1.90 g (31%).

$^{13}$C NMR (CDCl$_3$, 75 MHz): 140.1, 138.9, 117.5, 91.5, 72.5, 34.6, 24.6, 22.9.

EXAMPLE 54

1,2,4,5-Tetrahydroxybenzene

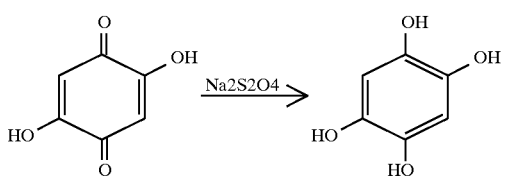

2,5-Dihydroxy-1,4-benzoquinone (4.00 g, 28.55 mmol) was suspended in water (50 ml, distilled) followed by Na$_2$S$_2$O$_4$ (10.00 g, 57.47 mmol) and HCl (5.5 g, 55.75 mmol conc. soln.). The mixture was stirred 30 min. at room temperature and evaporated to dryness. The residue was washed with THF (40 ml) and filtered. The THF was evaporated yielding 2.00 g (14.07 mmol, 49.3%) of the title substance.

$^1$H NMR (DMSO6, 300 MHz) δ: 7.59 (bs, OH, 4H), 6.23 (s, CH, 2H).

$^{13}$C NMR (DMSOd6, 75 MHz) δ: 136,96, 104.65.

EXAMPLE 55

1,2,4,5-Tetrahydroxybenzene

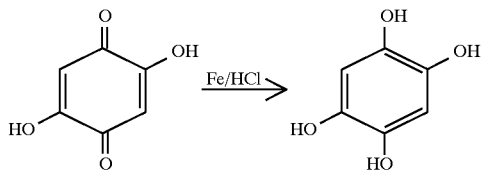

2,5-Dihydroxy-1,4-benzoquinone (10.00 g, 71.43 mmol) was suspended in water (200 ml, distilled) followed by HCl (6 mL, 142–86 mmol, conc.). Iron (4.00 g, 71.43 mmol, powder) was added and the mixture was stirred 30 minutes at room temperature. The solution was filtered and the solution evaporated to dryness. The product was isolated as a grey brown powder containing some iron complexes. Yield 14.80 g. The product is used as such in the reaction with acetone and $P_2O_5$ (Example 5) with no negative effects.

$^1$H NMR (DMSOd$_6$, 300 MHz) δ: 6.9–3.0 (broad, OH, 4H), 6.21 (broad s, CH, 2H).

$^{13}$C NMR (DMSOd$_6$, 75 MHz) δ: 136,96, 104.65.

EXAMPLE 56

Tris(2,2,6,6-tetramethylbenzo[1,2-d:4,5-d']bis(1,3) dioxole-4-yl)methanol

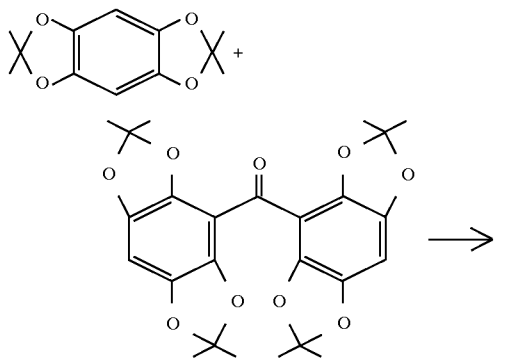

2,2,6,6-Tetramethylbenzo[1,2-d:4,5-d']bis(1,3)dioxole (8.80 g, 40.00 mmol, Example 5) was dissolved in THF (100 mL) and cooled to −20° C. n-Butyllithium (25.0 mL, 40.0 mmol, 1.6M) was added and the temperature was adjusted to ambient temperature over a period of 30 minutes and then recooled to −20° C. Bis(2,2,6,6-tetramethylbenzo-(1,2-d:4,5-d']bis(1,3)dioxole-4-yl)ketone (18.80 g, 39.83 mmol, Example 57) was added and the temperature was once more adjusted to room temperature and the mixture was stirred for 18 hours. The mixture was then poured on water/AcOH (100 mL, 2% AcOH) and extracted with diethyl ether (2×100 mL). The organic phase was washed with water (2×100 ml) and dried (Na$_2$SO$_4$). The solvent was evaporated and the product was washed with petroleum ether (20 mL, 40–60° C.). Yield 10.80 g (64.1%). Spectral data see example 44.

EXAMPLE 57

Bis(2,2,6,6-tetramethylbenzo[1,2-d:4,5-d']bis(1,3) dioxole-4-yl)ketone

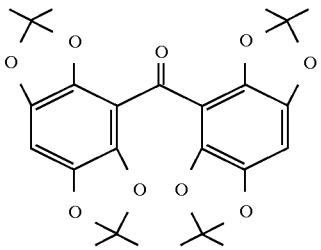

2,2,6,6-Tetramethylbenzo[1,2-d:4,5-d']bis(1,3)dioxole (400.0 g, 1.80 mol, Example 5) was dissolved in THF (6 L, dried, perhaps incompletely) and cooled to −20° C. with a cryostat while maintaining a nitrogen atmosphere. n-Butyl lithium (1350 mL, 1.6M in hexane, 2.16 mol) was added with a dropping funnel, and the resulting mixture was allowed to reach room temperature. The mixture was recooled to −20° C. and dimethyl carbonate (47.0 mL, 0.56 mol) was added. The cryostat was turned off and the reaction mixture was allowed to reach room temperature over night while stirring. Water (3.0 L, containing 2% HOAc) was added to the reaction mixture, and the resulting solution was extracted with diethyl ether (2×3.0 1). The organic phase was washed with water (2× 1.0 L) and dried (Na$_2$SO$_4$, K$_2$CO$_3$). The solvent was evaporated and the product triturated with petroleum ether (boiling range 40°–60° C.). Yield after separation by recrystallisation in MeOH/H$_2$O: 50.0 g (106.0 mmol, 18.9% relative to dimethyl carbonate).

$^1$H NMR (CDCl$_3$, 300 MHz) δ: 6.42 (s, CH aromatic, 2H), 1.60 (s, CH$_3$, 24H).

$^{13}$C NMR (CDCl$_3$, 75 MHz) δ: 184.55 (C=O), 140.51, 139.43, 118.86, 109.13, 95.89, 25.56.

MS (Thermospray): M$^+$+23 493.

EXAMPLE 58

Mono-(2,2,6,6-tetramethylbenzo[1,2-d:4,5-d']-bis(1, 3)dioxole-4-yl)-mono(phenyl)-mono(pyridin-4-yl) methanol

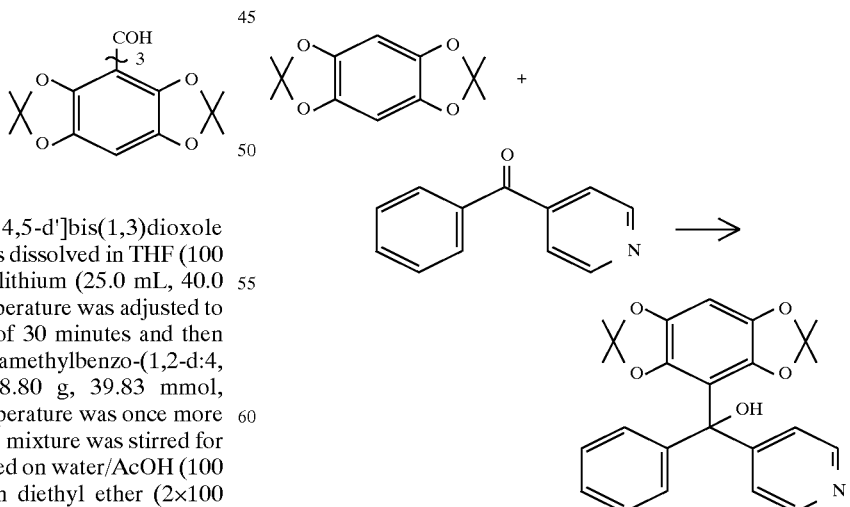

2,2,6,6-Tetramethylbenzo[1,2-d:4,5-d']bis(1,3)dioxole (3.030 g, 13.60 mmol, Example 5) was dissolved in THF (50 mL, sodium benzophenon ketyl) under N₂. The mixture was cooled to −78° C. n-Butyllithium (5.10 mL, 13.6 mmol, 2.68M in toluene) was added with a syringe during 5 minutes. 15 Minutes later the dry ice acetone cooling bath was excanged with a ice water bath and the reaction mixture was stirred for 1 hour. The mixture was recooled to −78° C. and phenyl pyridyl ketone (2.50 g, 13.60 mmol) dissolved in THF (10 mL, Na benzophenone ketyl) was added dropwise. One hour later the cooling bath was exchanged with a ice/water bath and the reaction was allowed to reach room temperature and stirred for 3 days. The THF was washed with NaH₂O₄ (2×50 mL, 1.25M), dried (Na₂SO₄) and evaporated yielding 5.10 g crude product. Analytically pure compound was obtained by dissolving the crude product in a mixture of hot CH₃CN and THF and crystallizing. Yield 0.826 g,(2.04 mmol 15%).

¹H NMR (CDCl₃, 300 MHz) d 8.52 (m, CH pyridine, 2H, AA'in AA'XX'spin system), 7.26 (m, CH pyridin, 2H, XX'in AA'XX'spin system), 6.31 (s, CH, ¹H), 4.61 (s, OH, ¹H), 1.47 (s, CH₃, 6H), 1.40 (s, CH₃, 6H).

¹³C NMR (CDCl₃, 75 MHz) δ: 153.90, 149.16, 143.79, 140.83, 137.41, 127.85, 127.80, 127.53, 122.92, 118.17, 113.41, 110.08, 92.67, 79.28, 25.21, 25.10 (two resonances at 25 ppm due to nonequivalence of methyl groups).

MS (Thermospray): M⁺+1 406.

EXAMPLE 59

Bis(8-methylthio-2,2,6,6-tetramethylbenzo[1,2-d:4,5-d']bis(1,3)dioxole-4-yl)ketone

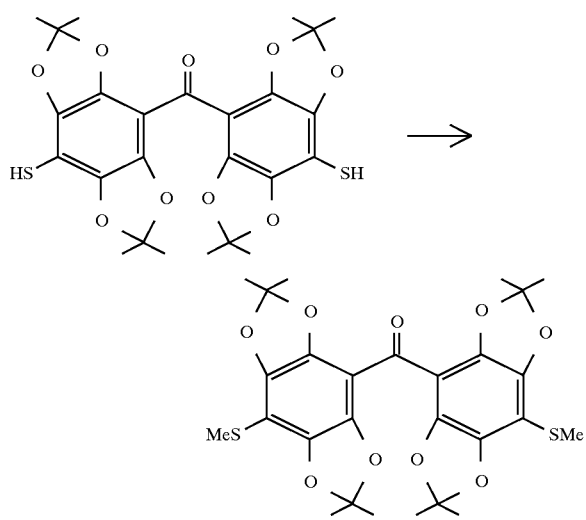

Bis-(8-Mercapto-2,2,6,6-tetramethylbenzo[1,2-d:4,5-d'] bis-(1,3)dioxole-4-yl)ketone (0.6000 g, 1.1236 mmol Example 51) was dissolved in a CH₃CN (50 mL) and cooled to 0° C. CH₃I (0.42 ml, 6.74 mmol) and K₂CO₃ (4.0 g) were added. The resulting mixture was stirred at room temperature for 70 minutes. Before filtering away the K₂CO₃, diethyl ether (50 ml) was added to ensure that all of the product was in solution. Filtration and evaporation yielded a quantiatative amount (0.630 g, 100%) of the pure title compound.

¹H NMR (CDCl₃, 300 MHz) δ: 2.42 (s, CH₃, 6H), 1.55 (s, CH₃, 24H).

¹³C NMR (CDCl₃,75 MHz) δ: 183.30, 140.15, 138.68, 118.94, 107.68, 105.49, 26.57, 25.34, 16.12.

MS (Thermospray) M⁺+23 (Na) 585, M⁺+39 (Ka) 601.

EXAMPLE 60

Bis(B-Methylmercapto-2,2,6,6-tetramethylbenzo[1,2-d:4,5-d']bis(1,3)dioxole-4-yl)-mono(2-methylmercapto-pyrimidin-5-yl)methanol

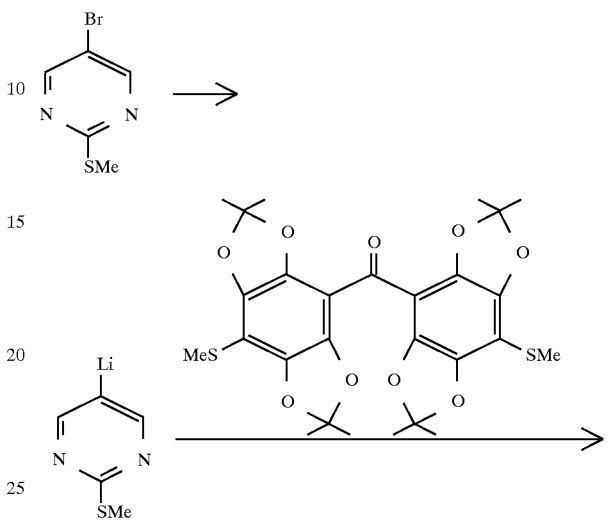

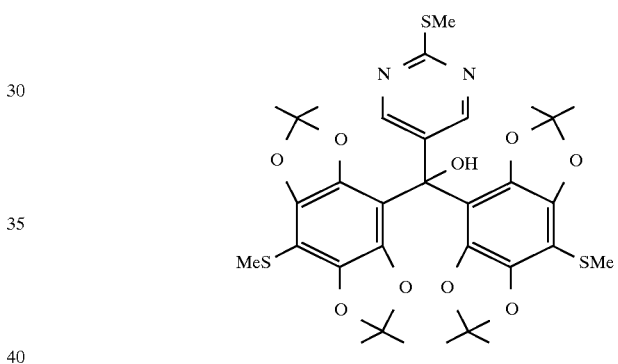

5-Bromo-2-methylthio-pyrimidine (0.250 g, 1.2195 mmol) was dissolved in THF (50 mL, sodium benzophenone ketyl) and cooled to −105° C. n-Butyl lithium (0.455 ml in toluene, 1.2195 mL) was added and the temperature was increased to −75° C. for 15 minutes and thereafter reduced to −105° C. Bis(8-methylthio-2,2,6,6-tetramethylbenzo[1,2-d:4,5-d']-bis(1,3)dioxole-4-yl)ketone (0.63146 g, 1.1236 mmol, Example 59) was added in solid form and the temperature was gradually increased to room temperature (removal of cooling bath). The mixture was stirred overnight, NaCl (15 mL, sat.) and diethyl ether (40 mL) were added and the phases separated after 5 minutes stirring. The organic phase was dried (MgSO₄) and evaporated yielding 0.59 crude product. Pure product was obtained by crystallization in diethyl ether followed by a second crystallization in diisopropyl ether. Yield 0.115 g (0.1669 mmol, 14.9%).

¹H NMR (CDCl₃, 300 MHz) δ: 8.53 (s, 2H), 4.54 (¹H, s), 2.55 (s, 3H), 2.41 (s, 6H), 1.49 (s, 24H).

¹³C NMR (CDCl₃, 75 MHz) δ: 171.12, 156.42, 141.21, 137.54, 131.33, 118.26, 110.75, 101.18, 73.90, 25.38, 25.29.

MS (Thermospray) M⁺+23 (Na) 711.

EXAMPLE 61

Tris(8-methylcarbonylthio-2,2,6,6-tetramethylbenzo[1,2-d:4,5-d']bis(1,3)dioxole-4-yl)methane

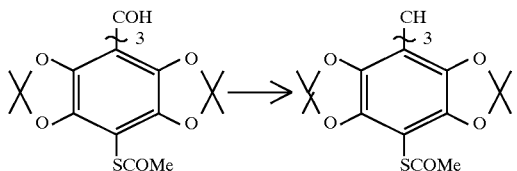

NaI (0.15972 g, 1.1256 mmol) and trimethylsilyl chloride (0.142 mL, 1.1256 mmol) were stirred in acetonitrile (50 mL). Tris(8-methylcarbonylthio-2,2,6,6-tetramethylbenzo-[1,2-d:4,5-d']bis(1,3)dioxole-4-yl)methanol (0.1286 g, 0.1407 mmol, Example 49) was added in solid form and the color of the solution became brownish. $Na_2S_2O_4$ (20 mL, sat.) was added after 60 minutes and the mixture was stirred 5 minutes before separation of the phases. The aqueous phase was extracted with diethyl ether (50 mL), and the combined organic phase was dried ($MgSO_4$) and evaporated, yielding 0.105 g (0.1168 mmol, 83%) of the title compound.

$^1$H NMR ($CDCl_3$, 300 MHz) δ: 5.42 (s, CH, $^1$H), 2.40 (s, $CH_3$, 9H), 1.53 (s, $CH_3$, 36H).

$^{13}$C NMR ($CDCl_3$, 75 MHz) δ: 191.16, 141.20, 139.66, 118.35, 108.81, 90.39, 31.01, 29.88, 25.34.

MS (Thermospray) M$^+$+23 (Na) 921.

EXAMPLE 62

Tris(8-tertbutylcarbonylthio-2,2,6,6-tetramethylbenzo[1,2-d:4,5-d']bis(1,3)dioxole-4-yl)methane

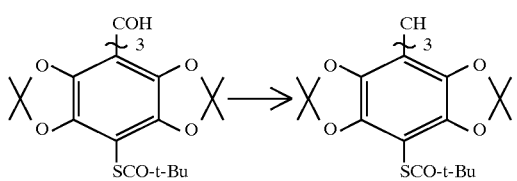

NaI (0.185 g, 1.2342 mmol) and trimethylsilyl chloride (0.156 mL, 1.2336 mmol) were stirred in acetonitrile (50 mL). Tris(8-tertbutylcarbonylthio-2,2,6,6-tetramethylbenzo-[1,2-d:4,5-d']bis(1,3)dioxole-4-yl)methanol (0.220 g, 0.2056 mmol, Example 47) was added in solid form and the color of the solution became brownish. $Na_2S_2O_4$ (20 mL, sat.) was added after 60 minutes and the mixture was stirred 5 minutes before separation of the phases. The aqueous phase was extracted with diethyl ether (50 mL), and the combined organic phase was dried ($MgSO_4$) and evaporated, yielding 0.105 g (0.1168 mmol, 83%) of the title compound. Tris(8-tertbutylcarbonylthio-2,2,6,6-tetramethylbenzo[1,2-d:4,5-d']bis(1,3)dioxole-4-yl) methane (0.205 g, 0.200 mmol, 97.3%).

$^1$H NMR ($CDCl_3$, 300 MHz) δ: 5.42 (s, CH, $^1$H), 1.51 (s, $CH_3$, 36H), 1.29 (s, $CH_3$, 27H).

$^{13}$C NMR ($CDCl_3$, 75 MHz) δ: 200.51, 141.45, 139.68, 117.99, 108.59, 90.78, 46.90, 31.03, 27.17, 25.34.

MS (Thermospray) M$^+$+23 (Na) 1047.

EXAMPLE 63

Bis(8-formyl-2,2,6,6-tetramethylbenzo[12-d:4,5-d'] bis(l3)dioxole-4-yl)-mono(2,2,6,6-tetramethylbenzo[1,2-d:4,5-d'ibis(1,3)dioxole-4-yl)methyl

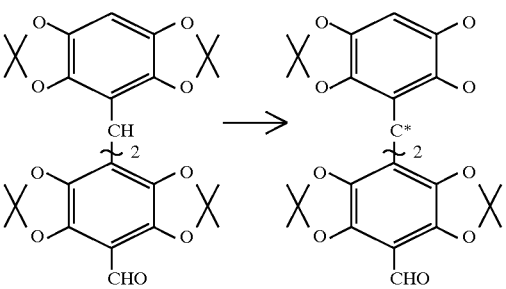

Bis(8-formyl-2,2,6,6-tetramethylbenzo[1,2-d:4,5-d']bis(1,3)dioxole-4-yl)-mono(2,2,6,6-tetramethylbenzo[1,2-d:4,5-d']bis(1,3)dioxole-4-yl)methane (0.100 g, 0.136 mmol) (from Example 23) was dissolved in a mixture of THF (40 mL, $Al_2O_3$) and DMSO (10 mL, mol. sieves.). tBuOK (0.0168 g, 0.150 mmol) was added and the resulting mixture was heated to 75° C. for 1 hour. The solution was dark green/black at this time. $I_2$ (0.038 g, 0.150 mmol) was added and a sample was taken after 1 minute and an Overhauser enhancement experiment was done; a 19 times enhancement was measured at 5 W irradiation (200 G, 548.9 MHz, THF). After dilution with ether (100 mL), extraction with $Na_2S_2O_3$ (sat. 40 mL), drying ($Na_2SO_4$) and evaporation, an Overhauser enhancement of 50 at 5 W irradiation was obtained.

ESR (200 G, 548.9 MHz, three lines, THF): Linewidth 85 mG, $a_H$ 175 mG.

EXAMPLE 64

Tris(8-formyl-2,2,6,6-tetramethylbenzo[1,2-d:4,5-d'] bis-(1,3)dioxole-4-yl)methyl

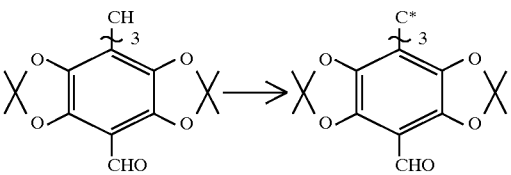

Tris(8-formyl-2,2,6,6-tetramethylbenzo[1,2-d:4,5-d']bis-(1,3)dioxole-4-yl)methane (0.104 g, 0.134 mmol, Example 23) was dissolved in a mixture of DMSO (10 mL), and diethyl ether (30 mL). NaH (0.0037 g, 0.134 mmol, 80% in oil) and KOtBu (catalytic amount) were added and the resulting mixture was stirred under argon. Samples (about 50 mL) were taken with irregular intervals and quenched with $DCl/D_2O$ (10% DCl) under argon. After 2 hours and 15 min. the $^1$H NMR measurements of the evaporated diethyl ether extact from the quench showed 37% deuteration (anion formation). 18 Hours after the start the deuteration level was 70%. The calculated amount left in the flask was 78 mg at this time. $I_2$ (0.056 g, 2 equivalents) was added and the reaction mixture was worked up after 2 minutes reaction time. The mixture was diluted with diethyl ether (50 mL) and washed with $Na_2S_2O_3$ (sat. 2×25 mL), dried ($Na_2SO_4$) and evaporated yielding 0.030 g (40.8%). The radical content was 60% according to $^1$H NMR (Evans method) and 64% by HPLC (Kromasil 10 mm, C8, 250 mm long, i.d. 4.6 mm, CH₃CN:H₂O 70:30 to 100:0 gradient 20 minutes, UV 254 nu. detection).

Overhauser enhancements (200 G. 548.9 MHz, 5.9 mM in THF): 9 mW 51, 18 mW 88, 5W 251.

The HPLC chromatogram of the tris(8-formyl-2,2,6,6-tetramethylbenzo[1,2-d:4,5-d']bis(1,3)dioxole-4-yl)methyl radical showed a peak at 5.93 s corresponding to the radical and a peak at 6.58 s corresponding to the starting material. The HPLC separated materials also showed distinct UV spectra.

EXAMPLE 65

8-Mercapto-2,2,6,6-tetramethylbenzo[1,2-d:4,5-d']bis-(1,3)dioxole-4-yl)carboxylic acid ethylester

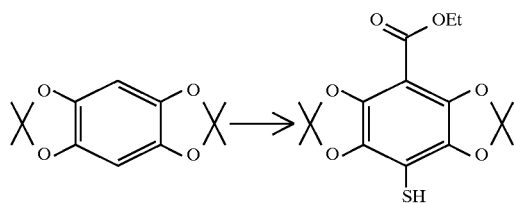

2,2,6,6-Tetramethylbenzo[1,2-d:4,5-d]bis(1,3)dioxole (4.00 g, 18.00 mmol, Example 5) was dissolved in diethyl ether (50 mL, sodium benzophenone ketyl), n-butyl lithium (7.56 mL, 18.90 mmol, 2.5M in hexane) was added and the resulting solution was refluxed 30 minutes. More diethyl ether (30 mL) was added and the mixture was cooled to −70° C. and S₈ (0.5759 g, 17.96 mmol) was added and the temperature was increased to 0° C. THF (100 mL) was added 2 hours after increasing the temperature and the mixture was recooled to −70° C. n-Butyl lithium (8.64 mL, 18.0 mmol) was added and the temperature was increased to 0° C. One hour and forty five minutes later the slurry was filtered through a glass sinter (no. 4) at one of the three necks of the reaction flask. The white crystals (lithium salt) were washed with diethyl ether (50 mL, sodium benzophenone ketyl) under argon, and the ether removed by filtration through the sinter. Weighing of the flask with the dry lithium salt indicated that there remained around 8 mmol lithium salt in the flask. THF (70 mL) was added to the salt, the mixture cooled to 0° C., and diethyl carbonate (0.654 mL, 5.4 mmol) was cannulated into the solution and the mixture was left overnight to reach room temperature. The mixture was diluted with ether (300 mL), extracted with NaH₂PO₄ buffer (2×50 mL, sat.), dried (MgSO₄) and evaporated yielding the title compound, 1.60 g (4.90 mmol, 90.7% native to diethyl carbonate).

¹H NMR (CDCl₃, 300 MHz) δ: 4.36 (k, CH2, 2H), 1.70 (s, CH₃, 12H), 1.35 (t, CH₃, 3H).

MS (EI) M⁺ 326, 280, 224.

EXAMPLE 66

Tris(2-methoxycarbonylthien-4-yl)methane

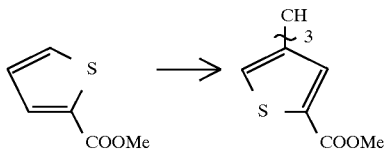

Dry powdered AlCl₃ (47.12 g, 0.353 mol) was placed in a three-necked flask and a mixture of thiophene-2-carboxylic acid methyl ester (20.0 g, 0.141 mol) and chloroform (47.8 g, 32.3 ml, 0.40 mol) was added rapidly but dropwise. After heating at reflux temperature for 1.5 h, the mixture was hydrolyzed with 50% aqueous HCl (100 ml). Extraction with CH₂Cl₂ (3×150 ml) followed by drying of the combined organic phases (MgSO₄) and evaporation gave the crude product as a red solid. Filtering through a short silica column using petroleum ether/EtOAc as the eluant, followed by evaporation gave the title compound as a light yellow solid. Yield: 17.9 g (88%)

¹H NMR (CDCl₃, 300 MHz) δ: 7.56 (CH, 3H, d, J=1.6 Hz), 7.12 (CH, 3H, m), 5.50 (CH, ¹H, s), 3.84 (OCH₃, s, 9H).

¹³C NMR (CDCl₃, 75 MHz) δ: 162.31 (C=O), 143.79 (quart. C—CO₂Me), 134.56 (quart. C—CH), 133.59 (thienyl CH), 129.03 (thienyl CH), 52.08 (OCH₃).

EXAMPLE 67

Tris(2-methoxycarbonylthien-4-yl)methyl

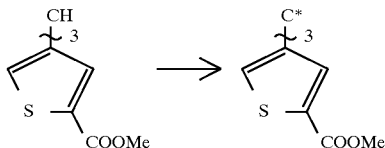

Tris(2-methoxycarbonylthien-4-yl)methane (0.218 g, 0.5 mmol, Example 66) was dissolved in dry THF (25 ml) under an argon atmosphere. Solid KOtBu (0.055 g, 0.5 mmol) was added, the solution was stirred for 30 min. and I₂ (0.127 g, 1.0 mmol) was added.

The Overhauser effect was measured directly on this solution and found to be 4 at 5 W.

EXAMPLE 68

Tris(8-methylsulfonyl-2,2,6,6-tetramethylbenzo[2-d:4,5-d']-bis(1,3)dioxole-4-yl)methyl

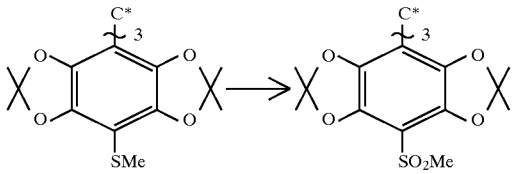

Tris(8-methylthio-2,2,6,6-tetramethylbenzo[1,2-d:4,5-d']-bis(1,3)dioxole-4-yl)methyl (0.163 g, 0.20 mmol, approximately 15% radical content, Example 8) was dissolved in CH₂Cl₂ (10 ml) under an argon atmosphere and 3-chloroperbenzoic acid (0.207 g, 1.20 mmol) was added. After stirring for 15 minutes, ESR spectroscopy of the reaction mixture showed a new radical.

ESR: 6 lines with a $_H$: 290 mG, linewidth: 113 mG. Overhauser enhancement: 5 at 5W.

EXAMPLE 69

Bis(8-methyloxycarbonyl-2,2,6,6-tetramethylbenzo[12-d:4,5-d']bis(1,3)dioxole-4-yl)-mono(8-cyano-2,2,6,6-tetramethylbenzo[1,2-d:4,5-d']bis(1,3)dioxole-4-yl)methanol

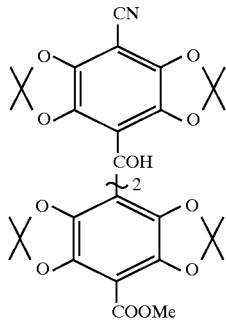

The title compound was isolated as a by product in the synthesis of tris(8-methoxycarbonyl-2,2,6,6-tetramethylbenzo[1,2-d:4,5-d']bis(1,3)dioxole-4-yl)methanol (Example 15) in a yield of about 5%.

$^1$H NMR (CDCl$_3$, 300 MHz) δ: 3.84 (s, 6H), 1.50 (s, CH$_3$, 36 H).

$^{13}$C NMR (CDCl$_3$, 75 MHz) δ: 163.43, 141.70, 140.57, 139.29, 139.07, 119.92, 118.50, 116.34, 114.52, 11.58, 99.30, 78.49, 72.51, 51.89, 25.54, 25.48.

MS (EI) M$^+$ 833.

IR (KBr, cm$^{-1}$): 3000 (CH), 2240 (CN), 1760 (CO).

EXAMPLE 70

Bis(2,2,6,6-tetramethylbenzo[1,2-d:4,5-d']bis(1,3)dioxole-4-yl)-mono(1,2,3-trimethoxy-5-phenyl)methanol

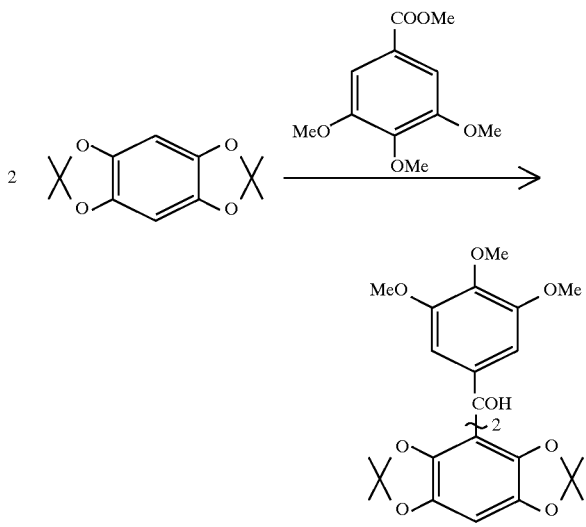

2,2,6,6-Tetramethylbenzo[1,2-d:4,5-d']bis(1,3)dioxole (2.22 g, 10.0 mmol (Example 5)) was dissolved in THF (50 mL, sodium benzophenone ketyl) and cooled to −20° C. n-Butyl lithium (4.80 mL, 12.0 mmol, 2.5M in toluene) was added and the temperature increased to ambient temperature. The mixture was recooled to −20° C. and 3,4,5-trimethoxybenzoic acid methyl ester (1.13 g, 5.0 mmol) dissolved in THF(10 mL) was added and the resulting mixture was stirred at ambient temperature overnight. The solution was poured onto acidic water (2% AcOH, 50 mL) and extracted with diethyl ether (2×50 mL). The organic phase was washed with water (2×50 mL), dried (Na$_2$SO$_4$) and evaporated yielding 3.10 g (4.7 mmol, 97%) of the title compound.

$^1$H NMR (CDCl$_3$, 300 MHz) δ: 6.75 (s, arom. H, 2H), 6.28 (s, arom. H, 2H), 3.83 (s, OCH$_3$, 3H), 3.76 (s, OCH$_3$, 6H), 1.44 (s, CH$_3$, 24H).

$^{13}$C NMR (CDCl$_3$, 75 MHz) δ: 152.29, 140.33, 138.81, 138.25, 137.56, 117.07, 113.58, 105.52, 92.06, 76.77, 60.86, 56.16, 25.30, 25.19.

MS (Thermospray): MW++23 (Na) 661.

EXAMPLE 71

Tris(8-ethoxycarbonylmethylthio-2,2,6,6-tetramethylbenzo[1,2-d:4,5-d']bis(1,3)dioxole-4-yl)methyl

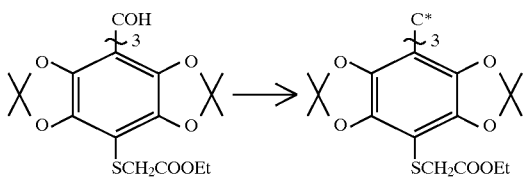

Tris(8-ethoxycarbonylmethylthio-2,2,6,6-tetramethylbenzo[1,2-d:4,5-d']bis(1,3)dioxole-4-yl)methanol (0.050 g, 0.048 mmol (Example 27)),was dissolved in dry THF (20 mL). Under Ar (g) BF$_3$.OEt (0.020 mL, 0.080 mmol) was added, and an intense blue color developed (formation of carbocation). After 1 h was added a complex of Chelex-100 and SnCl$_2$$^+$ i.e. Chelex-100-Sn$_2$$^+$ [0.50 g, 0.05 mequiv. of Sn$^{2+}$; (Preparation of the Chelex-100-Sn+-complex: 20 g (58 mequiv. of Na$^+$) of Chelex-100 was treated with 14 g (of SnCl$_2$.H$_2$O, 116 mequiv.) in water (100 mL). The solid material was filtered and washed with water (100 mL) and EtOH (500 mL) and ether (100 mL) and was then dried in a desiccator at 0.1 torr, yielding the dry complex (25 g).)], followed 15 min later by Zn dust (0.030 g, 0.450 mmol). The reaction mixture started to change to a brown color. The reaction mixtured was directly filtered through a 3 cm (i.d. 1 cm) glass column filled with SiO$_2$ (Merck, 0.043–0.060 mm) eluting with diethyl ether. The eluate was dried (Na$_2$SO$_4$), filtered and the solvent was evaporated, yielding a black crystalline mass (0.048 g, 95.8%).

Overhauser enhancement: 89 at 9 mW in THF at 1.84 mM, (concetration estimated by NMR-Evans method).

ESR spectrum: 7 lines, Linewidth 31 mG, a$_H$=62 mG

EXAMPLE 72

1,2,4,5-Tetratrimethylsilyloxybenzene

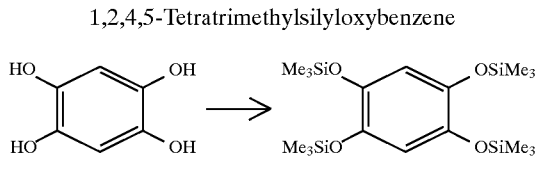

1,2,4,5-Tetrahydroxybenzene (14.20 g, 100.0 mmol (Example 4)) was dispersed in pyridine (100 mL) and diethyl ether (100 mL), and Me₃SiCl (70 mL, 645 mmol) was slowly added (heat evolved). After 3 hours the pyridiniumchloride was filtered off and the solvents of the filtrate (red) were evaporated, leaving a red oil, which was dissolved in ether, more solid material was filtered off, and the solvents of the filtrate (red) were evaporated. The residue was dissolved in diethyl ether and extracted with water (2×50 mL). The organic layer was separated, dried (Na₂SO₄), filtered and the solvent was evaporated and the residual crystalline material was washed with cold MeOH, leaving white crystals (needles), which were dried in vacuum (4.6 g, 10%) melting at 112° C.

GC/MS showed M⁺ 430 (100%)

$^1$H NMR (CDCl₃, 300 MHz) δ: 6.32 (s, CH, 2H), 0.20 (s, Si(CH₃)₃ 36H).

$^{13}$C NMR (CDCl₃, 75 MHz) δ: 140.17, 113.63, 000.15.

EXAMPLE 73

Tris(8-nitroethenyl-2,2,6,6-tetramethylbenzo[1,2-d:4,5-d']bis(1,3)dioxole-4-yl)methane

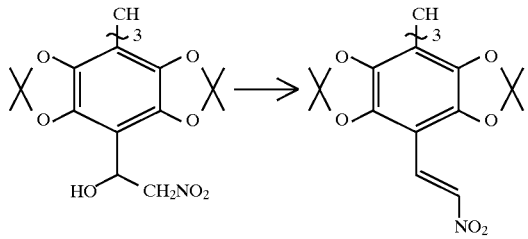

Tris (8-nitromethylhydroxymethyl-2,2,6,6-tetramethylbenzo-[1,2-d:4,5-d )bis(1,3)dioxole-4-yl) methane (0.670 g, 0.710 mmol (Example 83)) was dissolved in Ac₂O (30 mL) and NaOAc (2.00 g, 24.4 mmol) was added and the reaction mixture was refluxed for 0.5 h. The solution turned deep red. The solvent was evaporated and the residue was partitioned between ether (100 mL) and water (50 mL). The organic layer was separated, dried (Na₂SO₄), filtered and the solvent was evaporated yielding a deep red crystalline residue (0.62 g, 98%). The $^1$H NMR and $^{13}$C NMR spectra were in identical to those recorded for the same product, given in Example 82.

EXAMPLE 74

3,4-Dihydroxy-2,5-thiophenyl dicarboxylic acid diethylester

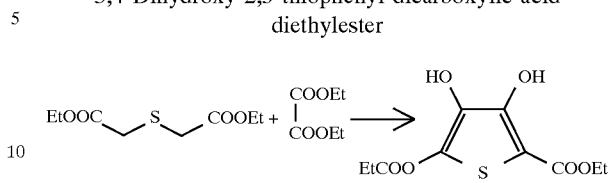

Sodium (27.8 g, 1.21 mol) was dissolved cautiously in refluxing absolute EtOH (1300 mL) and a mixture of bis (ethoxycarbonylmethyl)sulfide (108.0 g, 0.540 mol) and diethyl oxalate (81.8 g, 0.540 mol) was added dropwise. The reaction mixture was refluxed for 1 hour, allowed to cool, filtered and acidified. The new precipitate was filtered and dried (80° C.) in vacuum. Recrystallization from EtOH:EtOAC (1:1) (450 mL) gave two crops of the thiophene; 93.2 g (67%).

$^{13}$C NMR (DMSOd₆, 75 MHz) δ: 161.93, 150.15, 107.92, 60.80, 14.11.

EXAMPLE 75

3,4-Methylenedioxy-2,5-thiophenedicarboxylic acid diethylester

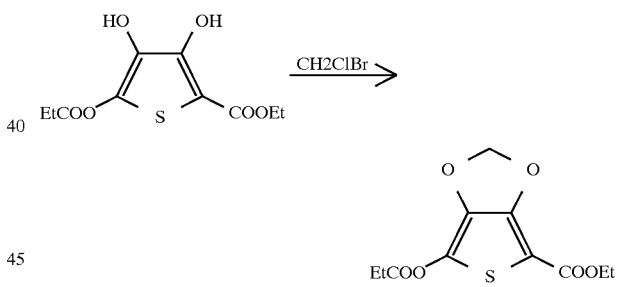

3,4-Dihydroxy-2,5-thiophenyl dicarboxylic acid diethylester (68.4 g, 300 mmol (Example 74)), bromochloromethane, K₂CO₃ (40.0 g) and Na₂S₂O₄ (4 spoons) were mixed in DMSO (315 mL) and refluxed for 24 h. The reaction mixture was filtered, cooled and filtered again. The solvent was evaporated, leaving a solid residue which was dissolved in CH₂Cl₂ and filtered. The filtrate was washed with water, 10% NaHCO₃ and water. The organic layer was separated, dried (Na₂SO₄), filtered and the solvent was evaporated, yielding a crystalline residue, which was recrystallized from absolute EtOH (800 mL; the filtration performed while the solvent was hot), yielding the desired product 3,4-methylenedioxy-2,5-thiophenedicarboxylic acid diethylester (11.8 g, 15%), melting at 124° C.

$^{13}$C NMR (DMSOd₆, 75 MHz) δ: 160.13, 151.51, 113.36, 104.20, 61.87, 14.46.

EXAMPLE 76

3,4-Methylenedioxy-2,5-thiophenedicarboxylic acid monoethylester

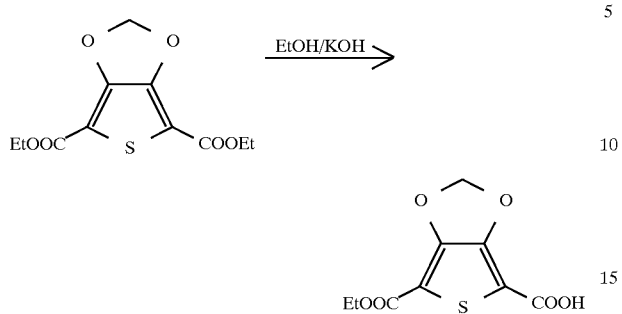

3,4-Methylenedioxy-2,5-thiophenedicarboxylic acid diethylester (3.08 g, 11.3 mmol (Example 75)) was refluxed in EtOH/KOH (88 mL EtOH and 5.57 g, 11.3 mmol KOH) for 48 h. The reaction mixture was allowed to cool and the precipitate was filtered and the filter cake was triturated with cold 0.1M HCl. The basic filtrate from the first filtration was also triturated with 0.1M HCl and the crystals from these acidifications were pooled, dried and later recrystallized from water/EtOH (1:1) and yielded 2.62 g (95%) of the desired mono-carboxylic acid.

$^{13}$C NMR (DMSOd$_6$, 75 MHz) δ: 161.11, 159.83, 151.07, 150.64, 112.65, 105.43, 103.39, 61.35, 14.07.

EXAMPLE 77

3,4-Methylenedioxy-2-bromo-5-ethoxycarbonyl thiophene

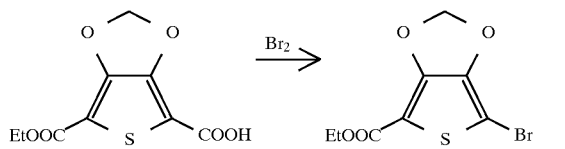

(See Chem. Ber. 108 (1975) p.576). 3,4-Methylenedioxy-2,5-thiophenedicarboxylic acid monoethylester (5.00 g, 20.5 mmol (Example 76)) was dissolved in water (115 mL) and the solution was made alkaline to pH 11 with K$_2$CO$_3$. The solution was filtered and warmed to 50° C. before Br$_2$ (1.8 mL) was added during a period of 1 h. Crystals precipitated, the precipitate was filtered off and the filter cake was washed with water and dried, yielding 2.3 g (34%) of the desired product, melting at 93° C.

$^{13}$C NMR (DMSOd$_6$, 75 MHz) δ: 160.11, 150.32, 147.09, 110.75, 102.96, 85.64, 6.45, 14.33.

EXAMPLE 78

3,4-Methylenedioxy-2-bromo-5-carboxy thiophene

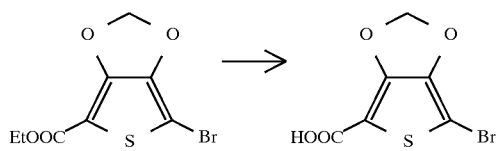

NaOH (10%) and MeOH were mixed in the proportion 1:1 (80 mL) and added to 3,4-methylenedioxy-2-bromo-5-ethoxycarbonyl thiophene (1.91 g, 7.00 mmol (Example 77)), and the reaction mixture was heated to 60°–70° C. and kept there for 2h. After cooling, the reaction mixture was filtered and the MeOH of the filtrate was evaporated and water was added. Acidification with 10% HCl precipitated the free acid 3,4-methylenedioxy-2-bromo-5-carboxy thiophene, which was filtered and dried in a desiccator (P$_2$O$_5$), yielding 1.41 g (82%).

MS (EI 70 ev): M$^+$ 324 and 322 of the TMS derivative.

EXAMPLE 79

3,4-Methylenedioxy-2-bromo-thiophene-5-carboxylic acid chloride

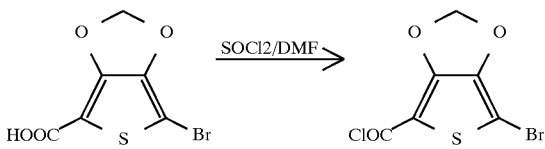

3,4-Methylenedioxy-2-bromo-5-carboxy thiophene (9.64 g, 38.4 mmol (Example 78)) was dissolved in dry DMF (0.73 mL) and SOCl$_2$ (38 mL) was added and the reaction mixture was refluxed for 5 hours. Excess SOCl$_2$ was removed by distillation under reduced pressure, yielding 9.75 g (94%) of the acid chloride, which was used in the next reaction (see Example 80) without further purification.

EXAMPLE 80

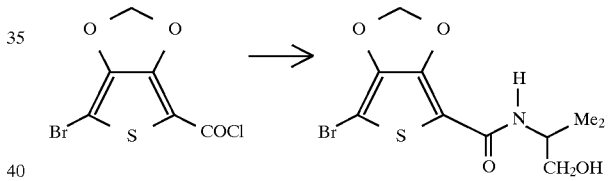

The crude 3,4-methylenedioxy-2-bromo-thiophene-5-carboxylic acid chloride from Example 79 (0.398 mmol) was dissolved in CH$_2$Cl$_2$ (1.0 mL) and slowly added dropwise to a mixture of 2-amino-2-methyl-1-propanol (0.478 mmol) and 4,4-dimethylamino pyridine (0.059 g, 0.478 mmol) in CH$_2$Cl$_2$ (1.0 mL) at 0° C. After 12 h at room temperature water (2 mL) was added and the organic phase was separated and washed with two more portions of water (2×2 mL). The organic phase was dried by passing it through a small pipette packed with ground CaCl$_2$ and evaporated yielding 0.1286 g (85%).

GC/MS on the TMS derivative showed (M$^+$–TMS+H) at m/e 321/323 (containing Br).

EXAMPLE 81

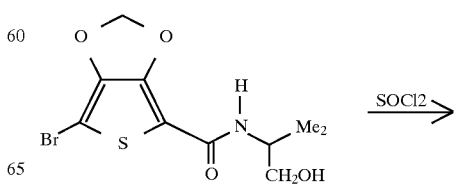

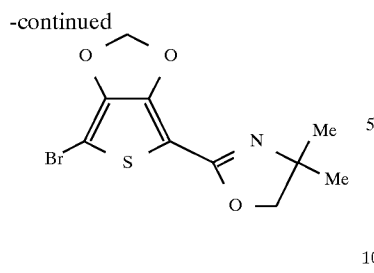

The product of Example 80 (0.100 g, 0.370 mmol) was dissolved in $CH_2Cl_2$ and chilled to 0° C. and molecular sieves (3 Å, dried at 350° C. in vacuum) were added before adding $SOCl_2$ (740 mmol). The reaction mixture was stirred at room temperature over night. Excess solvent and $SOCl_2$ were removed under reduced pressure and the residue was partitioned between 10% $Na_2CO_3$ and $CH_2Cl_2$. The organic phase was separated, dried ($Na_2SO_4$), filtered and the solvent was evaporated yielding 0.050 g (44%) of the desired product.

GC/MS on the TMS derivative showed $M^+$ at 303/305 (containing Br).

EXAMPLE 82

Tris(8-nitroethenyl-2,2,6,6-tetramethylbenzo[1,2-d:4,5-d']bis(1,3)dioxole-4-yl)methane

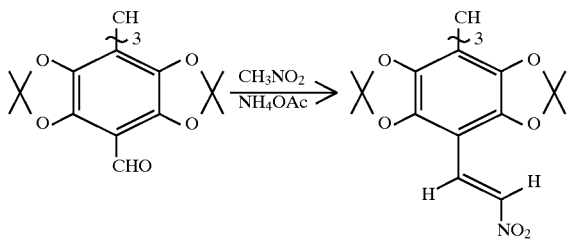

Tris(8-formyl-2,2,6,6-tetramethylbenzo[1,2-d:4,5-d']bis(1,3)dioxole-4-yl)methan (0.45 g, 0.59 mmol, (Example 23)), nitromethane (20 mL, 290 mmol) and ammonium acetate (0.12 g, 1.56 mmol) were mixed and heated to 100° C. for 6.5 h. After cooling, water (70 mL) was added, followed by ether (100 mL). The organic phase was separated, dried ($Na_2SO_4$) and the solvents evaporated, leaving a dark-red oil, which solidified after pump drying, yielding 0.38 g (72%) of the product.

$^1$H NMR ($CDCl_3$, 300 MHz) δ: 7.98 (d, CH—$NO_2$, $^1$H, JHH 11 Hz) 7.80 (d, CH, $^1$H, JHH 11 Hz), 5.41 (s, CH, $^1$H), 1.54 (s, $CH_3$, 36H).

$^{13}$C NMR ($CDCl_3$, 300 MHz) d:137.10, 136.86, 136.01, 126.29, 116.63, 107.32, 95.42, 68.89, 22.78.

MS (EI): $M^+$+1891 (40%), $M^+$ 890 (75%), 818 (100%).

EXAMPLE 83

Tris(8-nitromethylhydroxymethyl-2,2,6,6-tetramethylbenzo[1,2-d:4,5-d']bis-(1,3)dioxole-4-yl)methane

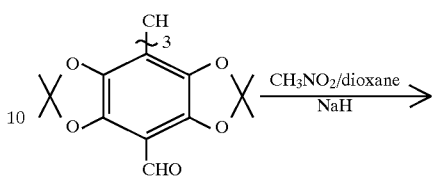

Tris(8-formyl-2,2,6,6-tetramethylbenzo[1,2-d:4,5-d']bis-(1,3)dioxole-4-yl)methane (0.150 g, 0.197 mmol, Example 23) and nitromethane (0.36 g, 5.9 mmol) were mixed in dry dioxane (20 mL), and NaH (0.030 g, 0.197 mmol, 80% in oil) was added at ambient temperature. After stirring overnight, the reaction was checked by TLC, and found to be completed. IR (film on NaCl) of the reaction mixture confirmed this, no CHO fragment coud be detected. Water (50 mL) and a few drops of HCl (2M) were added. The mixture was extracted with ether (3×50 mL). The organic extracts were washed with water (40 mL), dried ($Na_2SO_4$) and the solvent was evaporated, leaving a crystalline yellow residue. The product was chromatographed on a column of silica with $CH_2Cl_2$,EtOAc 45:5 as eluent. The fractions containing pure product were pooled and the solvent was evaporated, yielding 0.150 g (81%).

$^1$H NMR ($CDCl_3$, 300 MHz) δ: 5.40–5.50 (m, CH—O, $^1$H), 5.36 (s, CH, $^1$H), 4.79–4.86 (m, $CH_2NO_2$, $^1$H), 4.61–4.66 (m, $CH_2$—$NO_2$, $^1$H), 3.07 (s, OH, $^1$H), 1.50 (s, $CH_3$).

$^{13}$C NMR ($CDCl_3$, 75 MHz) δ: 139.87, 137.08, 118.38, 118.21, 78.80, 64.94, 30.58, 25.36 and 25.30 ($CH_3$, two resonances due to assymmetry).

EXAMPLE 84

Tris(8-diethylaminocarbonyl-2,2,6,6-tetramethylbenzo[1,2-d:4,5-d']bis-(1,3)dioxole-4-yl) methyl Tris(8-diethylaminocarbonyl-2,2,6,6-tetramethylbenzo[1, 2-d:4,5-d']bis-(1,3)dioxole-4-yl)methane (0.076 g, 0.080 mmol (Example 87)) was dissolved in a mixture of of dry THF (40 mL, sodium benzophenone ketyl) and dry DMSO (10 mL, molecular sieves 4 Å) under $N_2$. KOtBu (0.009 g, 0.080 mmol) was added and the mixture stirred at room temperature for 4 hours.

n-BuLi (0.1 mL, 2.5M in toluene, 0.25 mmol) was added, and the colour of the reaction mixture changed to dark red, after which $I_2$ (0.041 g, 0.16 mmol) was added. A sample of this solution was investigated by ESR spectroscopy, indicating a radical content of <5% Overhauser enhancement 2–10 at 2 W.

EXAMPLE 85

Tris(8-methylthiobenzo[1,2-d:4,5-d']bis(1,3)dioxole-4-yl)methanol and tris(8-methylthiobenzo[1,2-d:4,5-d']bis(1,3)dioxole-4-yl)methyl

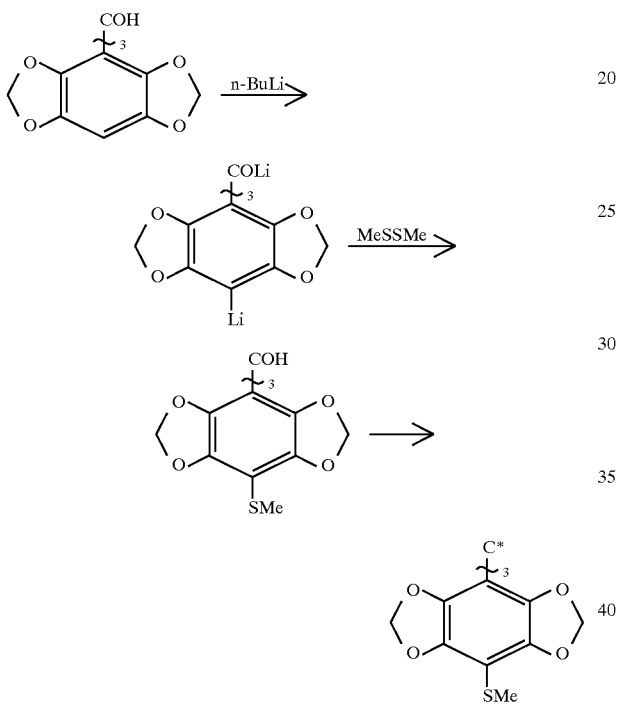

Tris(benzo[1,2-d:4,5-d']bis(1,3)dioxole-4-yl)methanol (1.00 g, 1.90 mmol (Example 3) was mixed with dry THF (25 mL, sodium benzophenone ketyl) under Ar (g) and cooled to −78° C. n-BuLi (3.8 mL, 2.5M solution in hexane) was added with a syringe. The cooling bath was removed and the resulting mixture was allowed to reach room temperature. The mixture turned thick and pasty and THF (25 mL, sodium benzophenone ketyl) was added in order to facilitate stirring. After 1 day $CH_3SSCH_3$ (1 mL) was added. The mixture became homogeneous (and dark) almost instantaneously. After 2 hours, the reaction mixture was poured on ice-water (200 mL) and extracted with $CH_2Cl_2$ (3×100 mL). The organic phase was dried ($MgSO_4$) and filtered and the solvent was evaporated to give a dark brown syrup, which was dissolved in $CHCl_3$, filtered through $SiO_2$ and evaporated to a new syrup. The brown syrup was chromatographed on $SiO_2$ with $Et_2O$ as eluent. (The sample was applied to the column in a mixture of $Et_2O/CH_2Cl_2$). Yield 1.05 g, 84%.

MS (EI 70 ev): $M^+$+662, 646, 616, 570.

Tris(8-methylthiobenzo[1,2-d:4,5-d']bis(1,3)dioxole-4-yl)methanol was converted to the corresponding radical with $BF_3 \cdot OEt_3$ (cation formation) and $CrCl_2$ (reductant) as described in other Examples. The ESR spectrum showed a linewidth of 120 mG in THF at a concentration of 1 mM. The Overhauser enhancement was 10 at 5 W.

EXAMPLE 86

2,6-Disilicium-2,2,6,6-tetra-tert-butylbenzo[1,2-d:4,5-d']bis(1,3)dioxole

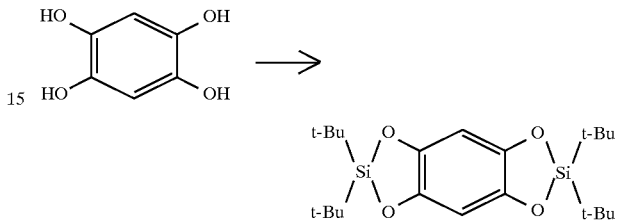

1,2,4,5-Tetrahydroxybenzene (0.284 g, 2.0 mmol (Example 4)) and imidazole (0.81 g, 12.0 mmol) were dissolved in dry DMF (15 ml) and di-t-butyldichlorosilane (1.28 g, 6.0 mol) was added dropwise with stirring. The solution was stirred for 15 h, diethyl ether (50 ml, sodium benzophenone ketyl) was added. The organic phase was washed with HCl (2×25 ml, 5%), NaOH 2×25 ml, 1M), water (25 ml), dried and evorporated, yielding 0.50 g of a solid yellow residue. Recrystallization from diisopropyl ether gave 0.330 g (39%) pure, slightly yellow compound.

$^1$H NMR ($CDCl_3$, 300 MHz) δ: 6.12 (s, CH, 2H), 1.05 (s, bu, 36H).

MS (EI, 70 ev, GLC inlet) m/e: 425 (3), 424 (12), 423 (36), 422 (100), 383 (14), 382 (31)

EXAMPLE 87

Tris(8-diethylaminocarbonyl-2,2,6,6-tetramethylbenzo[1,2-d:4,5-d']bis(1,3)dioxol-4-yl) methane and bis(8-diethylaminocarbonyl-2,2,6,6-tetramethylbenzo[1,2-d:4,5-d']bis(1,3)dioxole-4-yl) mono(2,2,6,6-tetramethyl-benzo[1,2-d:4,5-d']bis(1,3)dioxole-4-yl)methane

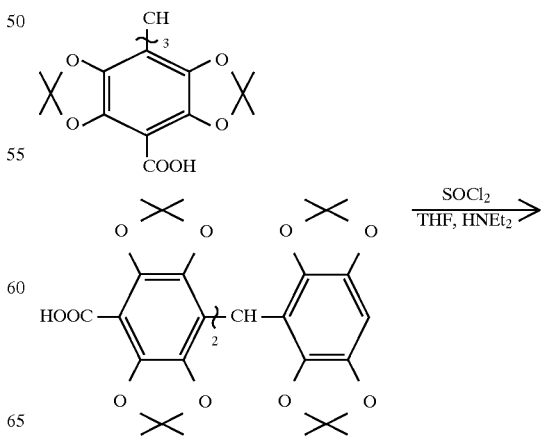

-continued

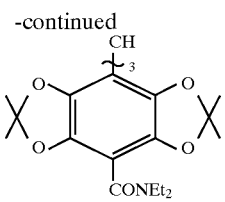

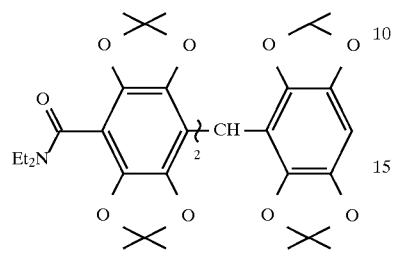

A crude mixture of tris(8-carboxyl-2,2,6,6-tetramethylbenzo[1,2-d:4,5-d']bis(1,3)dioxole-4-yl)methane and bis(8-carboxyl-2,2,6,6-tetramethylbenzo[1,2-d:4,5-d']bis(1,3)dioxole-4-yl)mono(2,2,6,6,-tetramethylbenzo[1,2-d:5-d']bis(1,3)dioxole-4-yl)methane (1.00 g, from Example 18) was dissolved in dry THF (10 mL) at room temperature, $SOCl_2$ (0.61 mL, 8.4 mmol) was added, and stirring was continued for 2.5 hours. The solvent and excess $SOCl_2$ was evaporated under reduced pressure, leaving a brown crystalline residue, which was dried on a vacuum pump (<1 torr) for 10 h. This residue was dissolved in dry THF (5 mL), and $Et_2NH$ (1.50 g, 21.0 mmol) was added and stirred for 12 hours. The reaction mixture was partitioned between ether (75 mL) and water (50 mL). The organic phase was separated, dried ($Na_2SO_4$), filtered and the solvent was evaporated leaving a brown crystalline residue. Chromatograhpic (RP8, 10 μm, 20×250 mm, $CH_3CN:H_2O$ 75:25) separation, yielded 0.100 g (0.098 mmol, 14%) of tris(8-diethylaminocarbonyl-2,2,6,6-tetramethylbenzo[1,2-d:4,5-d']bis(1,3)dioxole-4-yl)methane and 0.150 g (160 mmol, 37%) of bis(8-diethylaminocarbonyl-2,2,6,6-tetramethylbenzo[1,2-d:4,5-d']bis(1,3)dioxole-4-yl)mono(2,2,6,6-tetramethyl-benzo[1,2-d:4,5-d']bis(1,3)dioxole-4-yl)methane. The yields are calculated for two steps (including the reaction in Example 18). Tris(8-diethylaminocarbonyl-2,2,6,6-tetramethylbenzo[1,2-d:4,5-d']bis(1,3)dioxole-4-yl)methane:

$^1$H NMR (300 MHz. $CDCl_3$) δ: 1.06–1.12 (t, $CH_3$. 3H), 1.17–1.24 (t, $CH_3$. 3H), 1.52 (s, $CH_3$, 36H), 3.26–3.37 (q, $CH_2$, 2N), 3.51–3.60 (q, $CH_2$. 2H), 5.41 (s, CH, 1H).

Bis(8-diethylaminocarbonyl-2,2,6,6-tetramethylbenzo[1,2-d:4,5-d']bis(1,3)dioxole-4-yl)-mono(2,2,6,6-tetramethylbenzo[1,2-d:4,5-d']bos(1,3)dioxole-4-yl)methane $^1$H NMR (300 MHz. $CDCl_3$) δ: 1.06–1.12 (t, $CH_3$. 3H), 1.17–1.24 (t, $CH_3$. 3H), 1.52 (s, $CH_3$, 24H), 1.54 (s, $CH_3$, 12H), 3.26–3.37 (q, $CH_2$. 2H), 3.51–3.60 (qs, $CH_2$, 2H), 5.41 (s, CH, 1H), 6.21 (s, aromatic H, 1H).

EXAMPLE 88

Tris(8-formyl-2,2,6,6-tetramethylbenzo[1,2-d:4,5-d']bis(1,3)dioxole-4-yl)methyl bisulfite adduct

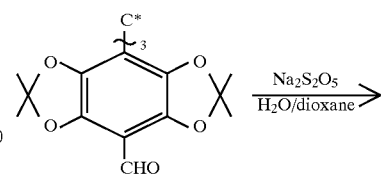

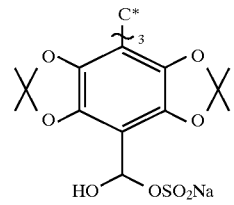

Tris(8-formyl-2,2,6,6-tetramethylbenzo[1,2-d:4,5-d']bis(1,3)dioxole-4-yl)methyl (0.065 g, 0.976 mmol (Example 64)), with a radical content of about 10%, and $Na_2S_2O_5$ (0.370 g, 1.95 mmol) were mixed in a 25 mL round flask under $N_2$ (g). Water (1.5 mL, He degassed 15 min.) and dioxane (1.5 mL, He degassed 15 min.) were added. After 15 minutes stirring most of the solid material had dissolved. HPLC analysis showed that the starting aldehyde was consumed after 45 minutes. An Overhauser experiment confirmed the presence of radical in the reaction mixture. Overhauser enhancement was 59 at 5 W microwave power. ESR four lines, Linewidth 133 mG, $a_H$ 973 mG.

The bisulfite adduct was precipitated by the addition of dioxane and the precipitate was filtered and washed twice with dioxane. The product was dried under vacuum in room temperature overnight.

EXAMPLE 89

Tris(8-formyl-2,2,6,6-tetramethylbenzo[1,2-d:4,5-d']bis(1,3)dioxole-4-yl)methane bisulfite adduct

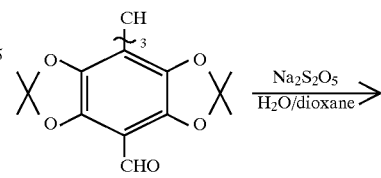

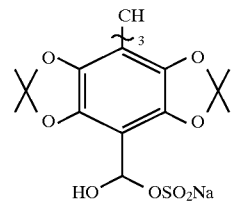

This reaction was performed with tris(8-formyl-2,2,6,6-tetramethylbenzo[1,2-d:4,5-d']bis-(1,3)dioxole-4-yl)methane (0.050 g, 0.066 mmol (Example 23)), and $Na_2S_2O_5$ (0.285 g, 1.5 mmol) analogous to the formation of the bisulfite adduct of tris(8-formyl-2,2,6,6-tetramethylbenzo[1,2-d:4,5-d']bis-(1,3)dioxole-4-yl)methyl radical as detailed above in Example 88, yielding 0.140 g (the theoretical yield is 0.070 g) of crystals containing $NaHSO_3$.

$^1$H NMR (300 MHz, D$_2$O) δ: 1.4 (d, CH$_3$, 36H), 5.2 (s, CH, $^1$H), 5.3 (s, CH—OH, 3H).

$^{13}$C NMR (75 MHz, D$_2$O) d: 24.4 (d, CH$_3$), 28.0 (s, CH), 102 (s), 107 (s), 119 (s), 138 (s), 140 (s), 164 (s)

EXAMPLE 90

Tris(4-carboxy-2,3,5,6-tetrachlorophen-1-yl)methyl

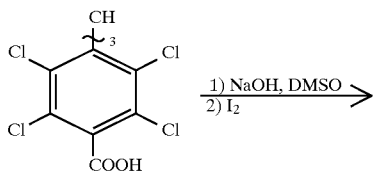

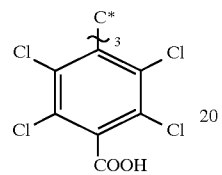

Tris(4-carboxy-2,3,5,6-tetrachlorophen-1-yl)methane (0.690 g, 0.87 mmol) [(1 R (KBr, cm$^{-1}$) 3450 (O—H str.), 2920 (C—H str), 1720 (C=O str.), 1550, 1420 (C—C in chlorinated aryls). $^1$H NMR (CD$_3$OD, 300 MHz) δ: 8.00 (s, CH, $^1$H), $^{13}$C NMR (CD$_3$OD, 75 MHz)) δ: 164.35, 132.40, 132.26, 133.00. 132.00, 56.88.] was mixed with NaOH (s) (0.090 g, 3.6 mmol) in DMSO (10 mL) and stirred for 24 hours in the dark. I$_2$ (0.110 g, 0.43 mmol) was dissolved in ether (40 mL) and this solution was added and the resulting mixture was stirred for 15 minutes. The reaction mixture was poured on saturated NaHCO$_3$ (100 mL) The phases were separated and the aqueous phase (pH 2) was acidified to pH 1–2 (conc. HCl). The acidic aqueous phase was extracted with ether (2×100 mL). The ether phase were combined, dried (Na$_2$SO$_4$), filtered and the solvent was evaporated yielding a tan semi-crystalline residue of 0.250 g (36%).

ESR (200 G): One line, Linewidth 570 mG.

Overhauser enhancements (0.2M in H$_2$O, 200 G, 548.9 MHz) 2–10 at 2 w microwave power.

EXAMPLE 91

Tris(4-trichloromethyl-2,3,5,6-tetrachlorophen-1-yl)methyl

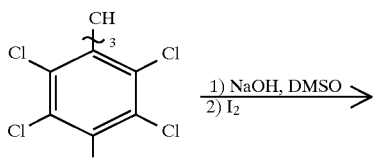

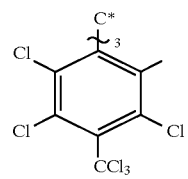

Tris(4-trichloromethyl-2,3,5,6-tetrachlorophen-1-yl)methane was converted to the corresponding radical as described in Example 90.

ESR (200 G): One line, Linewidth 1500 mG.

Overhauser enhancements (200 G, 548.9 MHz) 2–10 at 2 W microwave power.

EXAMPLE 92

Tris(2,3,5,6-tetrachloro-4-methylphen-1-yl)methyl

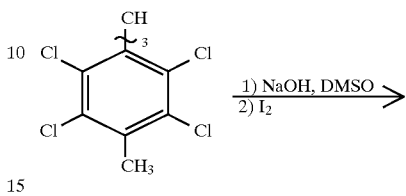

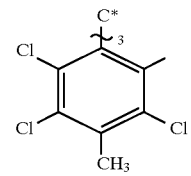

Tris(2,3,5,6-tetrachloro-4-methylphen-1-yl)methane was converted to the corresponding radical as described in Example 90.

ESR (200 G): One line, Linewidth 3200 mG.

Overhauser enhancements (200 G, 548.9 MHz) 2–10 at 2 W microwave power.

EXAMPLE 93

(Phenyl)-(pyrid-4-yl)-(thien-2-yl)methanol

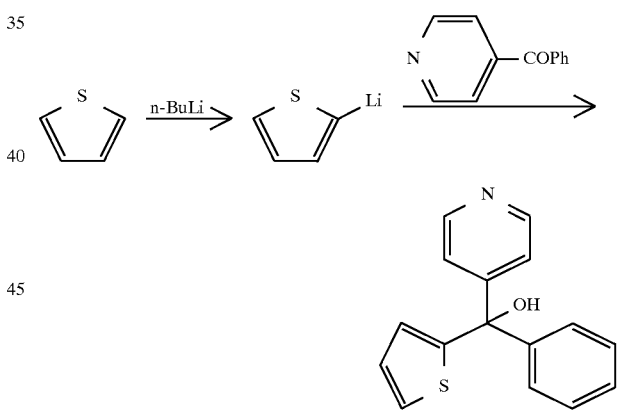

Thiophene (1.150 g, 13.60 mmol) was dissolved in diethyl ether (50 mL, sodium benzophenone ketyl) under argon. n-Butyl lithium (5.10 mL, 13.60 mmol) was added quickly with a syringe under evolution of heat. The resulting mixture was stirred for 1 hour and 15 minutes at room temperature. After cooling to –75° C., benzoylpyridine (2.50 g, 13.6 mmol) dissolved in THF (10 mL) was added over a period of 10 minutes and the resulting mixture was stirred for 60 hours at room temperature. The resulting thick yellow suspension was diluted with THF (100 mL) and NaH$_2$PO$_4$ buffer (1.25M, 100 mL) was added. The organic layer was separated and washed with more NaH$_2$PO$_4$ buffer (2×30 mL, 1.25M), dried (Na$_2$SO$_4$) and evaporated yielding 3.24 g of crude material. Chromatography (flash, TLC gel 125 g, CH$_2$Cl$_2$:diethyl ether 4:6) yielded 1.83 g (6.85 mmol, 50%) of the title compound.

¹H NMR (DMSO d₆, 300 MHz) δ: 8.49 (m, H), 7.49–7.47 (q, 1H), 7.35–7.24 (m, 7H), 6.97–6.95 (q, 1H), 6.70–6.68 (q, 1H).

¹³C NMR (DMSO d₆, 75 MHz) δ: 155.63, 151.55, 149.29, 146.14, 127.85, 127.42, 127.00, 126.48, 126.44, 125.96, 121.89, 77.97.

MS (EI 70 eV): M⁺+1 268, 190.

EXAMPLE 94

(m-Chlorophenyl)-(phenyl)-pyrid-4-yl)methanol

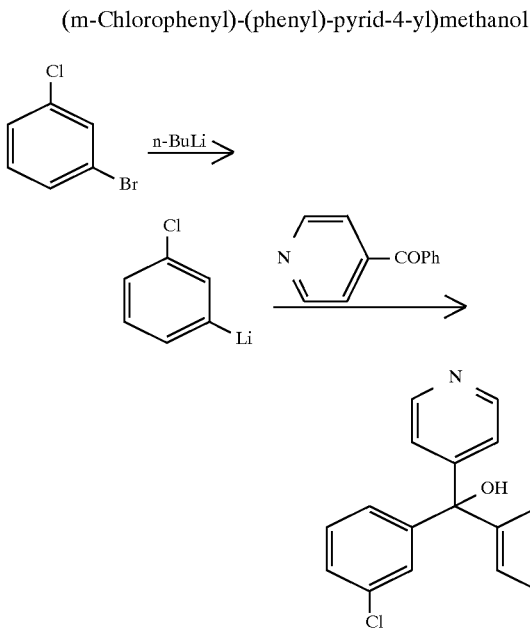

m-Chlorobromobenzene (2.60 g, 13.60 mmol) was dissolved in THF (50 mL, sodium benzophenone ketyl) under argon. The solution was cooled to −78° C. and s-butyl lithium (9.7 mL, 13.60 mmol in cyclohexane/isopentane) was added over a period of 10 minutes. The resulting mixture was stirred for 1 hour at −78° C. Benzoylpyridine (2.50 g, 13.6 mmol) dissolved in THF (10 mL) was added over a period of 5 minutes and the resulting mixture was stirred for 60 hours at room temperature. The resulting yellow solution was hydrolysed with NaH₂PO₄ buffer (1.25M, 40 mL). The organic layer was separated and washed with more NaH₂PO₄ buffer (30 mL, 1.25M), dried (Na₂SO₄) and evaporated. The solid was stirred with CH₃CN (100 mL) for 3 hours. The solid was filtered and dried and was shown by TLC and MS to be pure.

¹H NMR (DMSOd₃, 300 MHz) δ: 8.52–8.50 (q, CH pyridine 2H), 7.35–7.09 (m, 1H).

¹³C NMR (DMSOd₃, 75 MHz) δ: 155.20, 149.37, 148.88, 145.68, 132.76, 129.77, 127.99, 127.58, 127.37, 127.24, 127.16, 126.52, 122.52, 79.64.

MS (EI 70 eV): M⁺+1 296 and 298, 218, 220.

EXAMPLE 95

Tris(8-dimethylaminocarbonylthio-2,2,6,6-tetramethylbenzo[1,2-d:4,5-d']bis(1,3)-dioxole-4-yl)methane

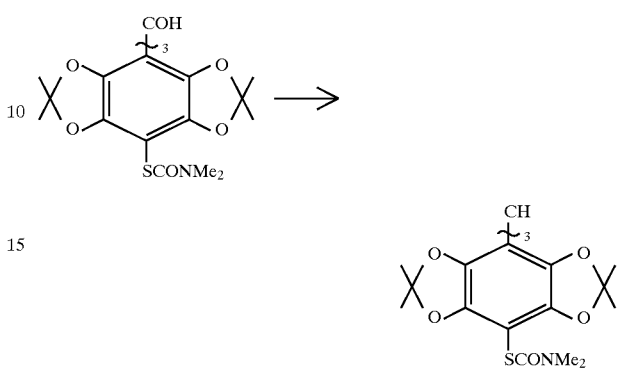

NaI (1.135 g, 8.00 mmol) and Me₃SiCl (1 mL, 8.0 mmol) were stirred in CH₃CN (70 mL) at 0° C. Tris(8-dimethylaminocarbonylthio-2,2,6,6-tetramethylbenzo-[1,2-d:4,5-d']bis(1,3)-dioxole-4-yl)methanol (1.00 g, 0.9979 mmol (Example 43)) dissolved in CH₃CN 10 mL) was added and the resulting solution stirred for 30 minutes when ¹H NMR analysis of a small sample showed conversion to be complete. Na₂S₂O₃ (sat., 30 mL) was added and the two phase system was stirred 30 minutes when more Na₂S₂O₃ (sat. 30 mL) was added and the stirring was continued for 5 more minutes. The phases were separated and the organic layer was dried (MgSO₄), filtered, the filter washed with diethyl ether (30 mL) and the solution was evaporated, yielding 1.16 g yellow to brown crystals. The crystals were dissolved in CH₂Cl₂, the solution was washed with NaHCO₃ (30 mL, sat.) and H₂O (30 mL), dried (MgSO₄) and evaporated yielding 0.92 g of the pure title compound.

¹H NMR (CDCl₃, 300 MHz) δ: 5.38 (s, 1H) 3.04 (s, 9H), 2.94 (s, 9H), 1.51 (s, 36H).

¹³C NMR (CDCl₃, 75 MHz) δ: 163.22, 142.11, 139.50, 117.93, 108.75, 90.79, 36.91, 30.96, 25.30.

MS (Thermospray): M⁺+18 1003.

EXAMPLE 96

Bis(8-methylmercapto-2,2,6,6-tetramethylbenzo[1,2-d:4,5-d']bis(1,3)dioxole-4-yl)-mono(2-methylmercaptopyrimidin-5-yl )methyl

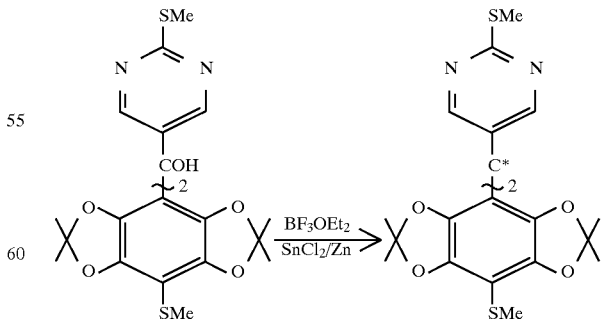

Bis(8-methylmercapto-2,2,6,6-tetramethylbenzo[1,2-d:4,5-d']bis(1,3)dioxole-4-yl)-mono(2-methylmercaptopyrimidin-5-yl)methanol (0.075 g, 0.109 mmol (Example 60)) was dissolved in THF (75 mL, sodium benzophenone ketyl). BF$_3$.OEt$_2$ (0.475 mL, 1.853 mmol, 48% in diethyl ether) was added. The color changed from yellow to green. The solution was stirred for 15 minutes and SnCl$_2$ (0.103 g, 0.545 mmol) was added. 30 minutes later Zn (0.178 g, 2.725 mmol) was added and there followed an immediate color change to yellow/brown/greyish. More Zn (0.230 g, 3.51 mmol) was added one hour after the first addition. After leeting the Zn settle, a sample was taken with a gas tight syringe and an Overhauser enhancement experiment was performed on this solution. The measured enhancement was 100 at 5 W microwave power.

EXAMPLE 97

Bis(8-methoxycarbonylmethylthio-2,2,6,6-tetramethylbenzo[1,2-d:4,5-d']bis(1,3)dioxole-4-yl) mono(8-ethoxycarbonylmethylthio-2,2,6,6-tetramethylbenzo[1,2-d:4,5-d']bis(1,3)dioxole-4-yl) methanol

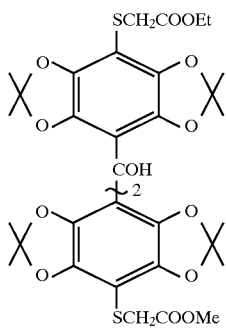

The title product was isolated by HPLC as a by product from the reaction described in Example 12.

$^{13}$C NMR (CDCl$_3$, 75 MHz) δ: 169.50, 168.99, 141.33, 141.28, 138.64, 138.62, 117.77, 117.75, 112.53, 112.33, 96.66, 96.46, 72.48, 52.30, 35.45, 35.40, 25.42.

EXAMPLE 98

Bis(8-mercapto-2,2,6,6-tetramethylbenzo[1,2-d:4,5-d']bis(1,3)dioxole-4-yl)-mono(8-methoxycarbonylmethyl-2,2,6,6-tetramethylbenzo[1,2-d:4,5-d']bis(1,3)dioxole-4-yl)methanol

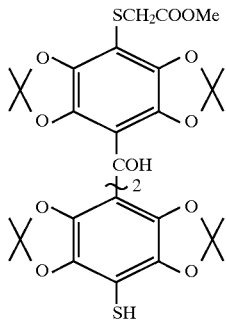

The title product was isolated by HPLC as a by product from the reaction described in Example 12.

$^{13}$C NMR (CDCl$_3$, 75 MHz) δ: 169.52, 141.25, 140.13, 138.79, 138.68, 117.66, 116.95, 112.73, 111.90, 96.46, 96.34, 72.53, 35.36, 25.39, 25.34.

EXAMPLE 99

Tris(benzothien-2-yl)methanol

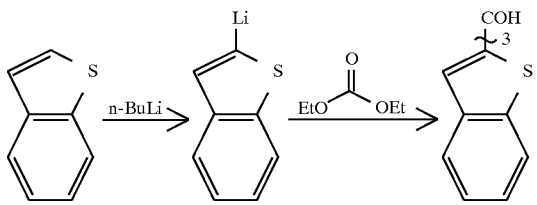

Benzothiophene (5.42 g, 0.0382 mmol) was dissolved in diethyl ether (100 mL). n-Butyl lithium (20.0 mL, 2M) was added at −15° C. under an argon atmosphere. The resulting mixture was allowed to reach room temperature and diethyl carbonate (1.54 mL) was added and when TLC showed the reaction to be complete. The mixture was worked up by adding Na$_2$HPO$_4$ buffer (100 mL, sat.), separating the phases and washing the organic phase with more buffer and water. Drying (MgSO$_4$) evaporation and chromatographic separation yielded 1.40 g (25.7%) of the title compound.

$^{13}$C NMR (CDCl$_3$, 75 MHz) δ: 150.12, 140.08, 139.03, 124.48, 124.08, 123.44, 122.37, 50.80.

EXAMPLE 100

4-Allylthio-2,2,6,6-tetramethylbenzo[1,2-d:4,5-d']bis(1,3)dioxole

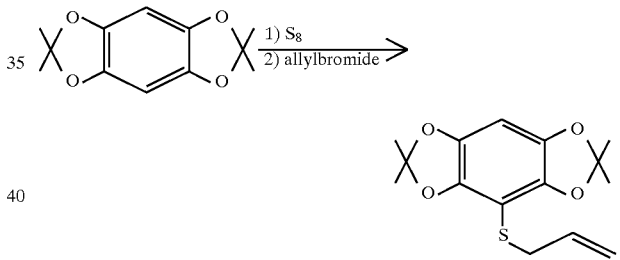

The title product was synthesized from 2,2,6,6-tetramethylbenzo[1,2-d:4,5-d']bis(1,3)dioxole (4.5 g, 0.02 mmol (Example 5)), n-butyl lithium (9.0 mL, 2.5M), S$_8$ (0.70 g) and allylbromide (2.42 g, 1.73 mL) in THF. Yield 4.9 g (83%) of a yellow brown oil.

$^{13}$C NMR (CDCl$_3$, 75 MHz) δ: 141.82, 139.90, 133.76, 118.25, 117.38, 98.31, 92.72, 36.66, 25.56.

EXAMPLE 101

Tris(8-di(methylcarbonyloxyethyl) aminocarbonylmethylthio-2,2,6,6-tetramethylbenzo[1,2-d:4,5-d']bis(1,3)-dioxole-4-yl)methyl

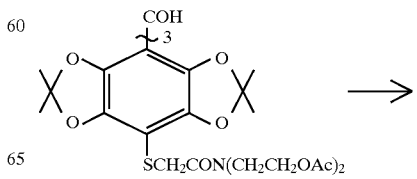

-continued

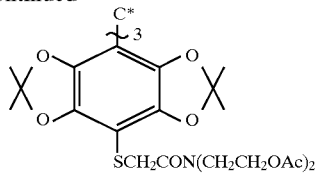

SCH₂CON(CH₂CH₂OAc)₂

Tris(8-di(methylcarbonyloxyethyl) aminocarbonylmethylthio-2,2,6,6-tetramethylbenzo-[1,2-d:4,5-d']bis(1,3)-dioxole-4-yl)methanol (0.098 g, 0.066 mmol (Example 38)) was dissolved in THF (30 mL, Al₂O₃). BF₃.OEt₂ (3.00 mL, 11.77 mmol, 48% in diethyl ether) was added. The solution was stirred for 30 minutes and SnCl₂ (0.159 g, 1.122 mmol) was added. 30 minutes later Zn (0.108 g) was added and there followed an immediate color change from blue to brown. After letting the Zn settle, a sample was taken with a gas tight syringe and an Overhauser enhancement experiment was performed on this solution. The measured enhancement was 28 at 4 mW microwave power and 69 at 0.77 W.

ESR (200 G, THF solution): One line, linewidth 187 mG.

EXAMPLE 103

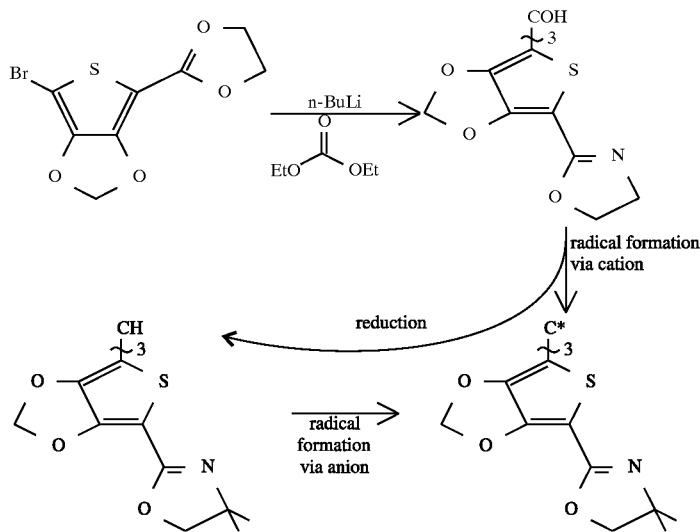

The bromo oxazolidine thiophene of Example 81 is trimerized to the corresponding trityl by treatment with one equivalent of n-butyl lithium in THF at −75° C. for 30 minutes. 0.3 equivalents of diethyl carbonate is added at this temperature and the solution is allowed to reach room temperature over a period of several hours. The reaction mixture is worked up by pouring the solution on cold NH₄Cl or cold Na₂HPO₄ buffer followed by extraction with diethyl ether or CH₂Cl₂. The organic phase is washed with water, dried (Na₂SO₄) and is evaporated to yield the crude carbinol. The pure compound is obtained by chromatography on either SiO₂ or RP₈ gel. The product is characterised by ¹H NMR and ¹³C NMR as well as other spectroscopic methods. The methanol compound is either converted directly to the radical or first to the methane.

EXAMPLE 104

Bis(8-formyl-2,2,6,6-tetramethylbenzo[1,2-d:4,5-d']bis(1,3)dioxole-4-yl)ketone

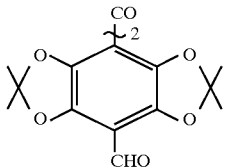

2,2,6,6-Tetramethylbenzo[1,2-d:4,5-d']bis-(1,3)dioxole (8.88 g, 0.040 mol (Example 5)) was dissolved in THF (250 mL) and cooled to −20° C. under a N₂ atmosphere. n-Butyl lithium (19.2 mL, 2.5M in toluene) was added and the temperature was allowed to increase to +10° C. over a period of 10 minutes. The mixture was then cooled to −20° C. and DMF (2.92 g, 0.040 mol) was added and the temperature was allowed to reach room temperature in 2 hours. The mixture was again cooled to −20° C. and a second portion of n-butyl lithium (19.2 mL, 2.5M in toluene) was added. The temperature was allowed to reach room temperature in 1 hour. After once again recooling to −20° C., dimethyl carbonate (1.19 g, 0.0132 mol) was added and the temperature was allowed to reach room temperature overnight. Water (300 mL) and acetic acid (2 mL) were added and the solution was extracted with ether (3×150 mL). The organic extracts were combined, dried (Na₂SO₄ and K₂CO₃) and the solvent evaporated leaving a semi-crystalline dark residue. The residue was crystallized twice from EtOAc:heptane 4:1 giving the title compound as a deep red crystalline product. Yield 3.0 g (43%).

¹H NMR (CDCl₃, 300 MHz) δ: 10.11 (s, CHO, 2H), 1.68 (s, CH₃, 24H).

¹³C NMR (CDCl₃, 75 Mz) δ: 185.25, 183.05, 141.08, 139.72, 121.48, 112.12, 108.09, 25.72.

IR (KBr): 1700 (vs, C=) in CHO, 1670 (s, C=O).

EXAMPLE 105

Tris(8-formyl-2,2,6,6-tetramethylbenzo[1,2-d:4,5-d'] bis(1,3)dioxole-4-yl)methanol and bis(8-formyl-2,2,6,6-tetramethylbenzo[1,2-d:4,5-d']bis(1,3)dioxole-4-yl)mono(2,2,6,6-tetramethylbenzo[1,2-di:4.5-d']bis(1,3)dioxole-4-yl)methanol and mono(8-formyl-2,2,6,6-tetramethylbenzo[1,2-d:4,5-d']bis(1,3)dioxole-4-yl)bis(2,2,6,6-tetramethylbenzo[1,2-d:4,5-d']bis(1,3)dioxole-4-yl)methanol

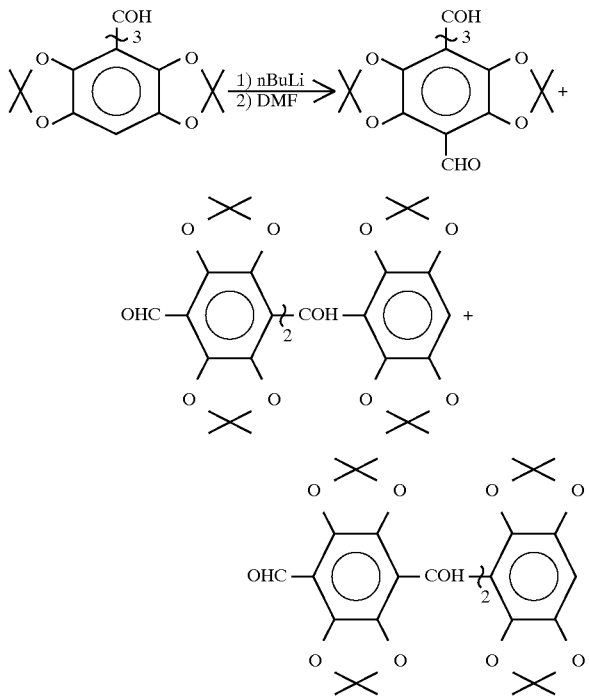

Tris(2,2,6,6-tetramethylbenzo[1,2-d:4,5-d']bis(1,3)dioxole-4-yl)methanol (10.0 g, 0.0145 mol (Example 44)) was suspended in dry diethyl ether (300 mL). n-butyl lithium (29 mL, 0.0725 mol, 2.5M in hexane) was added, under nitrogen, and the solution was heated slowly to reflux temperature (ca. 20 min.). A second portion of n-butyl lithium (9.8 mL, 2.5M in hexane) was added and the heating was disrupted. 5 minutes after removal of the oil bath, DMF (130 mL, 0.169 mol) was added carefully. The resulting mixture was stirred at room temperature over night. Water (300 mL) and AcOH was (5 mL) was added to the solution. An orange colour appeared in the solution at this time. The mixture was extracted with diethyl ether (2×300 mL). The combined organic phase was washed with wather (3×100 mL), dried ($Na_2SO_4$, $K_2CO_3$), treated with charcoal and filtered through $SiO_2$ (3 cm, i.d. 5 cm) and evaporated. The residual brown residue was dried under vacuum to leave a form weighing 11.1 g. This material was chromatographed on several columns of $SiO_2$ with $CH_2Cl_2$:EtOAc 45:5 as eluent.

Yield of tris(8-formyl-2,2,6,6-tetramethylbenzo[1,2-d:4,5-d']bis(1,3)dioxole-4-yl)methanol 1.8 g (16.9%).

$^1$H NMR (CDCl$_3$, 300 MHz) δ: 10.08 (s, CHO, 3H), 4.32 (s, OH, 1H), 1.55 (s, CH$_3$, 36H).

$^{13}$C NMR (CDCl$_3$, 75 MHz) δ: 185.41, 140.82, 139.25, 119.58, 116.58, 105.76, 72.71, 25.62.

MS (Thermospray); M$^+$+23 (Na) 799.

Yield of bis(8-formyl-2,2,6,6-tetramethylbenzo[1,2-d:4,5-d']bis-(1,3)dioxole-4-yl)-mono(2,2,6,6-tetramethylbenzo[1,2-d:4,5-d']bis(1,3)dioxole-4-yl)methanol 4.5 g (42%).

$^{13}$C NMR (CDCl$_3$, 75 MHz) δ: 185.51, 140.77, 140.31, 139.41, 138.62, 119.34, 117.53, 117.19, 110.80, 105.59, 92.31, 72.70, 25.60, 25.44.

MS (Thermospray): M$^+$+23 (Na) 771.

Yield of mono(8-formyl-2,2,6,6-tetramethylbenzo[1,2-d:4,5-d']bis(1,3)dioxole-4-yl)-bis(2,2,6,6-tetramethylbenzo[1,2-d:4,5-d']bis(1,3)dioxole-4-yl)methanol 2.1 g (20.1%).

$^{13}$C NMR (CDCl$_3$, 75 MHz) δ: 185.69, 140.73, 140.19, 139.57, 138.81, 119.12, 118.58, 116.95, 111.67, 105.43, 91.98, 72.71, 25.59, 25.43.

MS (Thermospray): M$^+$+23 (Na) 743.

EXAMPLE 106

4-Formyl-2,2,6,6-tetramethylbenzo[1,2-d:4,5-d']bis(1,3)dioxole

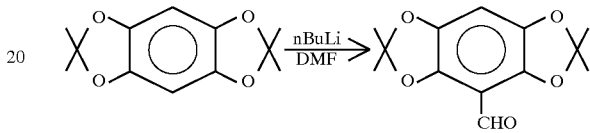

2,2,6,6-Tetramethylbenzo[1,2-d:4,5-d']bis(1,3)dioxole (20.0 g, 90 mmol (Example 5)) was dissolved in THF (300 mL) and cooled to −20° C. n-Butyl lithium (38.0 mL), 2.5M in toluene, 100 mmol) was added and the temperature was allowed to rise to 0° C. The mixture was recooled to −20° C. and DMF (6.9 mL, 90.0 mmol) was added. The reaction mixture was stirred over night while allowing the temperature to increase to room temperature. Water (200 mL) and AcOH (5 mL) was added. The color changed from light yellow to strong orange. The mixture was extracted with diethyl ether (3×300 mL) and the combined organic phase was washed with water (2×100 mL), dried (Na$_2$SO$_4$) and evaporated. The product was triturated twice with petroleum ether and dried, yielding the pure title compound; 16.3 g (72%).

$^{13}$C NMR (CDCl$_3$, 75 MHz) δ: 185.51, 140.84, 140.81, 120.17, 106.38, 98.26, 25.67.

EXAMPLE 107

Bis(8-formylethyleneglycolacetal-2,2,6,6-tetramethylbenzo[1,2-d:4,5-d']bis(1,3)-dioxole-4-yl)ketone

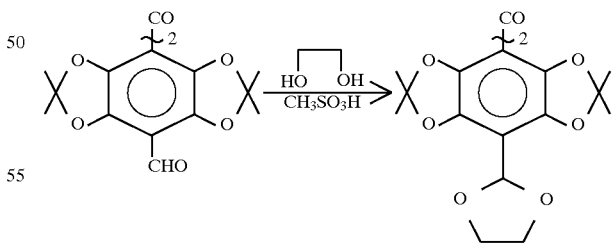

Bis(8-formyl-2,2,6,6-tetramethylbenzo[1,2-d:4,5-d']bis(1,3)-dioxole-4-yl)ketone (2.0 g, 3.80 mmol (Example 104)), ethyleneglycol (50 mL) and methanesulfonic acid (0.01 mL) were mixed and stirred at room temperature over a weekend. TLC analysis (SiO$_2$ CH$_2$Cl$_2$:Et$_2$O 4:1) indicated that the reaction was complete. Pyridine (0.5 mL) was added and the reaction mixture was partitioned between diethyl ether (200 mL) and water (250 mL). The aquous phase was extracted with more ether (2×200 mL). The combined organic phase was washed with water (100 mL), dried (Na₂SO₄) and filtered through Al₂O₃ (2.5 cm, i.d. 2 cm). The solvent was evaporated leaving a yellow crystalline product. Yield 2.12 g (90.9%).

¹H NMR (CDCl₃, 300 MHz) δ: 6.06 (s, O—C<u>H</u>—O, 2H), 4.19–4.14 (m, CH₂, 4H), 4.02–3.97 (m, CH₂, 4H), 1.61 (s, CH₃, 24H).

¹³C NMR (CDCl₃, 75 MHz) δ: 184.06, 139.68, 138.93, 119.37, 109.27, 108.82, 97.94, 65.73, 25.66.

EXAMPLE 108

Tris(2,5-dimethylthien-3-yl)methanol

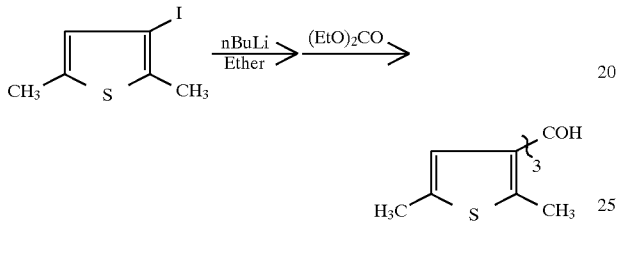

2,5-Dimethyl-3-iodo-thiophene (see S. Gronowitz and R. Beselin, Arkiv för Kemi 21: 349–355 (1963)) (0.05 mol) was dissolved in diethyl ether (150 mL, dry) and n-butyl lithium (25.0 mL, 2.06M) was added at −78° C. under N₂ and stirred for 30 minutes. Diethyl carbonate (2.0 mL, 0.0166 mol) in diethyl ether (3 mL, dry) was added and the mixture was stirred for 30 minutes. The cooling bath was removed and the temperature was allowed to reach +10° C. At this temperature the mixture was poured onto ice/water. The organic phase was separated and washed with water (2×50 mL), dried (MgSO₄) and evaporated. The resulting oil was taken up in petroleum ether. After cooling the product was filtered and washed with a little petroleum ether. Yield 41.6%, mp. 110°–111° C.

¹H NMR (C₆D₆, 300 MHz) δ: 6.46 (H₄, 3H), 2.19 (s, CH₃, 9H), 2.03 (s, CH₃, 9H), 1.70 (CO<u>H</u>, 1H).

MS (EI 70 eV): M⁺−1 361.

MS (Thermospray): M⁺−17 345.

EXAMPLE 109

Tris(2,5-dimethylthien-3-yl)methane

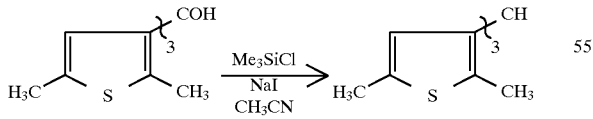

Tris(2,5-dimethylthien-3-yl)methanol (Example 108)) was converted to tris(2,5-dimethylthien-3-yl)methane using Me₃SiCl, CH₃CN and NaI as described in several previous Examples, e.g. 17, 61, 62 and 95. Yield 67.8%, mp. 143°–144° C.

¹H NMR (CDCl₃, 300 MHz) δ: 6.28 (s, 3H), 5.07 (s, methane CH, 1H), 2.34 (s, CH₃, 9H), 2.18 (s, CH₃, 9H).

EXAMPLE 110

Tris(2,5-dimethylthien-3-yl)methanol

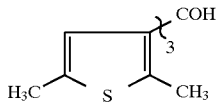

Tris(2,4,5-trimethylthien-3-yl)methanol

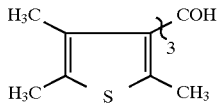

Bis(2,5-dimethylthien-3-yl)-mono-(2,3-dimethyl-4-iodothien-5-yl)-methanol

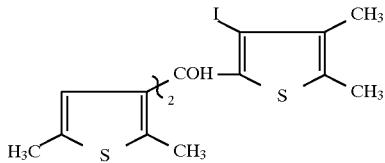

Bis(2,5-dimethylthien-3-yl)-mono(2,5-di-t-butyl-thien-3-yl)-methanol

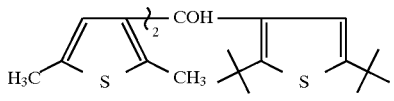

The title carbinols were made according to the same general procedure: To a stirred solution of the corresponding mono- or diiodinated thiophene (0.05 mol) in diethyl ether (150 mL, dry) was added n-butyl lithium (25.0 mL, 2.06M) at −70° C. under N₂. The solution was stirred for 30 minutes at this temperature. The appropriate ketone (see A. Wiersma and S. Gronowitz Acta Chem Scand 24: 2593–2611 (1970) and Ya L. Goldfarb and P. A. Konstantinov, Bull. Acad. Sci. USSR, Engl transl., 108 1959) (0.05 mol), dissolved in diethyl ether (150 mL), was added and the resulting solution was stirred for 30 minutes at this temperature. The cooling bath was removed and when the reaction mixture had reached +10° C. the mixture was poured on ice and water. The workup was as described in Example 108.

Tris(2,5-dimethylthien-3-yl)methanol
MS (Thermospray): M⁺−17 345
Tris(2,4,5-trimethylthien-3-yl)methanol
Yield: 3.5%
MS (Thermospray): M⁺−17 723
Bis(2,5-dimethylthien-3-yl)-mono-(2,3-dimethyl-4-iodothien-5-yl)-methanol
Yield: 13.3%
MS (Thermospray): M⁺−17 471
Bis(2,5-dimethylthien-3-yl)-mono(2,5-di-t-butyl-thien-3-yl)-methanol
Yield: 5.6%
MS (Thermospray): M⁺−17 429

EXAMPLE 111

(Phenyl)-(pyrid-4-yl)-(thien-2-yl)methane

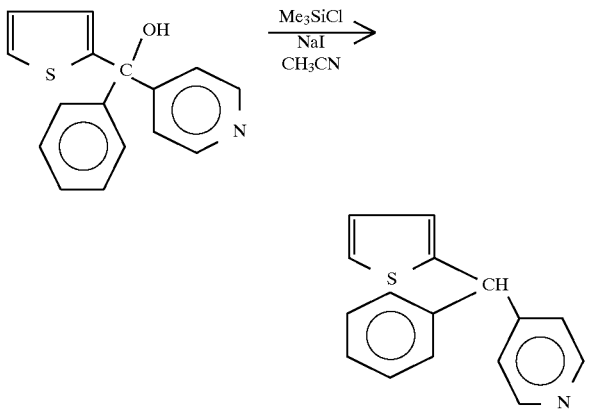

NAI (2.27 g, 16.0 mmol) and Me₃Sicl (2.02, 16.0 mmol) were stirred in CH₃CN (70 mL) at 0° C. (Phenyl)-pyrid-4-yl-(thien-2-yl)methanol (0.534 g, 2.00 mmol (Example 93)) was added at 0° C. and the resulting solution was stirred over night at room temperature. Na₂S₂O₃ (sat., 20 mL) was added and the two phase system was stirred 5 minutes. The phases were separated and the organic layer was dried (MgSO₄), filtered and evaporated. The resulting crystals were dissolved in CH₂Cl₂ (30 mL), the solution was washed with NaHCO₃ (30 mL, sat.) and H₂O (30 mL), dried (MgSO₄) and evaporated yielding 0.41 g which was recrystallized in diisopropyl ether giving 0.22 g (43.8%) of the pure title compound.

¹H NMR (CDCl₃, 300 MHz) δ: 8.53 (m, 2H), 7.37–7.11 (m, 8H), 6.96 (q, 1H), 6.71 (dt, 1H) 5.64 (broad s, 1H).

¹³C NMR (CDCl₃, 75 MHz) δ: 152.33, 149.91, 145.53, 141.98, 128.72, 128.63, 127.23, 126.73, 126.71, 125.04, 123.89, 51.37.

EXAMPLE 112

Bis(thien-2-yl)-mono-(4-methoxyphenyl)methyl

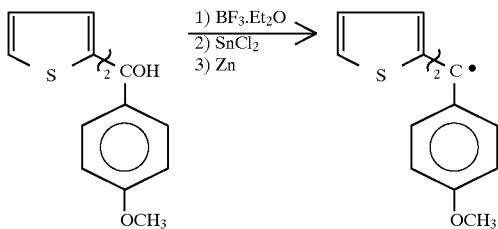

The carbinol of Example 115 (0.140 g, 0.463 mmol) was dissolved in dry (Al₂O₃ filtered and Ar (g) saturated) THF (30 mL) and BF₃.Et₂O (1.12 g, 7.87 mmol) was added and stirring was maintained 30 minutes when SnCl₂ (0.437 g, 2.31 mmol) was added. After stirring for another 30 minutes, Zn dust (0.756 g, 11.6 mol) was added and the stirring was continued. 30 minutes after the Zn addition a sample was taken with a gas tight syringe, after letting the Zn settle, and Overhauser measurements showed some radical formation to have occurred.

EXAMPLE 113

Tris(8-diethylaminocarbonylmethylthio-2,2,6,6-tetramethyl-benzo[1,2-d:4,5-d']bis(1,3)dioxole-4-yl)methanol

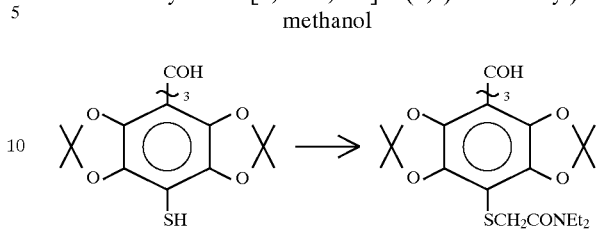

Tris(8-mercapto-2,2,6,6-tetramethylbenzo[1,2-d:4,5-d']bis(1,3)dioxole-4-yl)methanol (1.00 g, 1.269 mmol (Example 31)) was added to a solution consisting of CH₃CN (50 mL), K₂CO₃ (5.0 g and BrCH₂CONEt₂ (0.776 g, 4.0 mmol) made from BrCH₂COBr and HNEt₂ in CH₂Cl₂) at –5° C. under argon. The cooling bath was removed and the temperature increased to +23° C. A ¹H NMR control of a small sample 20 minutes after the removal showed complete conversion to have occurred. Diethyl ether (50 mL) was added and the solution was filtered. The solvents were evaporated and the residual 1.28 g of oily material was heated in diisopropyl ether (30 mL, 40° C.). The material did not dissolve but changed into crystalline form in this process. Filtration and drying gave 0.96 g (67.0%) of the title compound.

¹H NMR (CDCl₃, 300 MHz) δ: 4.16 (s, COH 1H), 3.36 (q, NCH₂CH₃, 6H), 3.32 (q, NCH₂CH₃, 6H), 1.50 (s, CH₃, 36H), 1.18 (t, CH₃, 9H, 1.08 (t, CC₃, 9H).

¹³C NMR (CDCl₃, 75 MHz) δ: 166.92, 141.20, 138.63, 117.57, 112.21, 97.18, 75.52, 42.44, 40.13, 35.97, 25.48, 14.30, 12.83.

EXAMPLE 114

Tris(8-diethylaminocarbonylmethylthio-2,2,6,6-tetramethyl-benzo[1,2-d:4,5']bis(1,3)dioxole-4-yl) methyl

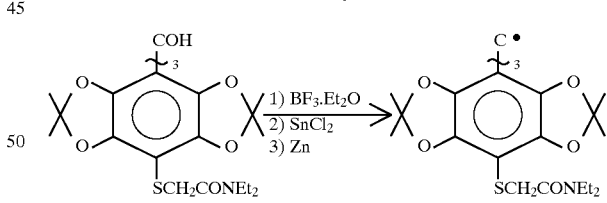

Tris(8-diethylaminocarbonylmethylthio-2,2,6,6-tetramethylbenzo[1,2-d:4,5']bis(1,3)dioxole-4-yl)methanol (0.100 g, 0.0886 mmol) was dissolved in dry (Al₂O₃ filtered and Ar (g) saturated) THF (30 mL) and BF₃.Et₂O (0.214 g, 1.51 mmol) was added and the color changed immediately from yellow to blue, and stirring was maintained during 30 minute. SnCl₂ was added (0.084 g, 0.443 mmol) and the stirring was continued for one hour. Zn dust (0.145 g, 2.22 mmol) was added and one hour later another portion of Zn dust (0.124 g, 1.89 mmol) was added. An experiment one later on a crude sample from the reaction mixture, after letting the Zn settle, showed a 108 fold Overhauser enhancement at 4 mW microwave power.

EXAMPLE 115

Bis(thien-2-yl)mono(4-methoxyphenyl)methanol

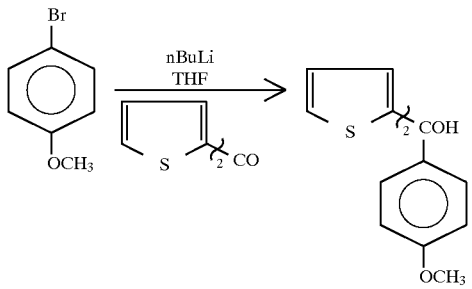

p-Bromo methoxybenzene (0.96 g, 5.2 mmol) was dissolved in THF (50 mL) and n-butyl lithium (2.08 mL, 2.5M in toluene) was added at −70° C. and stirred at this temperature for 10 minutes when the thienyl ketone (1.0 g 5.2 mmol) (see JACS 74: 1733–36 (1952), JCS 1956, 698–705 and Receuil 68: 24 (1949)) dissolved in THF (5 mL) was added. The temperature was allowed to rise gradually to room temperature over night. The mixture was hydrolysed with water (50 mL). Ether (150 mL) was added and the phases were separated, the aqueous phase was extracted with more ether (100 mL) and the combined organic phase was washed with water (70 mL), dried (MgSO$_4$) and the solvent evaporated leaving a semi-crystalline black residue. The black residue was dissolved in hot heptane/EtOAc (3:1) and chromatographed on a column of alumina with heptane: EtOAc 3:1 as eluent. The product was isolated in a yield of 0.72 g (46.0%).

$^1$H NMR (CDCl$_3$, 300 MHz) δ: 7.38 (d, armoatic H m to OCH$_3$, 2H, J 9 Hz), 7.29 (q, thiophene H α to S, 2H, J 5.1 Hz, J 1.2 Hz), 6.95 (q, thiophene H β to S, 2H, J 5.1 Hz, J 3.6 Hz), 6.86 (d, aromatic H o to OCH$_3$ 2H, J 9 Hz), 6.85 (s, thiophene γ to S, 2H, J 3.6 Hz, J 1.2 Hz), 3.81 s. OCH$_3$, 3H), 3.04 (s, OH, 1H).

$^{13}$C NMR (CDCl$_3$, 75 MHz) δ: 159.04, 152.05, 138.36, 126.38, 126.37, 125.60, 113.12, 77.65, 55.18.

MS (EI 70 eV): M$^+$ 302 (10%), M$^+$−16 286 (100%), M$^+$−17 285 (90%).

EXAMPLE 116

Tris(8-proparqylthio-2,2,6,6-tetramethyl-benzo[1,2-d:4,5-d']bis(1,3)dioxole-4-yl)methanol

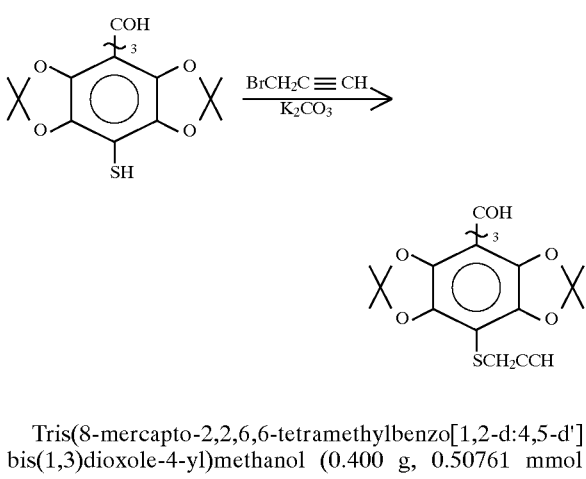

Tris(8-mercapto-2,2,6,6-tetramethylbenzo[1,2-d:4,5-d'] bis(1,3)dioxole-4-yl)methanol (0.400 g, 0.50761 mmol (Example 31)) was added to a solution consisting of CH$_3$CN (50 mL), K$_2$CO$_3$ (5.0 g) and BrCH$_2$CCH (2.389 g, 2.284 mmol) at −5° C. under argon. The cooling bath was removed and the temperature increased to +23° C. A$^1$H NMR control of a small sample 20 minutes after the removal showed conversion to be complete. Diethyl ether (50 mL) was added and the solution was filtered. The solvents were evaporated and the residual oil weighed 0.401 g (87%).

$^1$H NMR (CDCl$_3$, 300 MHz) δ: 4.15 (s, 1H, OH), 3.51 (d, 6H, CH$_2$), 2.97 (t, 3H, CCH), 1.47 (s, CH$_3$, 36H).

$^{13}$C NMR (CDCl$_3$, 75 MHz) δ: 141.35, 138.38, 11.49, 112.38, 96.31, 79.73, 72.32, 70.80, 25.26, 21.55.

The product may be substituted at the alkyne hydrogen by lithiation followed by reaction with carbon dioxide or with R*Lv where R* is the group (e.g. an alkyl group) to be introduced and Lv is a leaving group.

EXAMPLE 117

The following known free radicals were tested for Overhauser enhancement:

| Radical | Power | Overhauser enhancement |
|---|---|---|
| 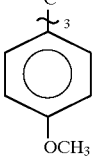 | 37 mW<br>5 W | 2<br>70 |

(See Bert et al JACS 54: 3250 (1932):
Dunnebacke et al Chem. Ber. [1989] 122 533;
Judeikis et al JACS [1961] 84, 1132;
Sinclair et al JACS [1968] 90, 5074.

| | | |
|---|---|---|
| 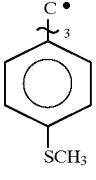 | 37 mW<br>5 W | 6.5<br>107 |

(see Dunnebacke et al (supra))

| | | |
|---|---|---|
| 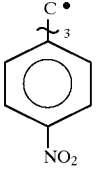 | 5 W | 7 |

(ESR Linewidth 250 mG)
(See Anderson et al Acta. Chem. Scand.
(1962), 16, 1817–1818;
Falle et al, Canad. J. Chem.
(1986), 44 1387;
Ziegier et al, Annalen (1927), 458, 248;
Allan et al, J.C.S. (1986), 440; and
Anderson et al, Acta. Chem. Scand,
(1962), 16, 1817).

| | | |
|---|---|---|
| 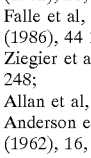 | 5 W | 7 |

| Radical | Power | Overhauser enhancement |
|---|---|---|
| (ESR linewidth 600 mG $a_H$ 1200 mG) (See Gomberg JACS [1900], 22, 757 | | |

EXAMPLE 118

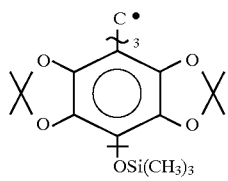

The title compound was prepared following the reaction scheme:

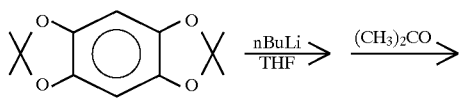

(Example 5)

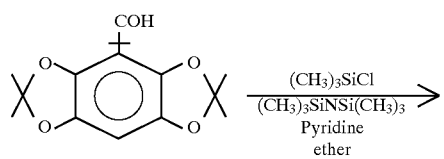

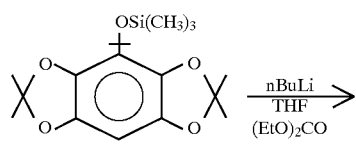

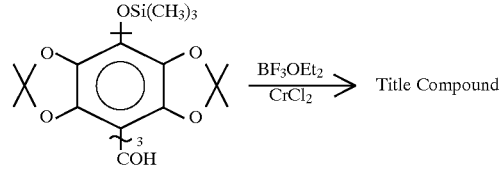

The title compound showed Overhauser enhancements of 52 at 3.5 W and 2 at 22 mW. The ESR spectrum showed a linewidth of 65 mG.

FORMULATION EXAMPLES

Example I

Intravenous enhancement agent

An Overhauser MRI enhancement solution is prepared as follows:

The freeze dried radical e.g. that of Example 11 is dissolved in oxygen-free water containing sodium chloride to ensure isotonicity. The pH of the solution is adjusted with tris buffer to pH 7.4. CaNa EDTA is added to prevent metal catalyzed oxidation. Ascorbic acid is added as an-antioxidant.

An injectable solution is prepared which contains:

| Radical | 70 mmol |
|---|---|
| Sodium chloride | q.s. |
| Tris buffer | q.s. |
| CaNa EDTA | 0.1 mmol |
| Ascorbic acid | 0.01 mmol |
| Aqua purificata | ad 500 ml |

Example II

Intravenous enhancement agent

An Overhauser MRI enhancement is prepared as follows:

The radical (e.g. that of Example 11) is dissolved in water containing NaCl, KCl, $CaCl_2$ and $MgSO_4$ in physiological ratios of the cations to ensure isotonic solution. The pH of the solution is adjusted to pH 7.4 with HCl, NaOH or tris buffer.

A small amount of iron(III) chloride is added to prevent reduction of the radical.

An injectable solution is prepared which contains:

| Radical | 50 mmol |
|---|---|
| Sodium chloride | q.s. |
| KCl, $CaCl_2$, $MgSO_4$ | q.s. |
| Tris buffer | q.s. |
| $FeCl_3$ | 0.01 mmol |
| Aqua purificata | ad 400 ml |

Example III

Oral Overhauser MRI enhancement agent for abdominal studies

A suspension for oral Overhauser MRI studies is prepared as follows:

A radical (e.g. that of Example 11) is added to a vigorously stirred solution of hydroxyethylcellulose in water (pre-stirred for 2.5 h) containing CaNa EDTA to prevent metal-catalyzed oxidation. Aspartame and a solution of anis essence, and methyl and propyl parahydroxybenzoates in ethanol are slowly added. The suspension is filled into a 700 ml bottle. The suspension contains 5 mmol radical.

| Radical | 5 mmol |
|---|---|
| Hydroxyethylcellulose | 7.9 g |
| Methyl parahydroxybenzoate | 0.7 g |
| Propyl parahydroxybenzoate | 0.14 g |
| Ethanol | 10 g |
| Aspartame | 0.2 g |
| Anis essence | 0.2 g |
| CaNa EDTA | 0.1 mmol |
| Water | ad 700 ml |

Example IV

Preparation of capsules containing an Overhauser MRI enhancement agent for oral use

| Radical (e.g. of Example 11) | 300 mg |
|---|---|
| Amylum may dis | q.s. |

The powders are mixed and filled into capsules. (Capsule size 0)

Example V

Liposomal Overhauser MRI enhancement agents for intravenous administration

The radical (e.g. that of Example 11) is encapsulated in small unilamellar vesicles according to the method described in EP-A-160552 (Vestas).

The purified liposome dispersion is filled into 50 ml vials and freeze dried. Each vial contains 1 mmol radical. The product is suspended in 30 ml saline before administration.

Example VI

Low concentration intravenous enhancement medium

The enhancement media of Examples I and II are diluted, 1 part by volume with 99 parts by volume of water for injections to produce more dilute contrast media suitable for use with sensitive SQUID based magnetometers.

Still lower concentrations, e.g. at the 10–10–10–6M level, can be produced by further dilution.

Example VII

Intravenous Overhauser MRI enhancement agent

An Overhauser enhancement solution is prepared as follows:

The radical (e.g. that of Example 11) is dissolved in water containing NaCl, KCl, $CaCl_2$, $MgSO_4$ in physiological ratio to ensure isotonicity solution. The pH of the solution is adjusted to pH 7.4 with HCl, NaOH or tris buffer A small amount of iron(III) chloride is added to prevent reduction of the radical.

An injectable solution is prepared which contains:

| Radical | 50 mmol |
|---|---|
| Sodium chloride | q.s. |
| KCl, $CaCl_2$, $MgSO_4$ | q.s. |
| Tris buffer | q.s. |
| $FeCl_3$ | 0.01 mmol |
| Aqua purificata | ad 170 ml |

Example VIII

Intravenous Qverhauser MRI enhancement agent

An Overhauser enhancement solution is prepared as follows:

The freeze dried radical (e.g. of Example 11) is dissolved in oxygen-free water. The pH of the solution is adjusted with tris buffer to pH 7.4. CaNa EDTA is added to prevent metal-catalyzed oxidation. Ascorbic acid is added as an antioxidant.

An injectable solution is prepared which contains:

| Radical | 70 mmol |
|---|---|
| Sodium chloride | q.s. |
| Tris buffer | q.s. |
| CaNa EDTA | 0.1 mmol |
| Ascorbic acid | 0.01 mmol |
| Aqua purificata | ad 50 ml |

We claim:

1. In a method of generating an electron spin resonance enhanced magnetic resonance image of a sample which comprises introducing into said sample a magnetic resonance signal enhancing amount of a free radical and generating an enhanced electron spin resonance image of said sample, wherein the improvement comprises using as said free radical an inert triarylmethyl free radical, wherein each aryl moiety of said triarylmethyl radical, which may be identical or different, comprises an optionally substituted 6-membered carbocyclic or thienyl ring.

2. A method as claimed in claim 1 wherein one or more of the aryl moieties of said triarylmethyl radical carries at least one fused ring of formula

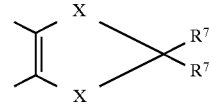

wherein each X, which may be the same or different, is an oxygen or sulphur atom, and $R^7$ represents hydrogen or an optionally hydroxylated methyl group.

3. A method as claimed in claim 1 wherein the aryl moieties of said triarylmethyl radical, which may be identical or different, each comprise an optionally substituted 6-membered carbocyclic ring optionally carrying one or more fused carbocyclic or heterocyclic rings.

4. A method of electron spin resonance investigation of a sample, said method comprising introducing into said sample an inert carbon free radical, exposing said sample to a radiation of a frequency selected to excite electron spin transitions in said free radical, detecting resonance signals from said sample, and optionally generating an image or dynamic flow from said detected signals.

5. A method as claimed in claim 4 wherein said inert carbon free radical is an inert triarylmethyl radical, wherein the aryl moieties of said triarylmethyl radical, which may be identical or different, each comprise an optionally substituted 6-membered carbocyclic ring optionally carrying one or more fused carbocyclic or heterocyclic rings.

* * * * *